(12) United States Patent
Shin et al.

(10) Patent No.: US 11,229,607 B2
(45) Date of Patent: Jan. 25, 2022

(54) HYDROGEL COMPOSITIONS COMPRISING ENCAPSULATED CELLS AND METHODS OF USE THEREOF

(71) Applicant: President and Fellows of Harvard College, Cambridge, MA (US)

(72) Inventors: Jae-Won Shin, Cambridge, MA (US); Angelo S. Mao, Cambridge, MA (US); Stefanie Utech, Cambridge, MA (US); David A. Weitz, Cambridge, MA (US); David J. Mooney, Sudbury, MA (US); Oktay Uzun, Boston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 15/321,458

(22) PCT Filed: Jun. 30, 2015

(86) PCT No.: PCT/US2015/038601
§ 371 (c)(1),
(2) Date: Dec. 22, 2016

(87) PCT Pub. No.: WO2016/004068
PCT Pub. Date: Jan. 7, 2016

(65) Prior Publication Data
US 2017/0196818 A1 Jul. 13, 2017

Related U.S. Application Data

(60) Provisional application No. 62/082,993, filed on Nov. 21, 2014, provisional application No. 62/019,284, filed on Jun. 30, 2014.

(51) Int. Cl.
| | | |
|---|---|---|
| A61K 9/48 | (2006.01) | |
| A61K 35/28 | (2015.01) | |
| A61K 9/00 | (2006.01) | |
| A61K 35/12 | (2015.01) | |
| C12N 11/10 | (2006.01) | |
| A61K 9/50 | (2006.01) | |
| C12N 11/04 | (2006.01) | |

(52) U.S. Cl.
CPC .......... *A61K 9/4816* (2013.01); *A61K 9/0019* (2013.01); *A61K 9/5036* (2013.01); *A61K 9/5052* (2013.01); *A61K 35/12* (2013.01); *A61K 35/28* (2013.01); *C12N 11/04* (2013.01); *C12N 11/10* (2013.01); *A61K 2035/124* (2013.01)

(58) Field of Classification Search
CPC ..... A61K 9/4816; A61K 9/0019; A61K 35/28
See application file for complete search history.

(56) References Cited

U.S. PATENT DOCUMENTS

| | | | |
|---|---|---|---|
| 2007/0116680 A1 | 5/2007 | Stegemann et al. | |
| 2009/0004238 A1* | 1/2009 | Scharp ................. | A61K 9/5031 424/422 |
| 2010/0021984 A1* | 1/2010 | Edd ........................ | C12N 11/04 435/174 |
| 2010/0255059 A1 | 10/2010 | Marquez et al. | |
| 2013/0345319 A1 | 12/2013 | Messersmith et al. | |
| 2014/0127290 A1* | 5/2014 | He .......................... | C12N 11/04 424/451 |

OTHER PUBLICATIONS

Li, Biomaterials, 32, 2011 (Year: 2011).*
Park, Lab Chip, 14, 2014 (Year: 2014).*
Headen et al., Microfluidic-based generation of size-controlled, biofunctionalized synthetic polymer microgels for cell encapsulation. *Adv Mater.* May 21, 2014;26(19):3003-8.
Huebsch et al., Harnessing traction-mediated manipulation of the cell/matrix interface to control stem-cell fate. *Nat Mater.* Jun. 2010;9(6):518-26.
Karoubi et al., Single-cell hydrogel encapsulation for enhanced survival of human marrow stromal cells. *Biomaterials.* Oct. 2009;30(29):5445-55.
Martinez et al., A microfluidic approach to encapsulate living cells in uniform alginate hydrogel microparticles. *Macromol Biosci.* Jul. 2012;12(7):946-51.
Selimovic et al., Microscale Strategies for Generating Cell-Encapsulating Hydrogels. *Polymers (Basel).* Sep. 2012;4(3):1554-1579.
Wan, Microfluidic-Based Synthesis of Hydrogel Particles for Cell Microencapsulation and Cell-Based Drug Delivery. *Polymers.* 2012;4:1084-1108.
International Search Report and Written Opinion for Application No. PCT/US2015/038601, dated Dec. 8, 2015. 14 pages.

* cited by examiner

*Primary Examiner* — Susan T Tran
*Assistant Examiner* — William Craigo
(74) *Attorney, Agent, or Firm* — McCarter & English, LLP; Maria Laccotripe Zacharakis

(57) ABSTRACT

The present invention provides injectable compositions comprising cells encapsulated in hydrogel capsules and methods of preparing these compositions. The present invention also provides methods for using these compositions to promote hematopoiesis and to treat or prevent cardiovascular and immunological disorders in a subject.

14 Claims, 56 Drawing Sheets
Specification includes a Sequence Listing.

FIG. 2A
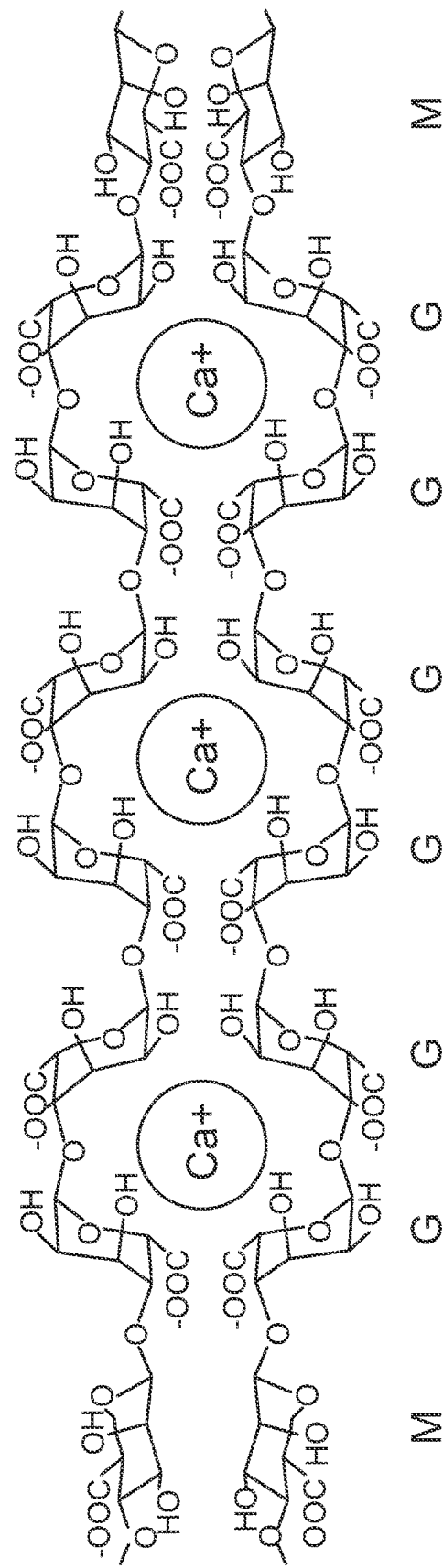
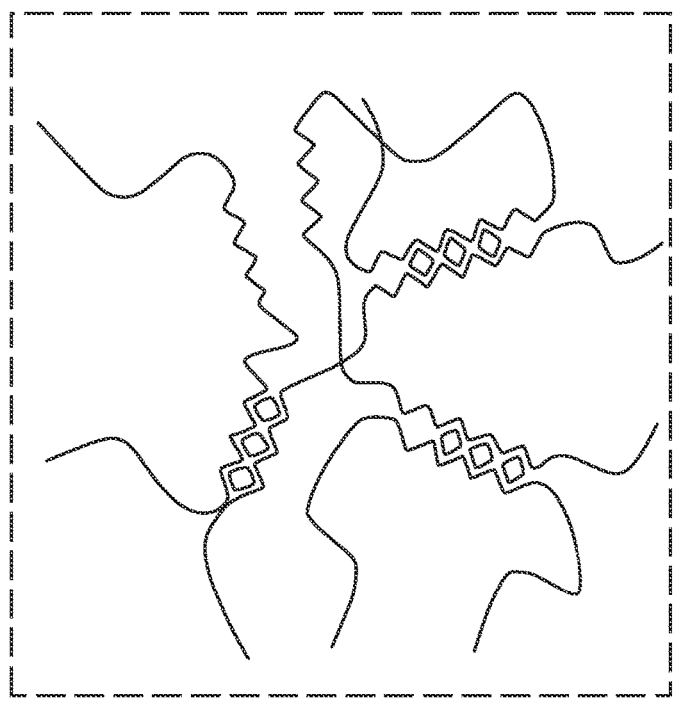

FIG. 4B
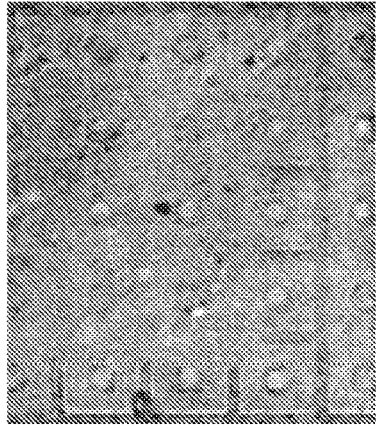
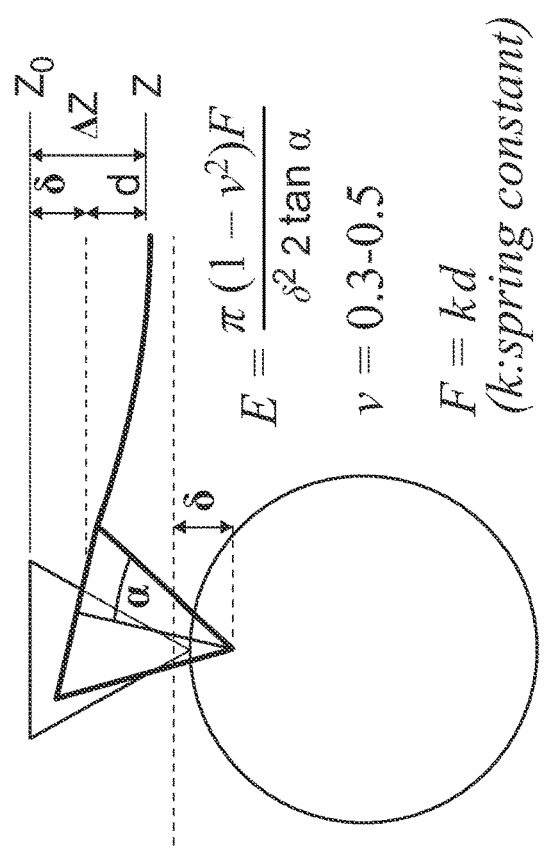
$$E = \frac{\pi(1-v^2)F}{\delta^2 2\tan\alpha}$$
$v = 0.3-0.5$
$F = kd$
(k:spring constant)
FIG. 4C
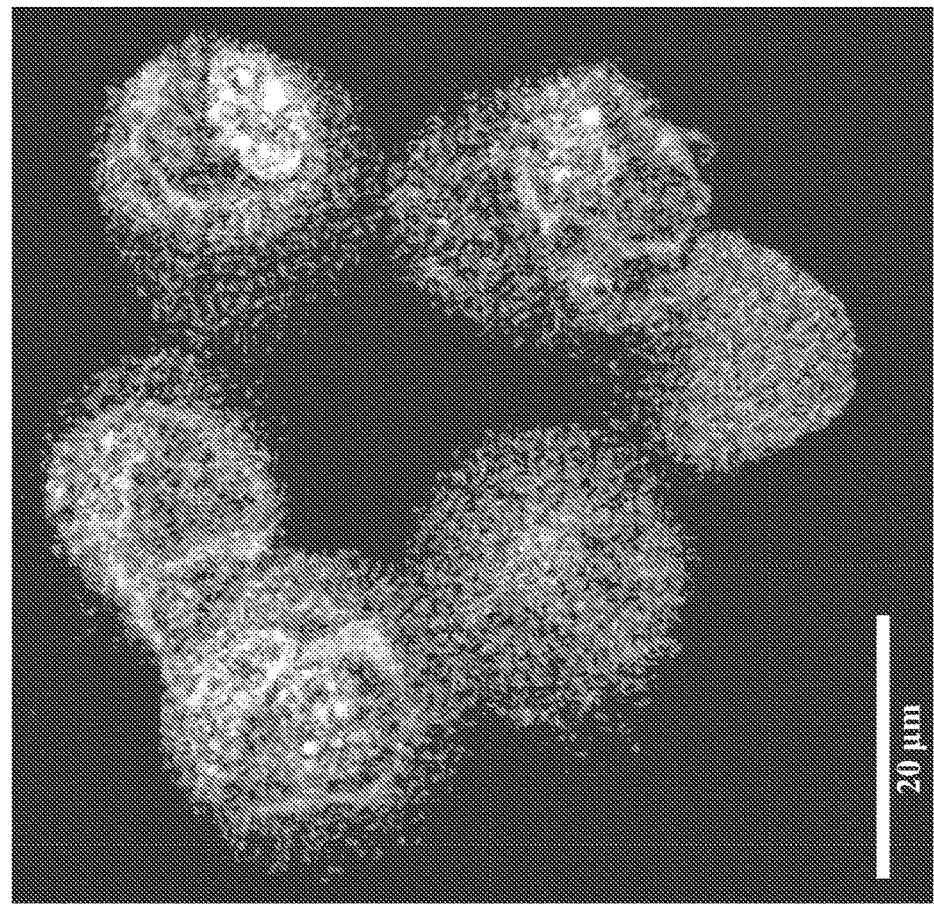
20 μm

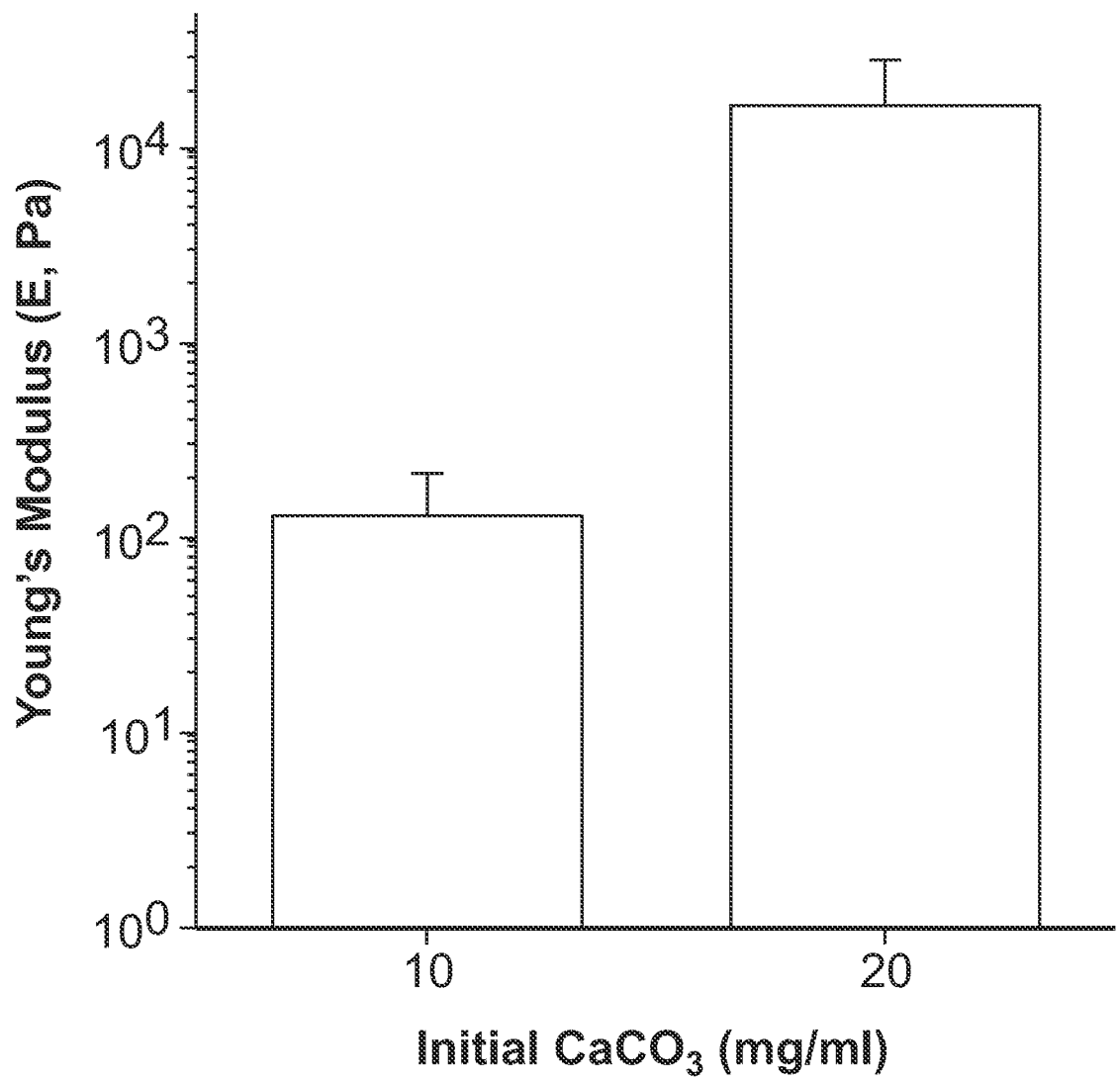

FIG. 5 (CONTINUED)
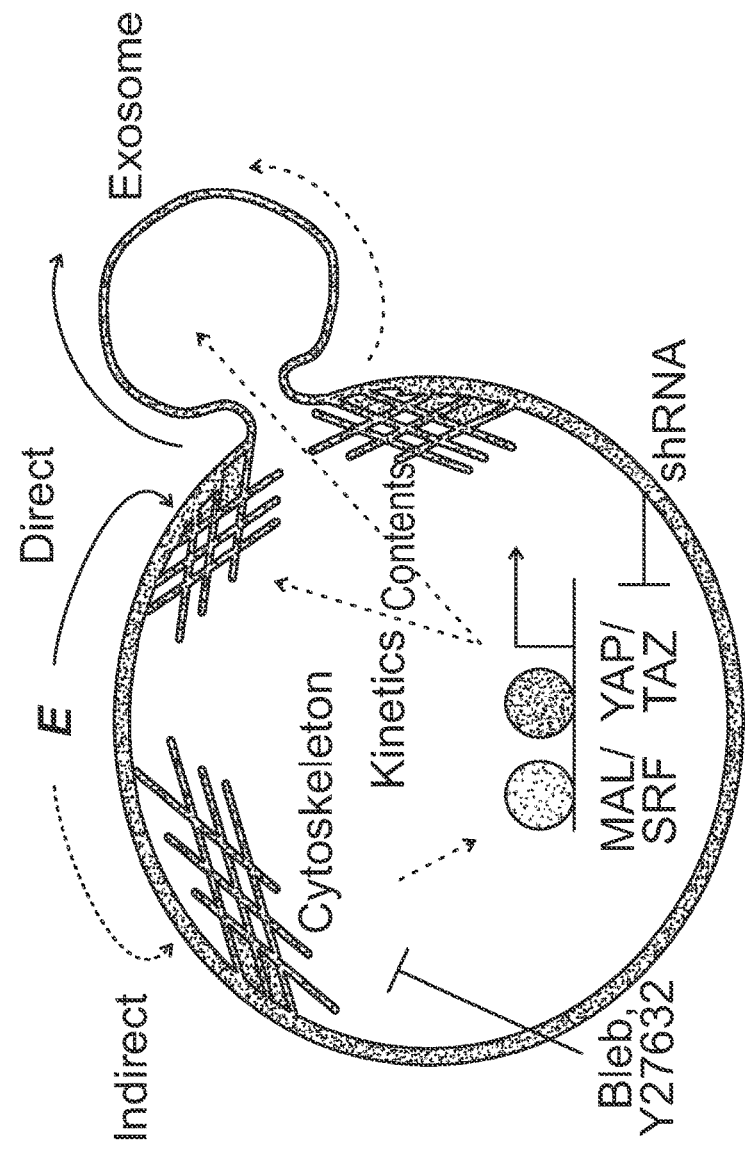

FIG. 7
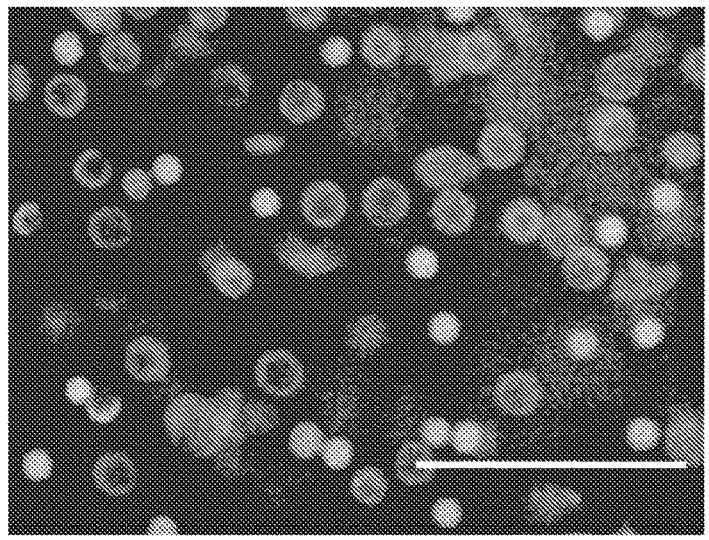
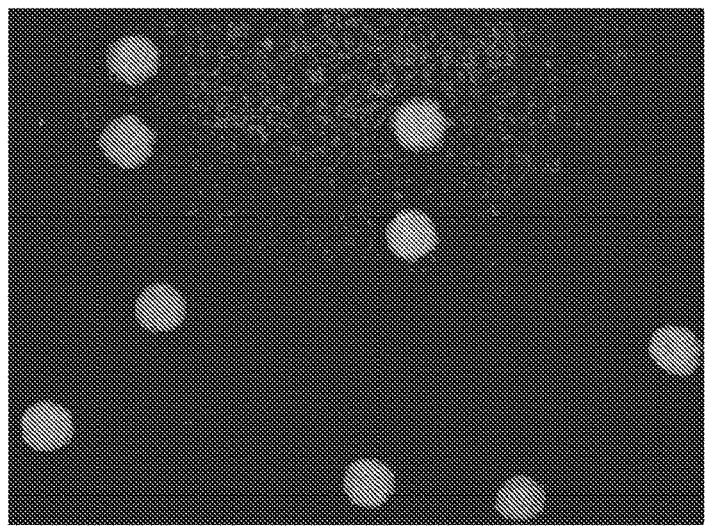
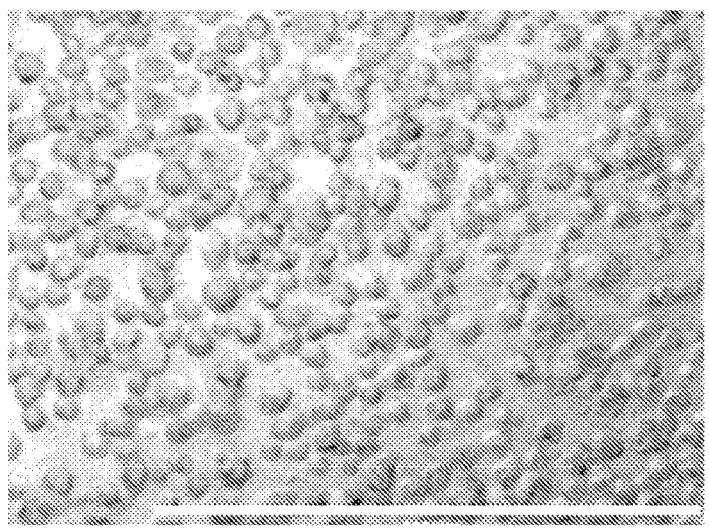

FIG. 7 (CONTINUED)
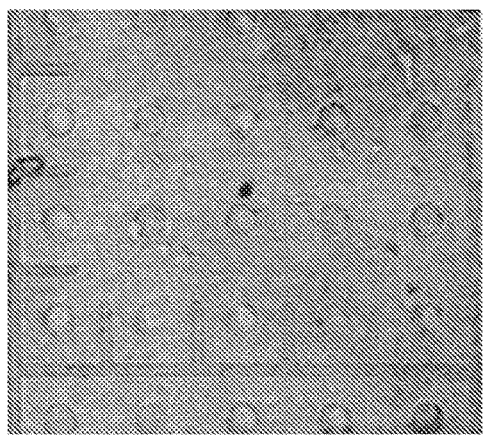
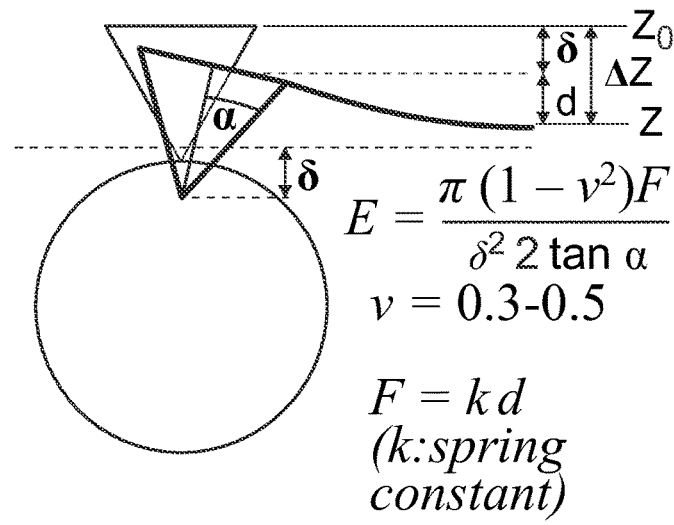
$$E = \frac{\pi(1-v^2)F}{\delta^2 \, 2 \tan \alpha}$$
$v = 0.3\text{-}0.5$
$F = kd$
($k$: spring constant)
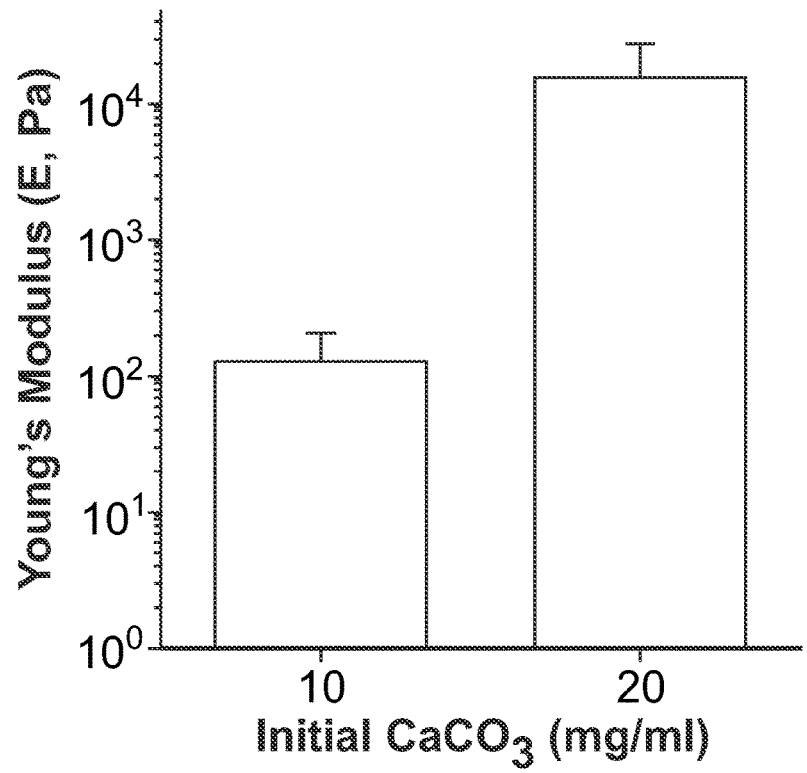
30 micron diameter, 1% alginate
Encapsulation efficiency = ~50%
Cell viability after encapsulation = ~50%

FIG. 10A
D1-Luciferase
20min
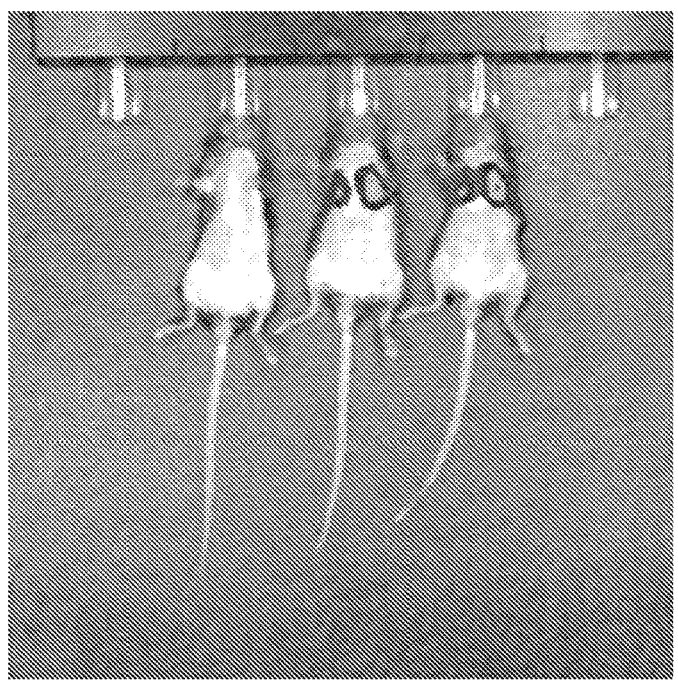
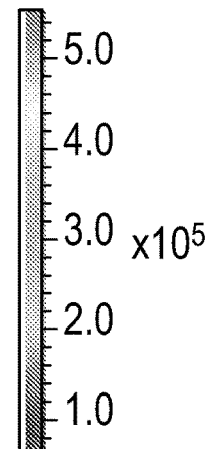
Luminescence
$5.0$
$4.0$
$3.0$ $\times 10^5$
$2.0$
$1.0$
Radiance
(p/sec/cm$^2$/sr)
Color Scale
Min = 3.29e4
Max = 5.55e5
24hr
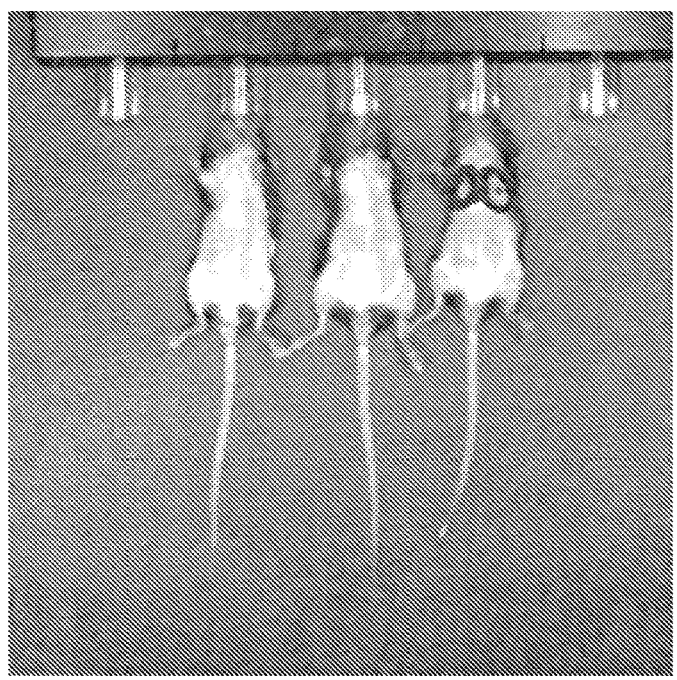
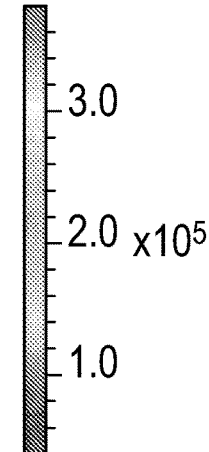
Luminescence
$3.0$
$2.0$ $\times 10^5$
$1.0$
Radiance
(p/sec/cm$^2$/sr)
Color Scale
Min = 2.26e4
Max = 3.78e5
PBS, MSC (100k), MSC in bead (100k)

FIG. 10A (CONTINUED)
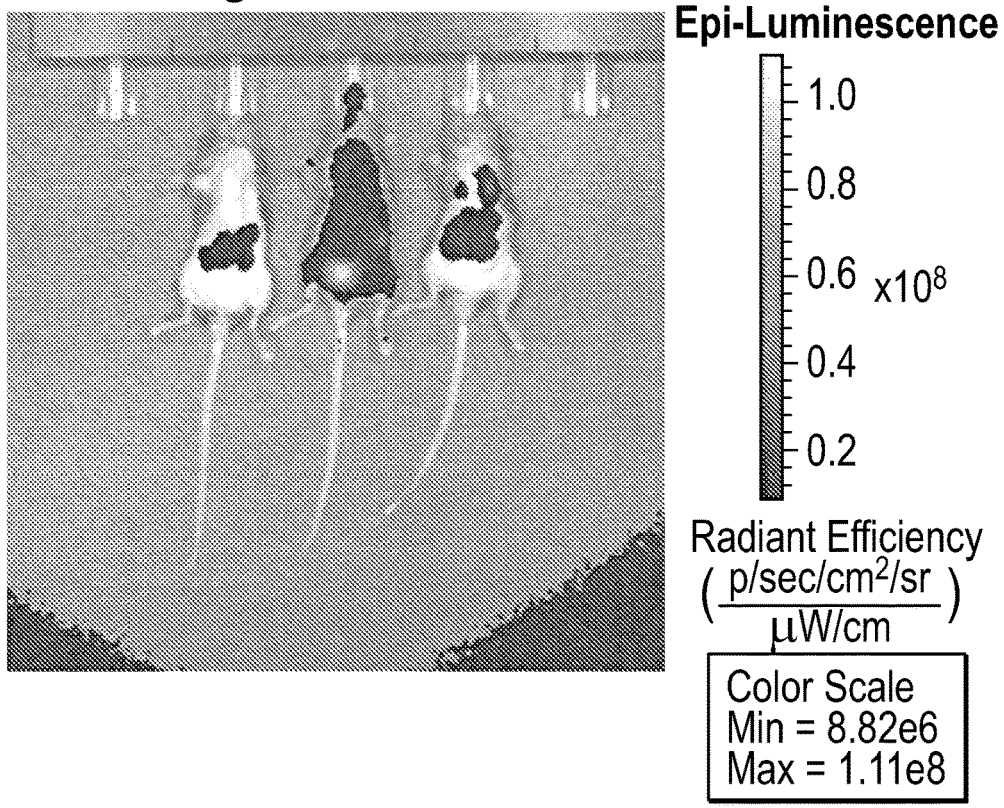
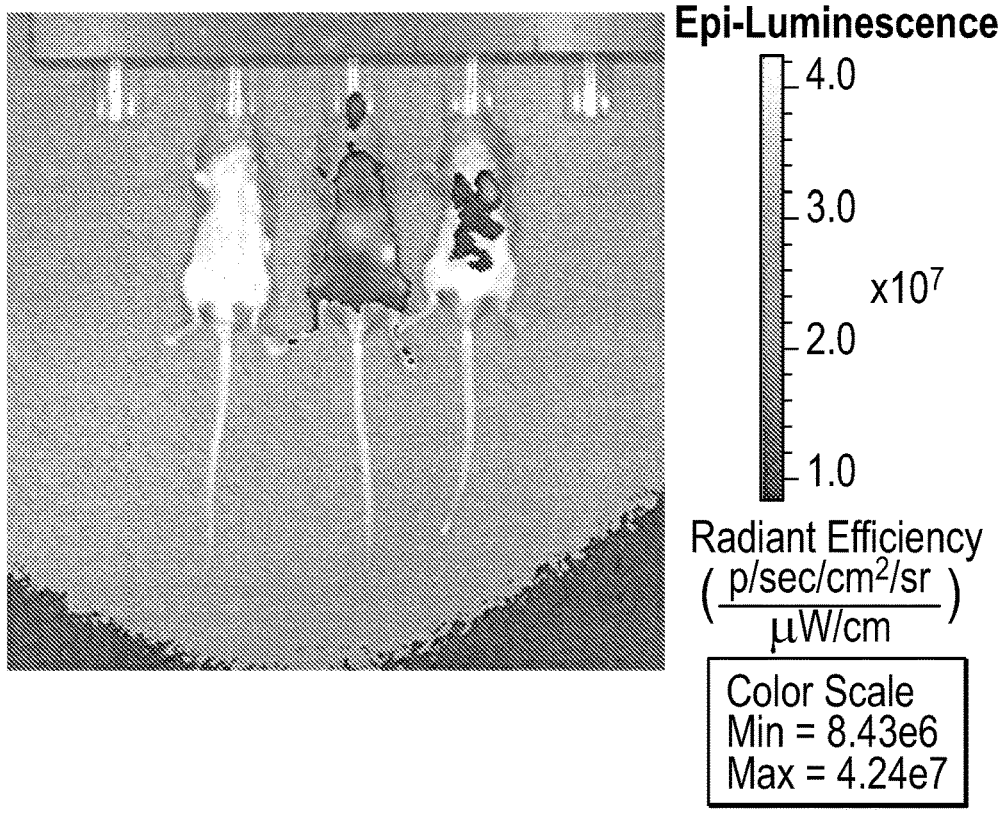

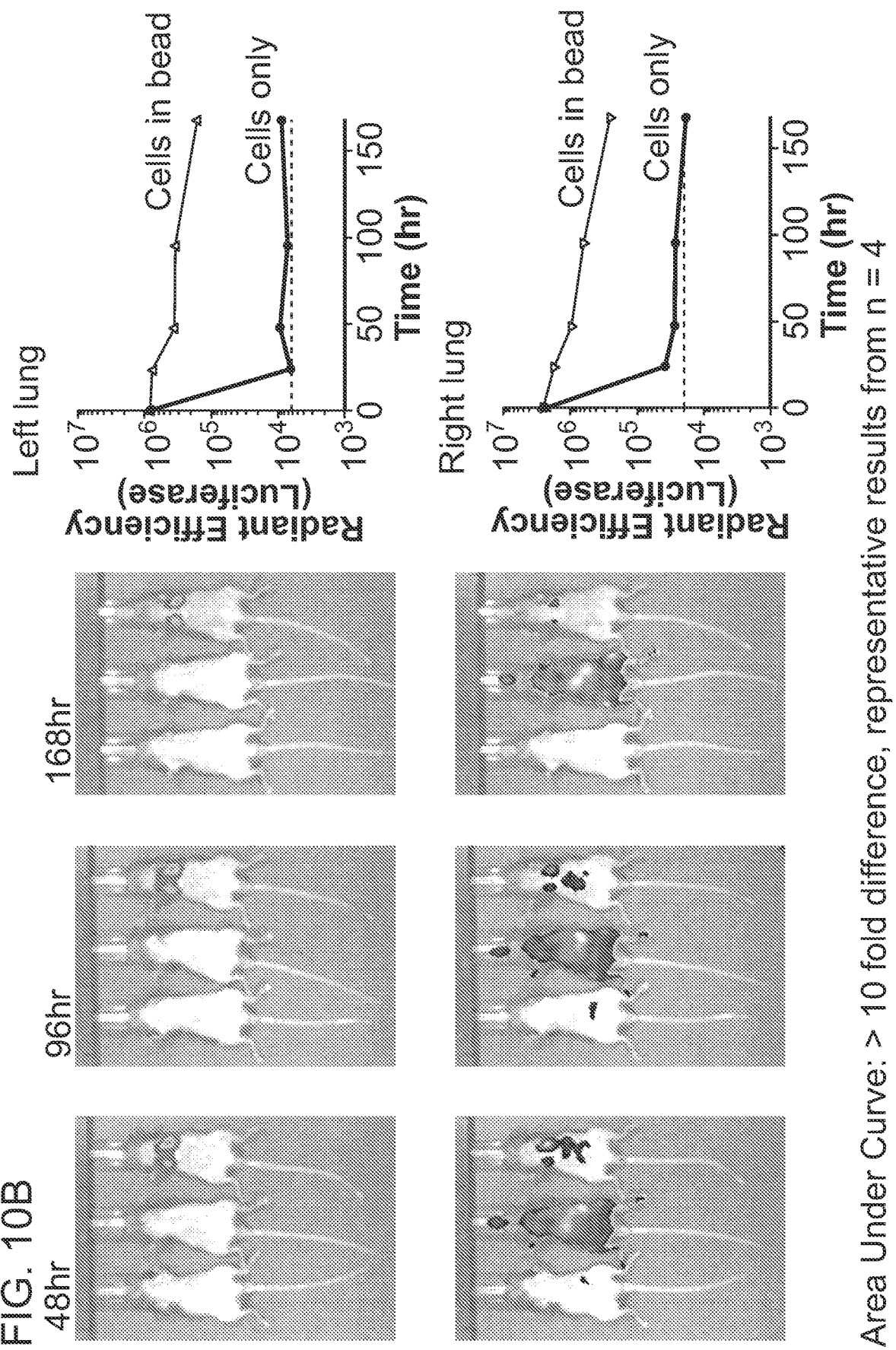

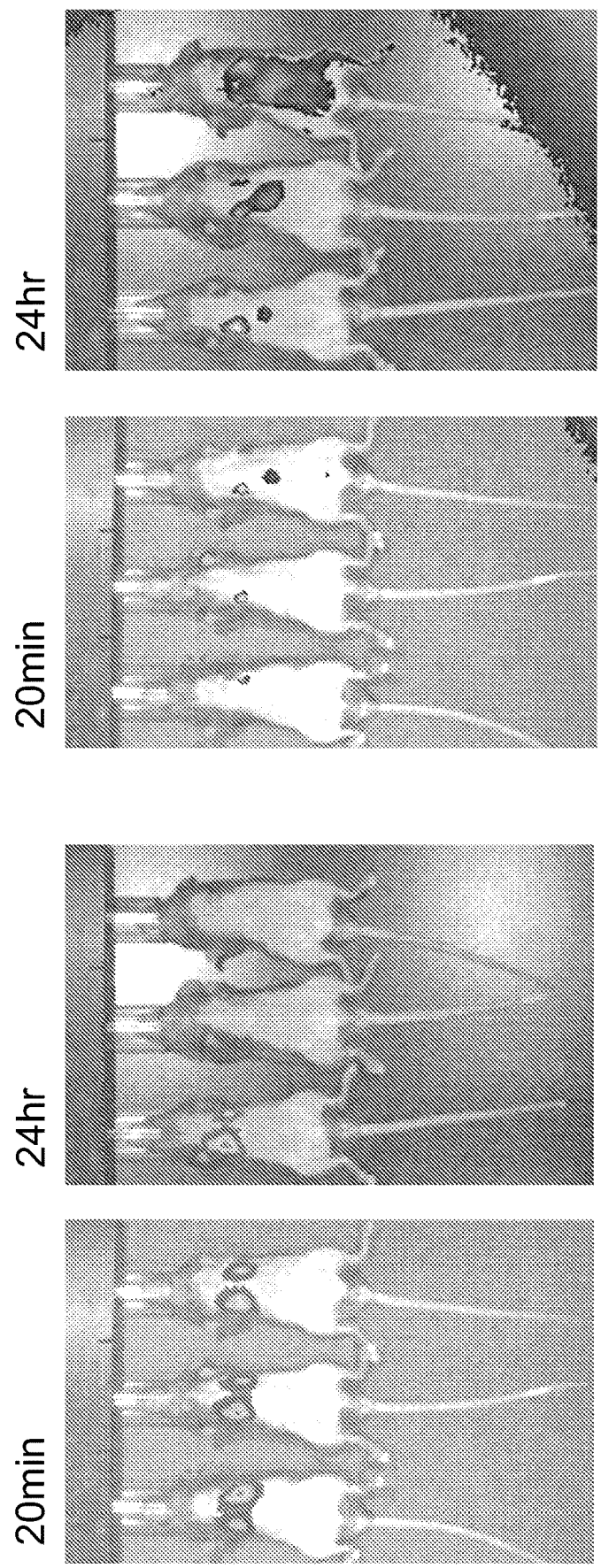

1: PBS
2: Beads injected into the left ventricle of the heart
3: Beads injected retroorbitally 100k and 10k = hMSCs without bead or alginate (n=1 each). 10K in bead = hMSCs in alginate bead conjugated with Alexa 750 (n=2 +/- SD). Dotted line = background signal. l = left lung, r = right lung FIG. 14
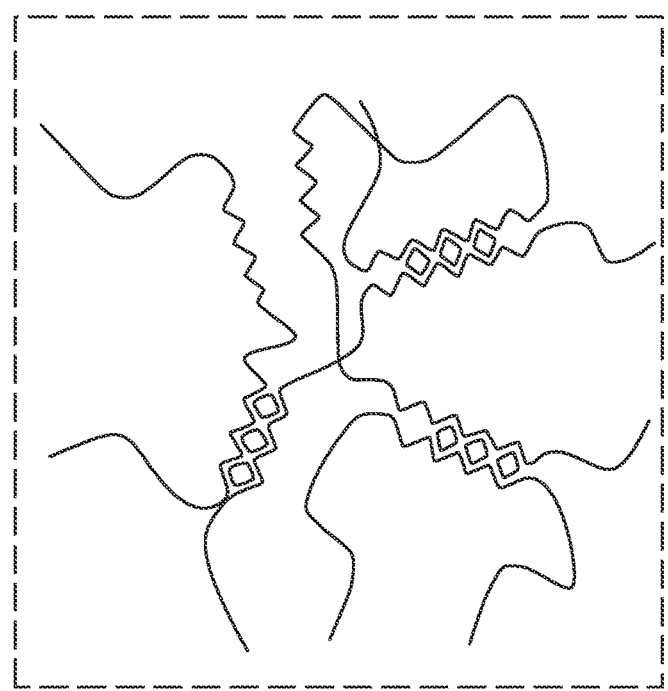
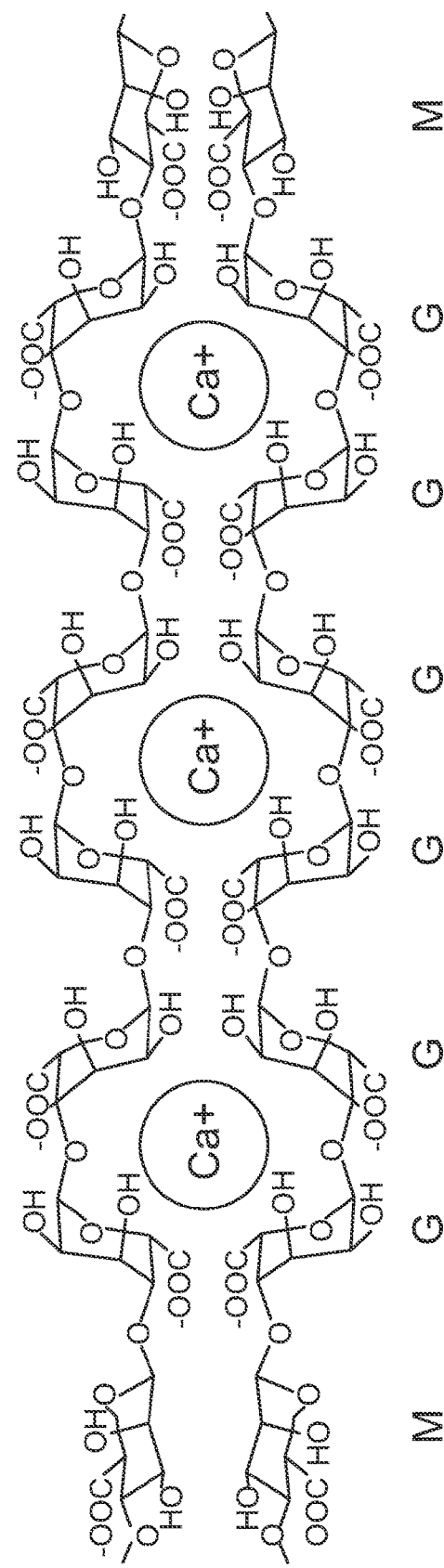

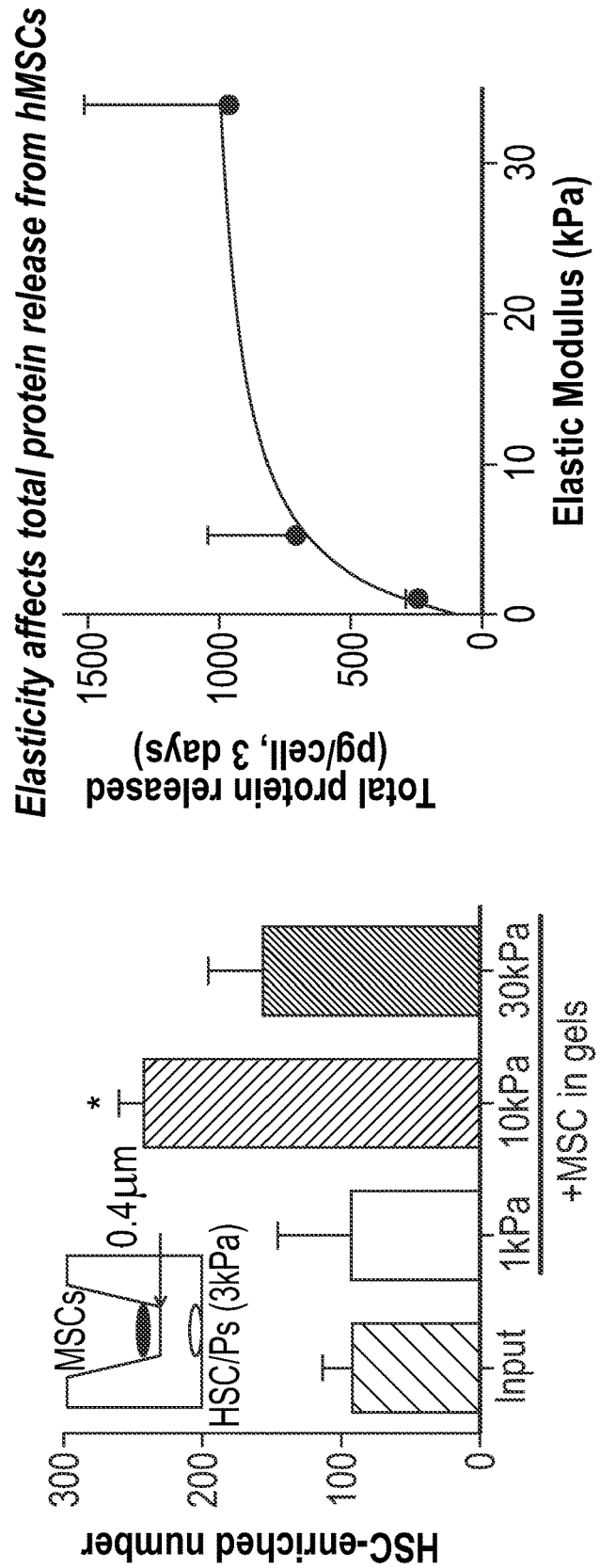
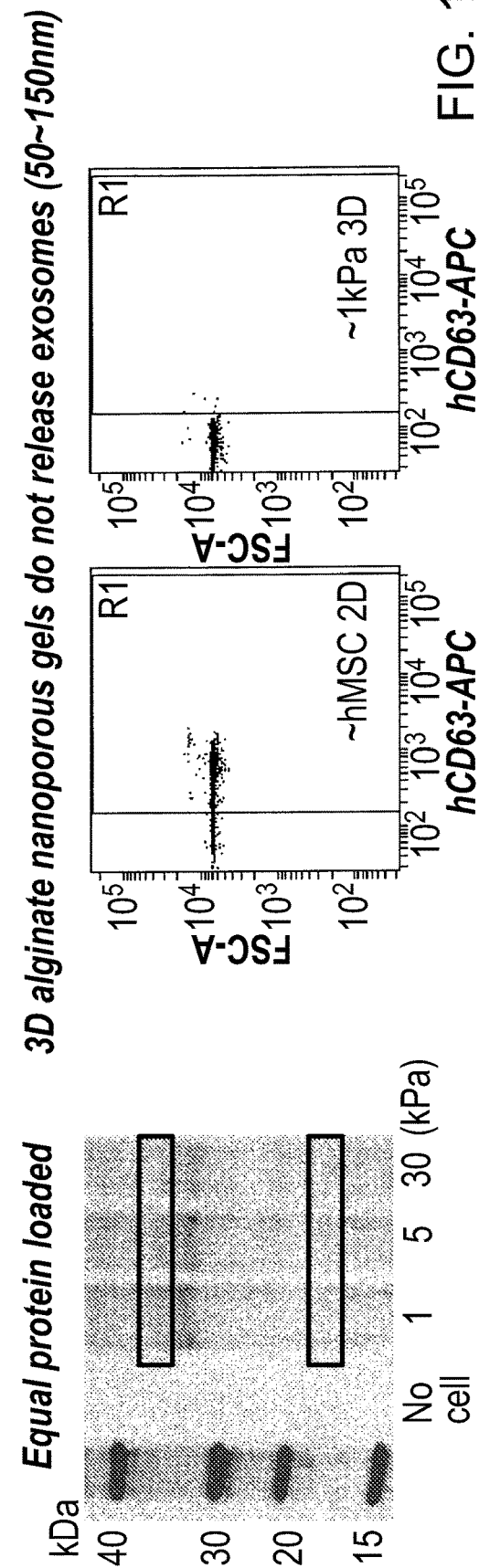
FIG. 15

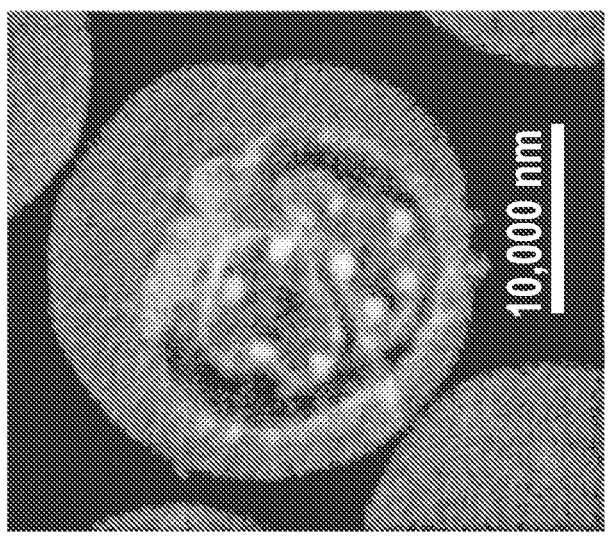
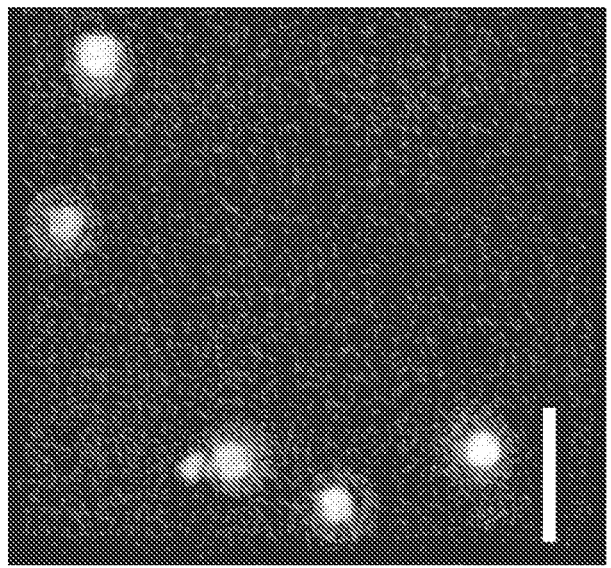
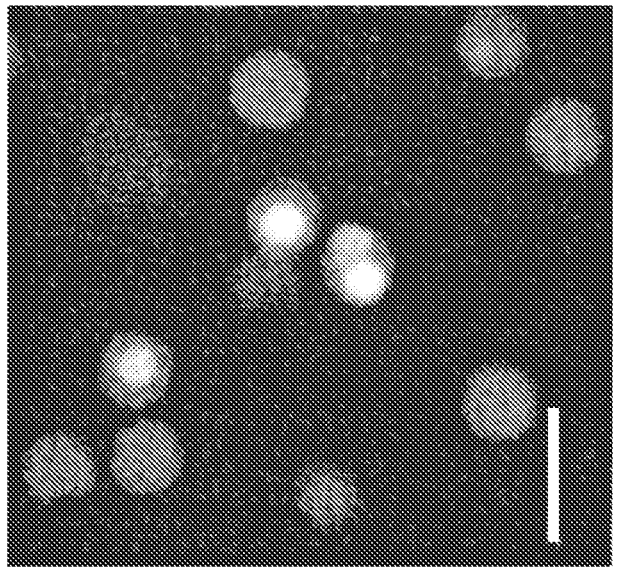
FIG. 17C
FIG. 17B
FIG. 17A

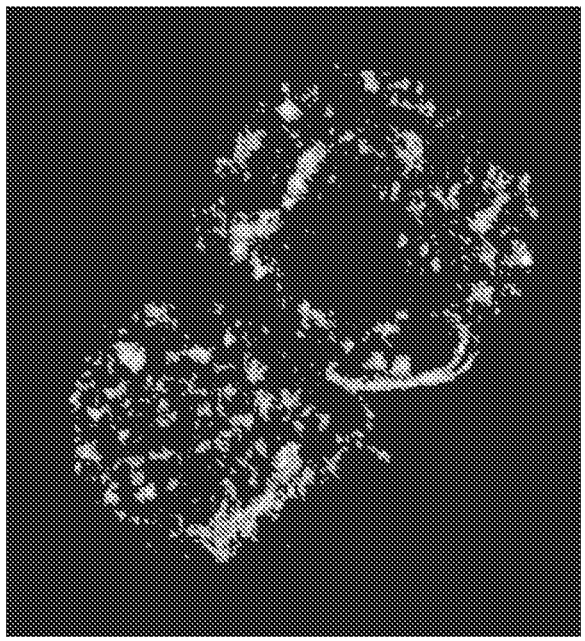 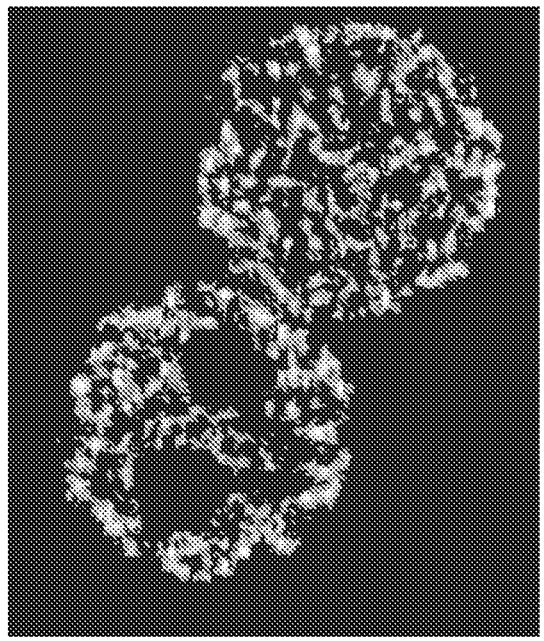
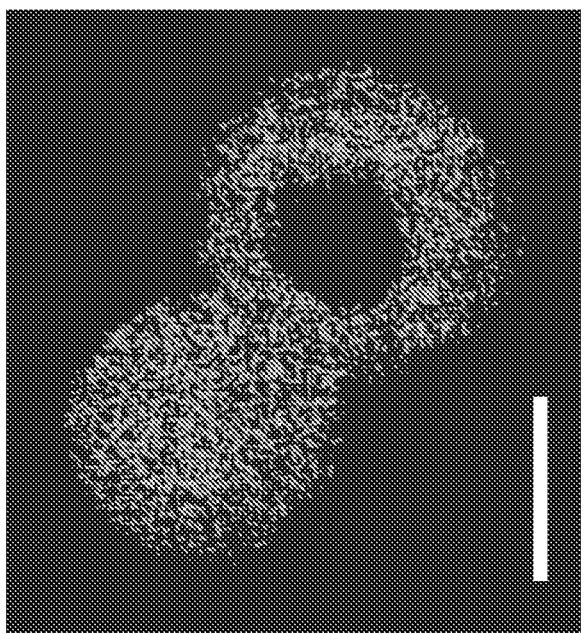 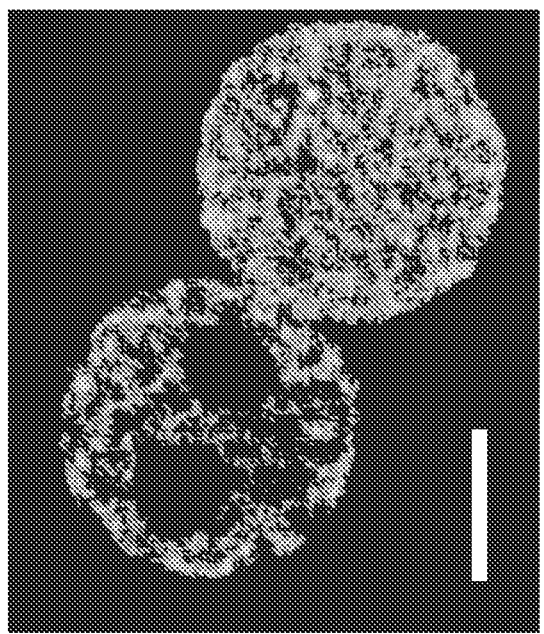
FIG. 19A
FIG. 19B

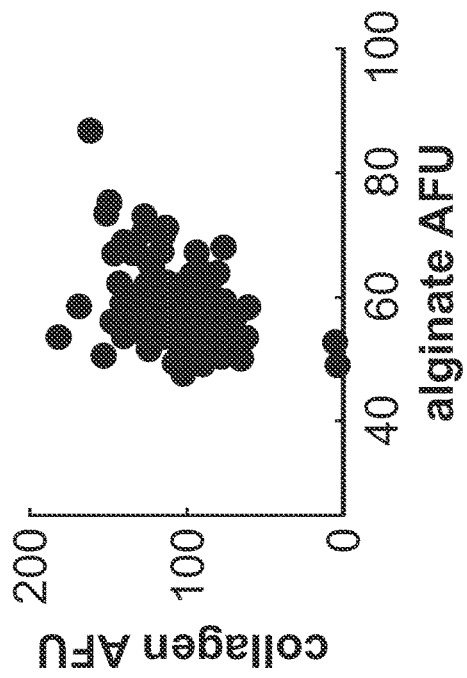
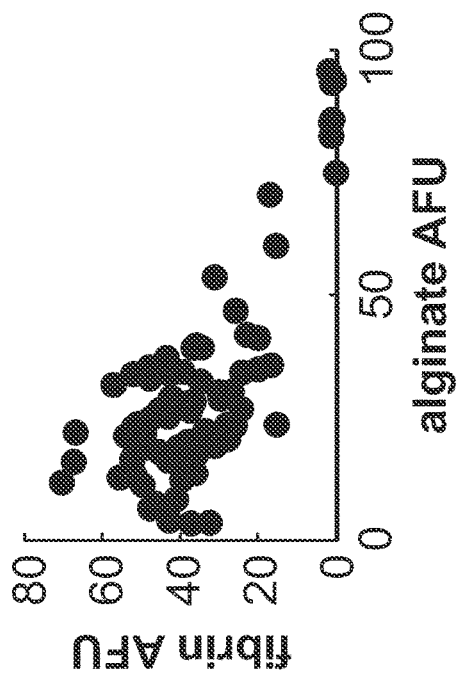
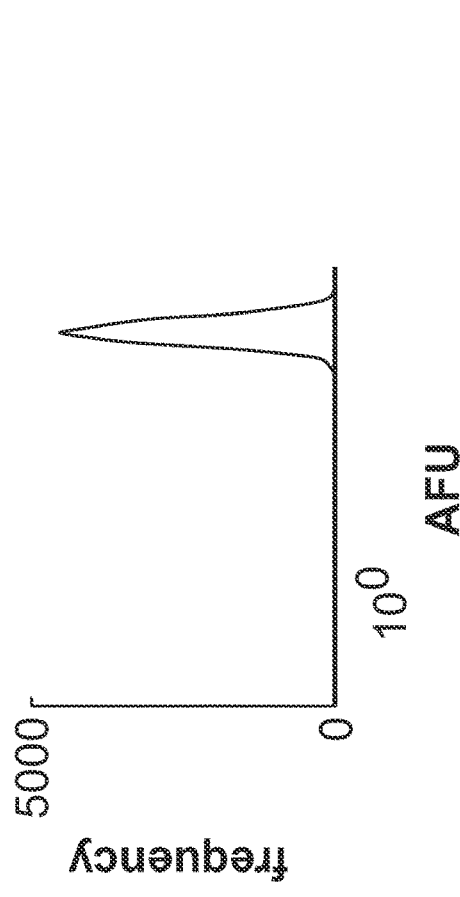
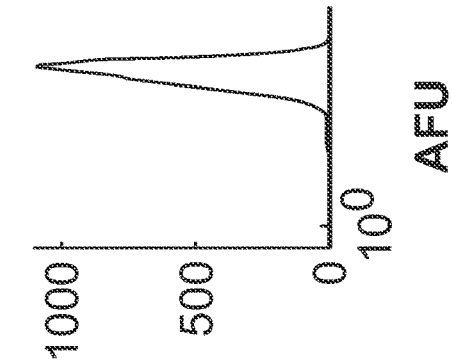
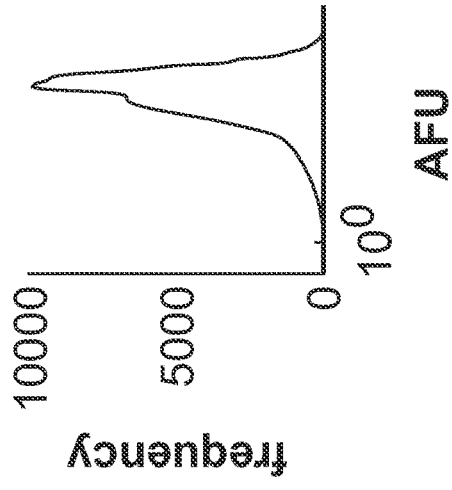

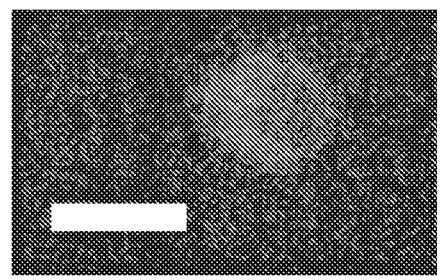
FIG. 19H
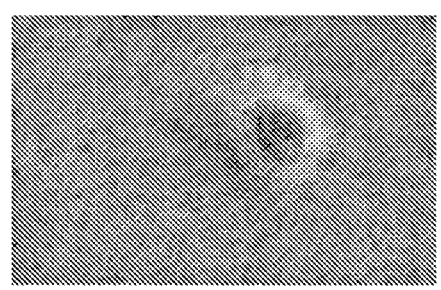
FIG. 19I
FIG. 19J
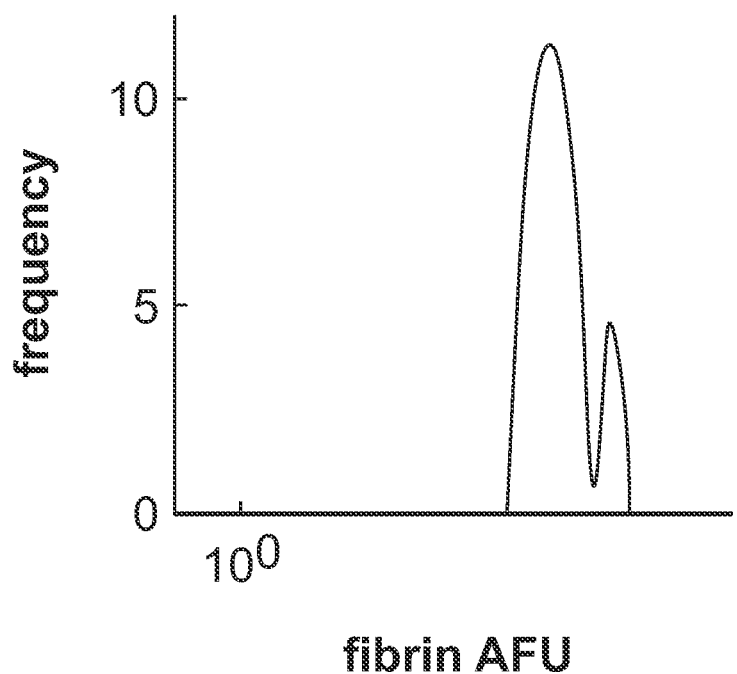

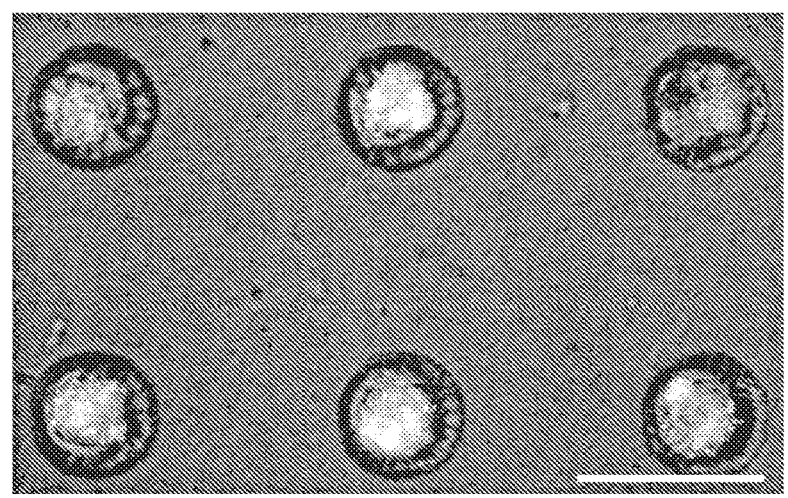
FIG. 20D
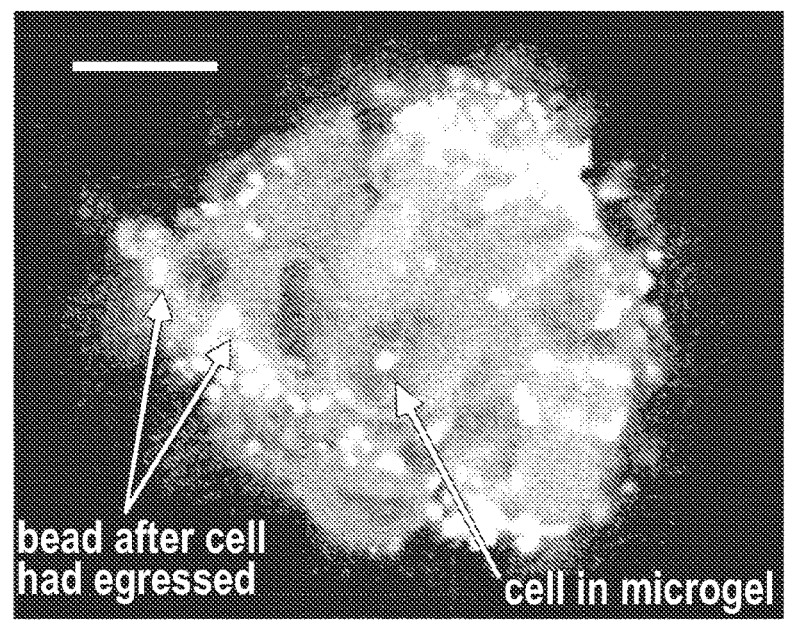
FIG. 20E
FIG. 20F
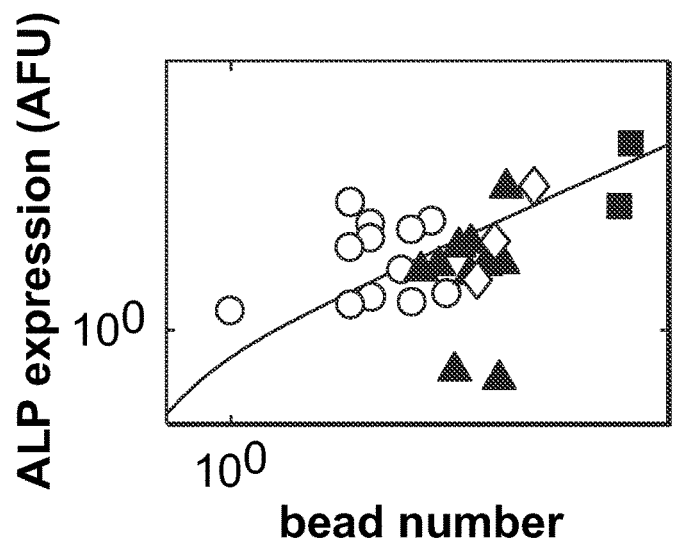

30

FIG. 25C
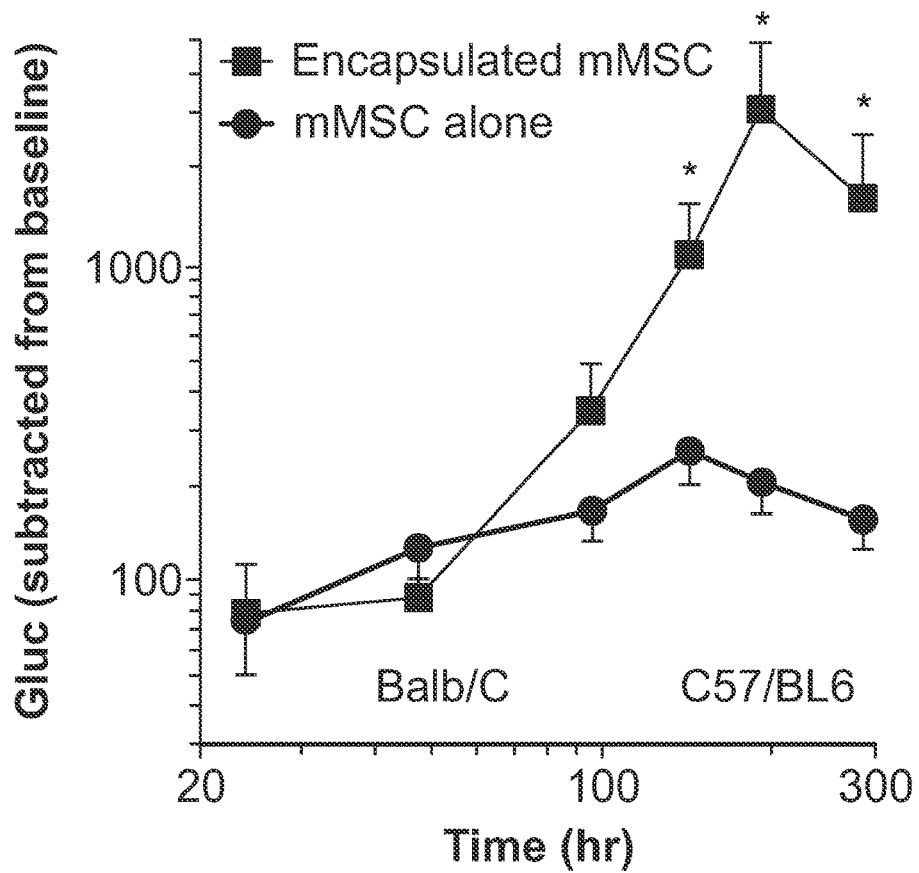
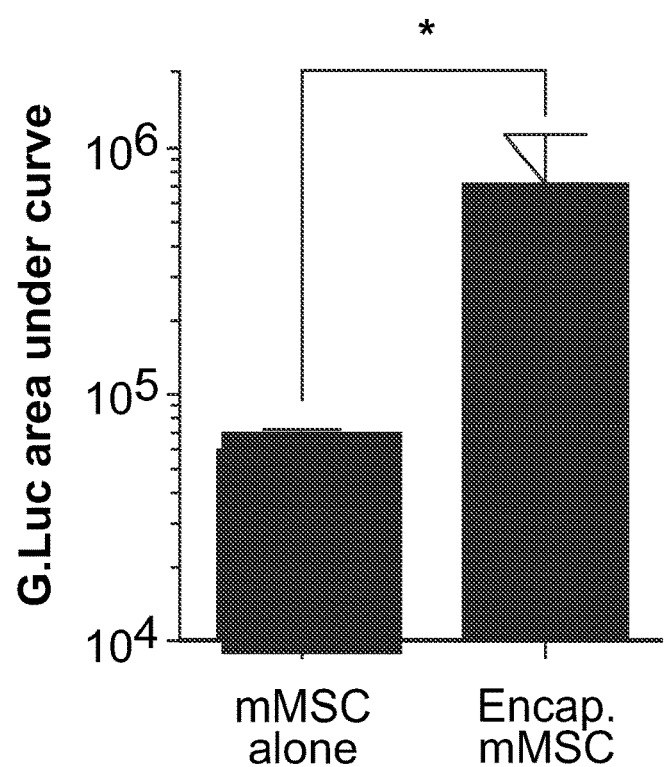

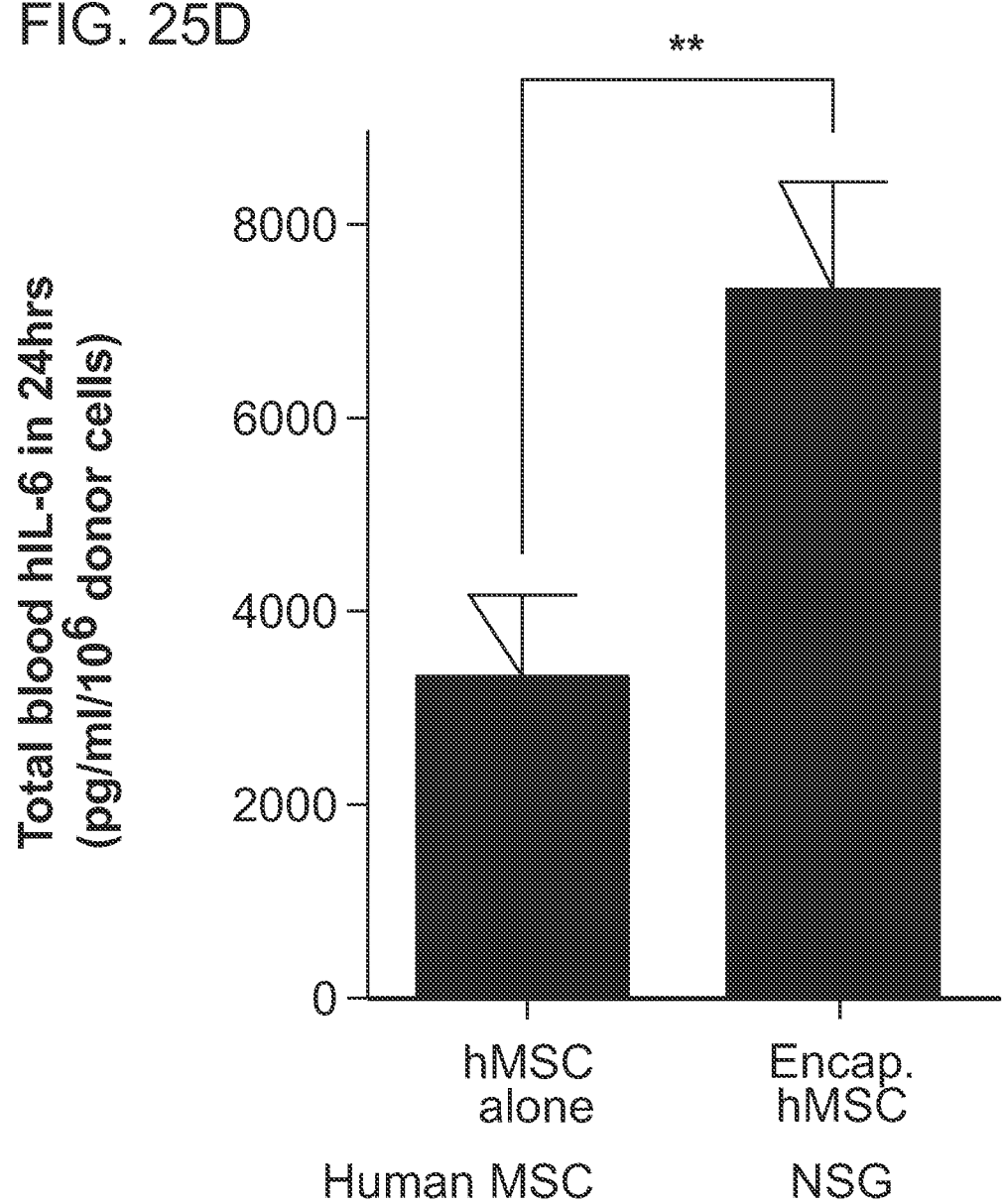

FIG. 26A Inflammatory factors e.g. IL6
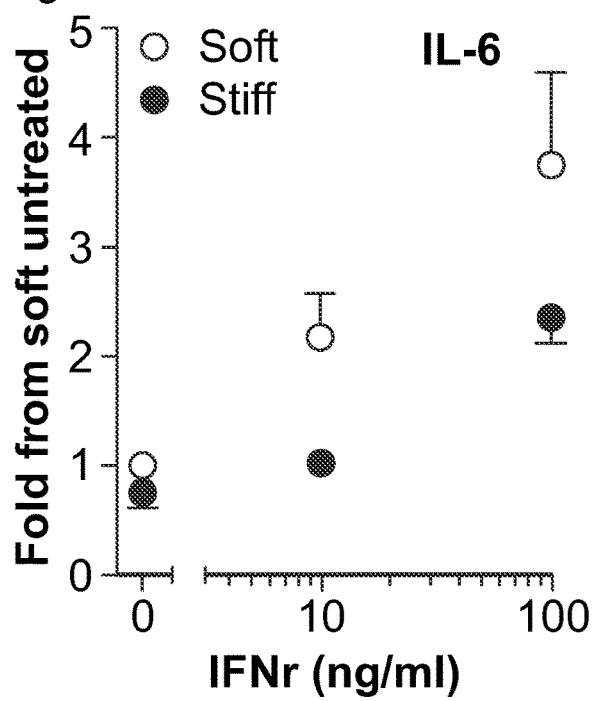
FIG. 26B
Chemokines e.g. MCP-1 (CCL2)
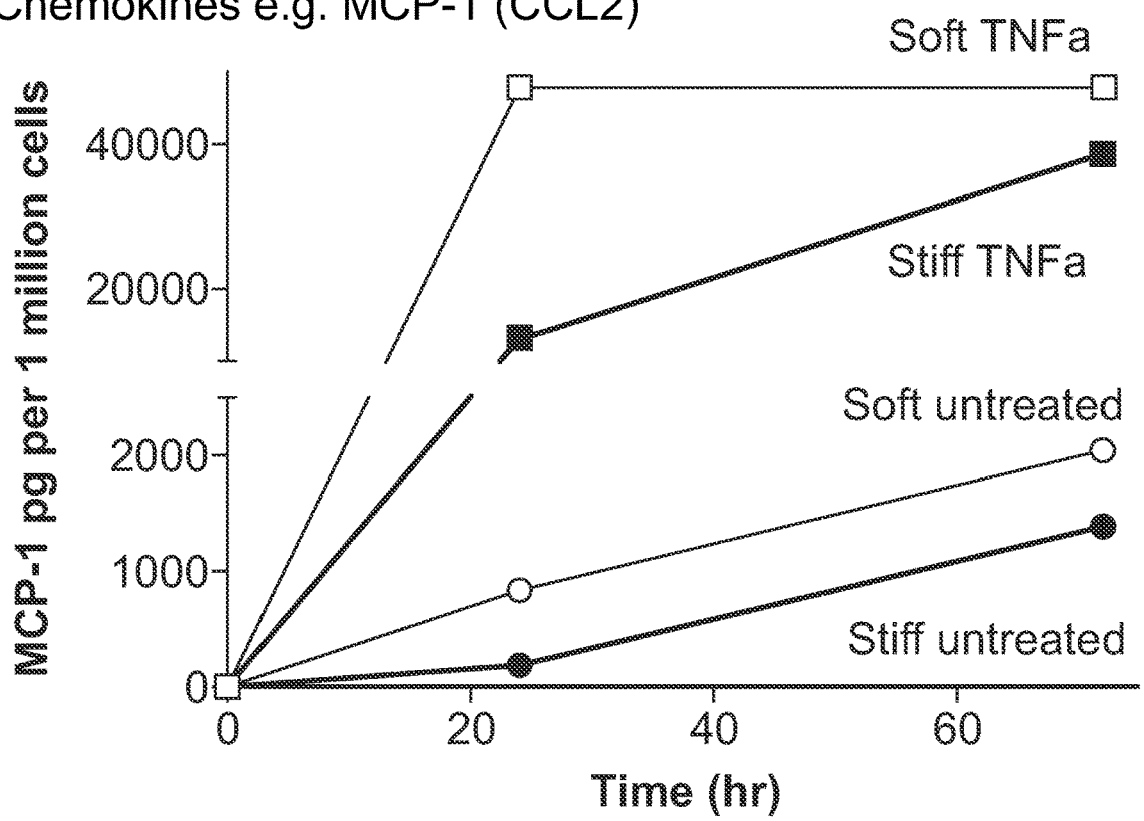

FIG. 26C
Hematopoietic factors e.g. SCF, TGFbeta
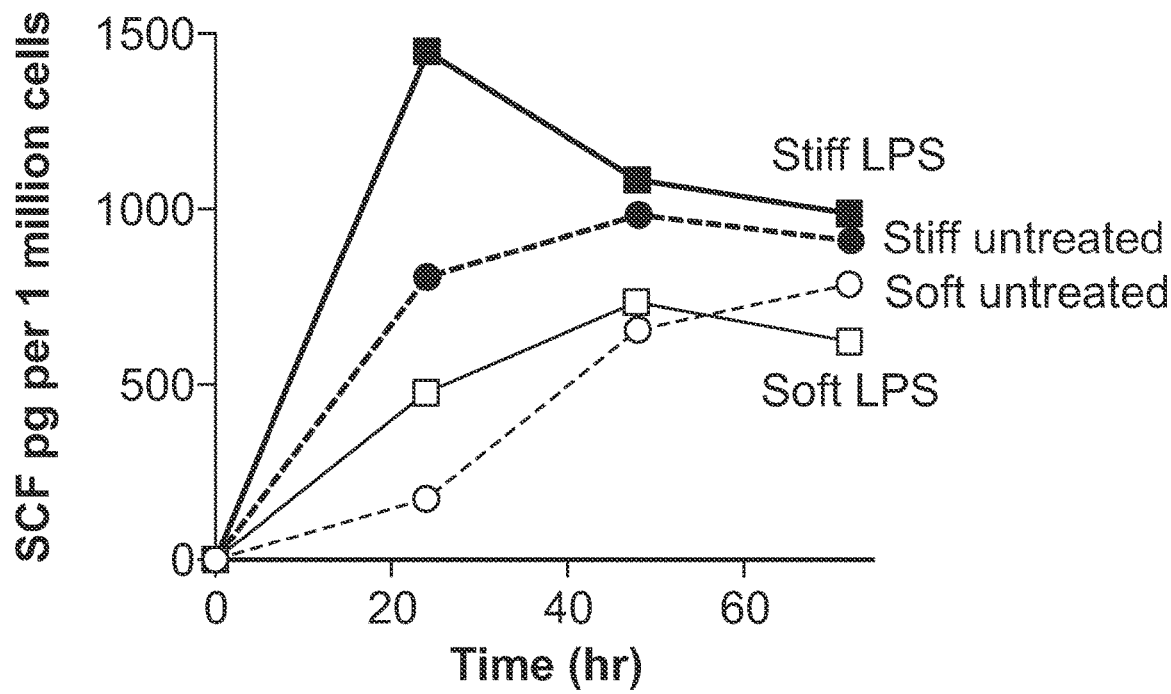
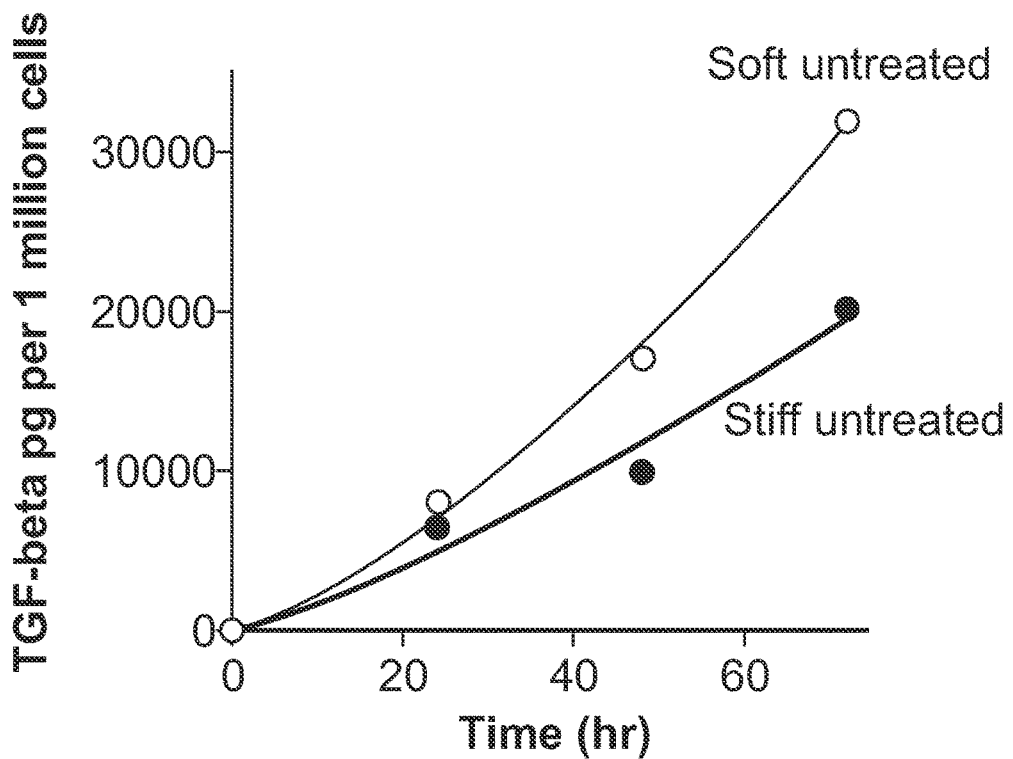

SEQUENCE LISTING

```
<160> NUMBER OF SEQ ID NOS: 13

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Gly Asp Ser
1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Glu Asp Val
1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Gly Asp Val
1

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Leu Arg Gly Asp Asn
1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ile Lys Val Ala Val
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
```

```
                                       peptide

<400> SEQUENCE: 6

Tyr Ile Gly Ser Arg
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Pro Asp Ser Gly Arg
1               5

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Asn Ile Ala Glu Ile Ile Lys Asp Ala
1               5                   10

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Gly Asp Thr
1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asp Gly Glu Ala
1

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 11

Val Thr Xaa Gly
```

```
<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Gly Gly Gly Arg Gly Asp Ser Pro
1               5

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Gly Gly Gly Arg Gly Ala Ser Ser Lys Tyr
1               5                   10
```

HYDROGEL COMPOSITIONS COMPRISING ENCAPSULATED CELLS AND METHODS OF USE THEREOF

RELATED APPLICATIONS

This application is a 35 U.S.C. § 371 national stage filing of International Application No. PCT/US2015/038601, filed on Jun. 30, 2015, which claims priority to U.S. Provisional Application No. 62/019,284, filed on Jun. 30, 2014 and U.S. Provisional Application No. 62/082,993, filed on Nov. 21, 2014. The entire contents of each of the foregoing applications are hereby incorporated herein by reference.

GOVERNMENT SUPPORT

The invention was supported, in whole, or in part, by a National Institutes of Health (NIH) R01 grant EB014703-03. The Government has certain rights in the invention.

FIELD OF INVENTION

The present invention relates to hydrogel compositions for cell delivery.

BACKGROUND OF THE INVENTION

Delivering cells and their secretions to the body remains a major challenge due to rapid clearance by physical and immune barriers. There is a need for methods to shield exogenously administered cells from the body's natural clearance mechanism. Such methods would significantly improve the in vivo delivery of biologics. While a bulk crosslinked hydrogel has been used for this purpose, it has been difficult to inject the bulk gel into the body, and the administration route has generally been limited to subcutaneous.

Hematopoiesis is the formation and development of blood cells. In embryos and fetuses, this process occurs in the liver, spleen, thymus, lymph nodes, and bone marrow. After birth, hematopoiesis occurs predominantly in the bone marrow. All blood cell types, including erythrocytes and cells of the myeloid and lymphoid lineages, are derived from multipotent hematopoietic stem cells (HSCs). Various factors regulate HSC regeneration and differentiation.

Bone marrow transplantation and HSC transplantation are used to treat a number of diseases, e.g., hematological diseases, immunodeficiencies, lysosomal storage disorders, and cancers. In addition, blood transfusions are in demand for patients who have undergone surgery, suffer from injuries, suffer from diseases such as cancer, or suffer from injuries in sports arenas or battlefields. There remains a need for methods of programming hematopoiesis ex vivo and in vivo, e.g., to sustain in vivo regeneration of blood or ex vivo production of blood. There is also a need for methods of preserving long-term self-renewal of HSCs in vivo, e.g., in diseased patients or patients who have undergone transplantation.

SUMMARY OF THE INVENTION

The invention addresses these needs by providing compositions that comprise capsules that comprise cross-linked hydrogels that encapsulate individual cells, e.g., mesenchymal stem cells (MSCs). The hydrogel encapsulated cells (also called hydrogel capsules, micro-carriers, microgels or microparticles) may be administered to a subject via a wide range of administration routes, e.g., by intravenous infusion or injection. The hydrogel encapsulated cells are also characterized by improved cell viability and are capable of sustained secretion of protein factors, such as factors that promote hematopoiesis, or factors that promote cardiovascular regeneration in a subject.

The present invention is based, at least in part, on a surprising discovery of a high-yield microfluidic technique to encapsulate single cells in hydrogel capsules with a thin layer of hydrogel. Specifically, it was discovered that contacting a cell with a moiety comprising a cross-linking catalyst and allowing such moiety to be adsorbed to the cell prior to hydrogel formation, results in a high yield of cell encapsulation, i.e., produces a composition with a high fraction of hydrogel capsules comprising a cell. Such compositions also have a low fraction of empty hydrogel capsules. This technique also allows for the production of compositions with a high fraction of hydrogel capsules comprising a single cell. Further, the thickness of the hydrogel layer in these hydrogel capsules comprising a cell is small, e.g., 20 microns or less. Accordingly, the mechanical properties and composition of the hydrogel coating can be tuned at the single cell-level to control biological functions of encapsulated cells in vitro and in vivo. A composition comprising a high fraction of singly encapsulated cells can be delivered in vivo via, for example, intravenous infusion. Such compositions also show prolonged biodistribution in vivo and secrete soluble protein factors that are useful for many indications.

The invention is also based, at least in part, on the discovery that release of protein factors from a hydrogel capsule comprising a cell can be regulated by altering the mechanical properties of the hydrogel layer. For example, it was discovered that stiffness of the hydrogel layer encapsulating a cell, e.g., a mesenchymal stem cell (MSC), regulates the release of protein factors produced by the cell, e.g., hematopoietic factors that regulate hematopoiesis and differentiation of hematopoietic stem cells (HSCs). Specifically, it was shown that stiffness of the hydrogel layer regulates exocytosis pathways in MSCs, e.g., exocytosis of factors, such as hematopoietic factors, from MSCs. The hydrogel capsules of the present invention mechanically trigger hematopoietic factor release from encapsulated cells, e.g., MSCs, in vivo.

Accordingly, in one aspect, the present invention provides a composition comprising a plurality of hydrogel capsules, wherein at least 90%, e.g., at least 91%, 92%, 93%, 94%, 95%, 96%, 97%, 98% or 99%, of the hydrogel capsules in the composition comprise a cell and a hydrogel encapsulating the cell, wherein the hydrogel encapsulating the cell has a thickness of less than 20 microns, e.g., less than 19, 18, 17, 16, 15, 14, 13, 12, 11, 10, 9, 8, 7, 6, 5, 4, 3, 2 or 1 microns.

In one embodiment, at least 70%, e.g., at least 75%, 80%, 85%, 90% or 95%, of the hydrogel capsules comprise a single cell.

In another embodiment, the cell is a mesenchymal stem cell (MSC) or a progenitor thereof, a hematopoietic stem cell (HSC) or a progenitor thereof, or an endothelial progenitor cell.

In some embodiments, the hydrogel comprises at least one polymer, e.g., a polymer selected from the group consisting of alginate, agarose, poly(ethylene glycol) dimethacrylate), polylactic acid, polyglycolic acid, PLGA, gelatin, collagen, agarose, pectin, poly(lysine), polyhydroxybutyrate, poly-epsilon-caprolactone, polyphosphazines, poly(vinyl alcohol), poly(alkylene oxide), poly(ethylene oxide), poly(allylamine), poly(acrylate), poly(4-aminomethylstyrene), pluronic polyol, polyoxamer, poly(uronic acid), poly(anhydride) and poly(vinylpyrrolidone). In a specific embodiment, the polymer is alginate.

In a further embodiment, the polymer comprises polymer chains cross-linked to each other using a divalent or trivalent cation, e.g., $Ca^{2+}$, $Mg^{2+}$, $Sr^{2+}$, $Ba^{2+}$, $Be^{2+}$ and $Al^{3+}$. In a specific embodiment, the divalent cation is $Ca^{2+}$.

In certain embodiments, the diameter of the hydrogel capsule comprising a single cell is between about 10 and 500 micron, e.g., between about 10 and about 200 micron, about 50 micron and about 300 micron, about 250 and about 500 micron, about 20 and about 80 micron, about 100 and about 400 micron, about 250 and about 450 micron and about 30 to about 150 micron. In a further embodiment, the diameter of the hydrogel capsule comprising a single cell is between about 25 and about 30 micron, e.g., about 25 and about 27 micron, about 26 and about 29 micron, about 27 and about 30 micron.

In one embodiment, the hydrogel comprises a first polymer and a second polymer. In a specific embodiment, the first polymer is alginate and the second polymer is collagen or fibrin.

In another aspect, the present invention also provides a method of preparing a composition comprising a plurality of hydrogel capsules. The method includes: a) contacting a cell with a moiety capable of adhering to a cell and comprising a cross-linking catalyst; and b) contacting the cell and the moiety with at least one polymer comprising a plurality of polymer chains; wherein the cross-linking catalyst catalyzes a reaction that cross-links the plurality of polymer chains, thereby forming a composition comprising a plurality of hydrogel capsules, wherein at least 90% of the hydrogel capsules in the composition comprise a cell and a hydrogel encapsulating the cell, wherein the hydrogel encapsulating the cell has a thickness of less than 20 microns.

In one embodiment, the cross-linking catalyst is a divalent or trivalent cation. In one embodiment, the divalent or trivalent cation is selected from the group consisting of $Ca^{2+}$, $Mg^{2+}$, $Sr^{2+}$, $Ba^{2+}$, $Be^{2+}$ and $Al^{3+}$. In a further embodiment, the moiety is a nanoparticle, e.g., a $CaCO_3$ nanoparticle, a $BaCO_3$ nanoparticle, or a $SrCO_3$ nanoparticle.

In some embodiments, at least one polymer is selected from the group consisting of alginate, agarose, poly(ethylene glycol dimethacrylate), polylactic acid, polyglycolic acid, PLGA, gelatin, collagen, agarose, pectin, poly(lysine), polyhydroxybutyrate, poly-epsilon-caprolactone, polyphosphazines, poly(vinyl alcohol), poly(alkylene oxide), poly(ethylene oxide), poly(allylamine), poly(acrylate), poly(4-aminomethylstyrene), pluronic polyol, polyoxamer, poly(uronic acid), poly(anhydride) and poly(vinylpyrrolidone). In a further aspect, the at least one polymer is alginate.

In some embodiments, the cell is a mesenchymal stem cell (MSC) or a progenitor thereof, a hematopoietic stem cell (HSC) or a progenitor thereof, or an endothelial progenitor cell. In a specific embodiment, the mesenchymal stem cell (MSC) or a progenitor thereof.

In a further aspect, the present invention also provides a method of administering at least one protein factor produced by a cell to a subject in need thereof. The method includes administering to the subject a composition comprising a plurality of hydrogel capsules, wherein at least 90%, e.g., at least 91%, 92%, 93%, 94%, 95%, 96%, 97%, 98% or 99%, of said hydrogel capsules in the composition comprise a cell and a hydrogel encapsulating the cell, wherein the hydrogel encapsulating the cell has a thickness of less than 20 microns, e.g., less than 19, 18, 17, 16, 15, 14, 13, 12, 11, 10, 9, 8, 7, 6, 5, 4, 3, 2 or 1 microns.

In one embodiment, the cell is a mesencymal stem cell (MSC) or a progenitor thereof.

In another embodiment, the hydrogel in each cell containing hydrogel capsule is characterized by a stiffness of about 0.1 to about 500 kPa, e.g., about 0.1 to about 10 kPa, about 0.5 to about 15 kPa, about 1 to about 15 kPa, about 5 to about 20 kPa, about 10 to about 50 kPa, about 20 to about 100 kPa, about 150 to about 300 kPa, about 100 to about 400 kPa, about 200 to about 450 kPa or about 250 to about 500 kPa. In a further aspect, each cell containing hydrogel capsule is characterized by a stiffness of about 10 kPa, about 15 kPa, about 20 kPa, about 25 kPa, about 30 kPa, about 35 kPa, about 40 kPa, about 45 kPa, about 50 kPa, about 55 kPa, about 60 kPa, about 65 kPa, about 70 kPa, about 75 kPa, about 80 kPa, about 85 kPa, about 90 kPa, about 95 kPa or about 100 kPa.

In one embodiment, at least one protein factor is naturally produced by the cell. In another embodiment, the at least one protein factor is not naturally produced by the cell and the cell has been genetically engineered to produce the at least one protein factor. In yet another embodiment, the cell has been genetically engineered to modify expression of at least one protein factor. In a further aspect, the at least one protein factor is a hematopoietic factor.

In some embodiments, the hematopoietic factor is selected from the group consisting of stem cell factor (SCF), interleukin-2 (IL-2), interleukin-3 (IL-3), interleukin-6 (IL-6), interleukin-7 (IL-7), granulocyte-macrophage colony stimulating factor (GM-CSF), granulocyte colony stimulating factor (G-CSF), macrophage colony stimulating factor (M-CSF), erythropoietin, thrombopoietin, collagen-I, interleukin-11 (IL-11), angiopoietin-1 and transforming growth factor-beta (TGF-beta). In a specific aspect, the subject is a human.

In one embodiment, the number of hematopoietic stem cells (HSCs) in the subject is increased.

In some embodiments, the composition is administered by a route selected from the group consisting of intravenous infusion, intrabone infusion, intramuscular injection, subcutaneous implantation, intraperitoneal injection, intracardial injection, intratracheal administration, topical application and oral administration. In a specific embodiment, the composition is administered by intravenous infusion.

In some embodiments, the subject has undergone bone marrow transplantation or HSC transplantation. In other embodiments, the subject suffers from cancer, an immune deficiency disorder, or a blood disease. In a further embodiment, the cancer is a blood cancer or a solid tumor cancer. In another embodiment, the blood cancer is leukemia, lymphoma or myeloma. In yet another embodiment, the solid tumor cancer is selected from the group consisting of an adrenocortical tumor, colorectal carcinoma, breast cancer, lung cancer, ovarian cancer, uterine cancer, endometrial cancer, cervical cancer, gliobastoma, colon cancer, stomach cancer, pancreatic cancer, desmoid tumor, desmoplastic small round cell tumor, endocrine tumor, Ewing sarcoma, hepatocellular carcinoma, melanoma, neuroblastoma, osteosarcoma, retinoblastoma, rhabdomyosarcoma, Wilms tumor, nasopharyngeal cancer, testicular cancer, thyroid cancer, thymus cancer, gallbladder cancer, central nervous system (CNS) cancer, bladder cancer and bile duct cancer.

In another aspect, the blood disease is a disease selected from the group consisting of thalassemia, aplastic anemia and sickle cell anemia. In other embodiments, the immune deficiency disorder is a disorder selected from the group consisting of X-linked agammaglobulinemia (XLA), severe combined immunodeficiency (SCID disorder), common variable immunodeficiency and alymphocytosis.

In another aspect, the present invention provides a method for treating or preventing a cardiovascular disease in a subject in need thereof. The method includes administering to the subject a composition comprising a plurality of hydrogel capsules, wherein at least 90%, e.g., at least 91%, 92%, 93%, 94%, 95%, 96%, 97%, 98% or 99%, of said hydrogel capsules in the composition comprise a cell and a hydrogel encapsulating the cell, wherein the hydrogel encapsulating the cell has a thickness of less than 20 microns, e.g., less than 19, 18, 17, 16, 15, 14, 13, 12, 11, 10, 9, 8, 7, 6, 5, 4, 3, 2 or 1 microns.

In some embodiments, the cardiovascular disease is selected from the group consisting of coronary artery disease, cardiomyopathy, hypertensive heart disease, heart failure, cor pulmonale, cardiac dysrhythmia, indocarditis, inflammatory cardiomegaly, myocarditis, valvular heart disease, cerebrovascular disease, peripheral arterial disease, congenital heart disease and rheumatic heart disease.

In certain embodiments, the composition is administered by a route selected from the group consisting of intravenous infusion, intrabone infusion, intramuscular injection, subcutaneous implantation, intraperitoneal injection, intracardial injection, intratracheal administration, topical application and oral administration. In a specific embodiment, the composition is administered by intravenous infusion.

In another aspect, the present invention also provides a method of increasing secretion of a protein factor by a cell. The method includes a) contacting the cell with a moiety capable of adhering to a cell and comprising a cross-linking catalyst; and b) contacting the cell and the moiety with at least one polymer comprising a plurality of polymer chains; wherein the cross-linking catalyst catalyzes a reaction that cross-links said plurality of polymer chains, thereby forming a composition comprising a plurality of hydrogel capsules, wherein at least 90%, e.g., at least 91%, 92%, 93%, 94%, 95%, 96%, 97%, 98% or 99%, of the hydrogel capsules in the composition comprise a cell and a hydrogel encapsulating the cell, wherein the hydrogel encapsulating the cell has a thickness of less than 20 microns, e.g., less than 19, 18, 17, 16, 15, 14, 13, 12, 11, 10, 9, 8, 7, 6, 5, 4, 3, 2 or 1 microns, and wherein the encapsulation of the cell causes an increase in the secretion of a protein factor by the cell.

In some embodiments, the cell is a mesenchymal stem cell (MSC).

In some embodiments, the protein factor is a hematopoietic factor. In a further embodiment, the hematopoietic factor is selected from the group consisting of stem cell factor (SCF), interleukin-2 (IL-2), interleukin-3 (IL-3), interleukin-6 (IL-6), interleukin-7 (IL-7), granulocyte-macrophage colony stimulating factor (GM-CSF), granulocyte colony stimulating factor (G-CSF), macrophage colony stimulating factor (M-CSF), erythropoietin, thrombopoietin, collagen-I, interleukin-11 (IL-11), angiopoietin-1, and transforming growth factor-beta (TGF-beta).

In other embodiments, the hydrogel is characterized by a stiffness of about 0.1 to about 500 kPa, e.g., about 0.1 to about 10 kPa, about 0.5 to about 15 kPa, about 1 to about 15 kPa, about 5 to about 20 kPa, about 10 to about 50 kPa, about 20 to about 100 kPa, about 150 to about 300 kPa, about 100 to about 400 kPa, about 200 to about 450 kPa or about 250 to about 500 kPa. In a specific embodiment, the hydrogel is characterized by a stiffness of about 10 kPa, about 15 kPa, about 20 kPa, about 25 kPa, about 30 kPa, about 35 kPa, about 40 kPa, about 45 kPa, about 50 kPa, about 55 kPa, about 60 kPa, about 65 kPa, about 70 kPa, about 75 kPa, about 80 kPa, about 85 kPa, about 90 kPa, about 95 kPa or about 100 kPa.

In some embodiments, the amount of the hematopoietic factor secreted by the cell is at least 1.5-fold greater than the amount of hematopoietic factor secreted by the cell prior to step a.

In a further aspect, the present invention provides a composition comprising a plurality of hydrogel capsules, wherein at least 70%, e.g., at least 75%, 80%, 85%, 90% or 95%, of the hydrogel capsules comprise a single cell and a hydrogel encapsulating the cell, wherein the hydrogel encapsulating the cell has a thickness of less than 20 microns, e.g., less than 19, 18, 17, 16, 15, 14, 13, 12, 11, 10, 9, 8, 7, 6, 5, 4, 3, 2 or 1 microns.

In some embodiments, at least 90%, e.g., at least 91%, 92%, 93%, 94%, 95%, 96%, 97%, 98% or 99%, of the hydrogel capsules in the composition comprise a cell and a hydrogel encapsulating the cell.

In some embodiments, the cell is a mesenchymal stem cell (MSC) or a progenitor thereof, a hematopoietic stem cell (HSC) or a progenitor thereof, or an endothelial progenitor cell. In a specific embodiment, the cell is a mesenchymal stem cell (MSC) or a progenitor thereof.

In certain embodiments, the hydrogel comprises at least one polymer, e.g., the polymer selected from the group consisting of alginate, agarose, poly(ethylene glycol dimethacrylate), polylactic acid, polyglycolic acid, PLGA, gelatin, collagen, agarose, pectin, poly(lysine), polyhydroxybutyrate, poly-epsilon-caprolactone, polyphosphazines, poly (vinyl alcohol), poly(alkylene oxide), poly(ethylene oxide), poly(allylamine), poly(acrylate), poly(4-aminomethylstyrene), pluronic polyol, polyoxamer, poly(uronic acid), poly (anhydride) and poly(vinylpyrrolidone). In a further embodiment, the polymer is alginate.

In some embodiments, the polymer comprises polymer chains cross-linked to each other using a divalent or trivalent cation. For example, the divalent or trivalent cation is selected from the group consisting of $Ca^{2+}$, $Mg^{2+}$, $Sr^{2+}$, $Ba^{2+}$, $Be^{2+}$ and $Al^{3+}$. In a specific embodiment, the divalent cation is $Ca^{2+}$.

In certain embodiments, the diameter of the hydrogel capsule comprising a single cell is between about 10 and 500 micron, e.g., 10-100, 100-200, 200-300 or 400-500 micron. In a specific embodiment, the diameter of the hydrogel capsule comprising a single cell is between about 25 and about 30 micron, about 25 and about 40 micron, about 25 and about 50 micron or about 30 and about 60 micron.

Other features and advantages of the invention will be apparent from the following detailed description and claims.

BRIEF DESCRIPTION OF THE DRAWINGS

FIG. 2A is a set of schematics showing the structure of alginate hydrogels ionically crosslinked with $Ca^{2+}$ (see, e.g., Sun et al. 2012, Nature 489, 133-136).

FIG. 4A is an image showing encapsulation of single MSCs in alginate gel droplets. Green=FITC-alginate (1‰), Red=Phalloidin (F-actin), Blue=DAPI (nucleus).

FIG. 4B is an image, schematic and set of equations showing an AFM measurement scheme. (Top) Droplets (green) seeded in a micro-well made of PDMS. (Bottom) AFM indentation schematics and calculation of Young's Modulus (E) with the Hertz model.

FIG. 4C is a bar graph showing the Young's Modulus (E) of gel droplets (20 um diameter) encapsulated with live single MSCs with different initial $Ca^{2+}$ concentrations. $n\geq 5$ droplets.

FIG. 10A is a set of images showing live imaging of mouse MSC-luciferase in C57BL6/J mice.

FIG. 10B is a set of images and graphs showing prolonged biodistribution of cells by encapsulation.

FIG. 11 is a set of images showing that prolonged biodistribution requires cells to be encapsulated.

FIG. 15 is a set of graphs and images showing the effect of stiffness of alginate gel encapsulating hMSCs on the HSC-enriched number due to protein secretion.

FIG. 17A is an image showing D1 cells directly encapsulated in alginate without pre-coating with nanoparticles and stained for viability (gray circles, alginate; bright circles, live cells).

FIG. 17B is an image showing D1 cells pre-coated with nanoparticles and then encapsulated in alginate (gray circles, alginate; bright circles, live cells).

FIG. 17C is a confocal slice of encapsulated D1 cell. Outer circle, alginate; middle circle, actin; inner circle, nuclei.

FIG. 19A are confocal images of alginate-collagen microgels, scale bar 20 microns.

FIG. 19B are confocal images of alginate-fibrin microgels, scale bar 20 microns.

FIG. 19C is a histogram of alginate fluorescence per pixel in collagen-alginate microgels from confocal slices from 7 different microgels.

FIG. 19D is a scatter plot of polymer concentration per collagen-alginate microgel, as assessed by mean fluorescent intensity, from 168 microgels.

FIG. 19E is a histogram of alginate fluorescence per pixel in fibrin-alginate microgels from confocal slices from 29 different microgels.

FIG. 19F is a histogram of alginate fluorescence per 10 pixels in fibrin-alginate microgels from confocal slices from 29 different microgels.

FIG. 19G is a scatter plot of polymer concentration per fibrin-alginate microgel, as assessed by mean fluorescent intensity, from 103 microgels.

FIG. 19H is a fluorescent image of fibrin-encapsulated D1 cell.

FIG. 19J is a histogram of fibrin concentration per fibrin microgel from 44 different microgels.

FIG. 19L is a graph showing viable fraction of encapsulated D1s in hydrogel capsules of different polymer compositions after 24 hours and 72 hours of culture. ** denotes p<0.01. These figures show encapsulation of D1s in hybrid hydrogel capsules/various polymers.

FIG. 20D is a set of images showing cells encapsulated in FITC-tagged alginate, stained after 6 days of culture, with actin and an ALP marker (white); scale bar=100 µm.

FIG. 20E is a set of confocal images showing some cells still inside hydrogel capsules while others have regressed and proliferated; scale bar=20 µm.

FIG. 20F is a log-log plot of alkaline phosphatase expression by encapsulated D1 cells after 6 days of culture as a function of alginate fluorescence, per microwell, r=0.76, p<0.01. Black line shows least-square fit. The symbols in FIG. 20F indicate different microwell sizes that correspond to those in FIG. 20B. These figures show the seeding and differentiation of encapsulated D1s in a PDMS microwell system.

FIG. 25C is a graph showing blood plasma levels of *Gaussia* Luciferase produced over 300 hours as indicated by area under curve. Student's T-test, *P<0.05, n≥6 recipients.

FIG. 25D is a bar graph showing blood plasma levels of human IL-6 after intravenous injection of hMSCs into NOD/SCID/IL2$\gamma^{-/-}$ (NGS) mice. Total human IL-6 level in blood (pg/ml) over 24 hours after injection of 1 million hMSCs per mouse. Student's T-test, **P<0.005, n≥4 recipients.

FIG. 26A is a graph showing dose response of IL-6 secretion induced by exogenous INF-γ (100 ng/mL) in human primary bone marrow MSCs encapsulated in alginate hydrogels of different stiffness.

FIG. 26B is a graph showing the kinetics of MCP-1 (CCL2) secretion in the presence or absence of TNF-α from human primary bone marrow MSCs encapsulated in alginate hydrogels of different stiffness.

FIG. 26C is a set of two graphs showing the kinetics of secretion of hematopoietic factors from human primary bone marrow MSCs encapsulated in alginate hydrogels of different stiffness. Left panel is a graph showing the kinetics of secretion of SCF following treatment with LPS (20,000 ng/mmL). Right panel is a graph showing the kinetics of secretion of TGF-β from untreated cells.

DETAILED DESCRIPTION OF THE INVENTION

Figure 1:
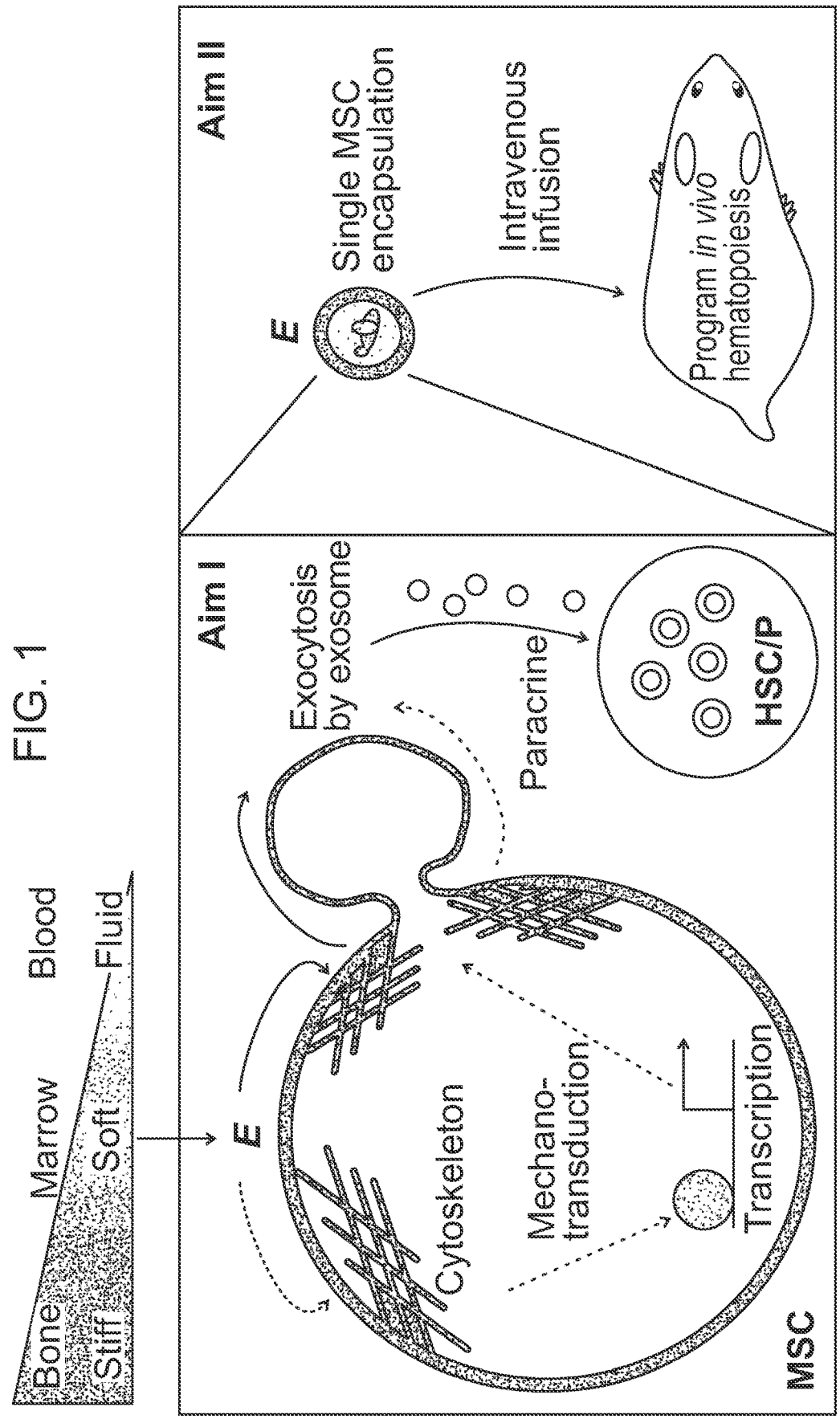
FIG. 1 is a set of schematics showing the regulation of secretion of hematopoietic factors from MSCs by matrix stiffness as well as single MSC encapsulation into a hydrogel and subsequent infusion of the hydrogel to a subject to program hematopoiesis in vivo.

The present invention provides hydrogel capsules containing cells, e.g., single cells, and methods of preparing as well as using them.

The hydrogel capsules and methods described herein provide certain advantages over existing hydrogels and methods of cell delivery. The hydrogel capsules of the invention provide a cell delivery vehicle that is infusible/injectable (like a cell suspension), but that, unlike a cell suspension, permits the control of cells via matrix/gel mechanics. For example, by encapsulating and surrounding one single cell or a few cells in a matrix (e.g., comprising certain mechanical properties, such as stiffness), the cell(s) is surrounded on all sides by the matrix that is instructive to the cell(s) and that leads to certain biological behaviors. In other examples, with the cell(s) surrounded on all sides by the matrix, the matrix is obstructive to the cell(s), e.g., and prevents cell-cell contact, cell growth/proliferation, and/or contact with endogenous cells (e.g., immune cells) from the body.

The hydrogel capsules of the invention are capable of shielding cells, e.g., exogenously administered cells (e.g., encapsulated in the micro-carriers), from clearance by the body, e.g., by immune clearance or metabolism. For example, the hydrogel matrix masks a human leukocyte antigen (HLA) molecule on the encapsulated cell such that the encapsulated cell is capable of evading the host immune system. The encapsulated cells, e.g., secrete factors, e.g., hematopoietic factors or factors that aid in recovery of damaged tissue (e.g., heart tissue). Thus, the hydrogel micro-carriers provide sustained/extended release of such clinically relevant factors.

Further, the hydrogel micro-carriers are injectable/infusible and do not require more invasive methods, such as implantation. For example, the hydrogels are small enough to be intravenously administered/infused, unlike previously described gels, which have a larger size that would block blood vessels if infused.

I. Hydrogel Capsules Containing Cells

In certain embodiments, the present invention provides a composition comprising a plurality of hydrogel capsules, wherein at least 90% of the hydrogel capsules in the composition comprise a cell and a hydrogel encapsulating the cell, wherein the hydrogel encapsulating the cell has thickness of less than 20 microns. For example, at least 91%, 92%, 93%, 94%, 95%, 96%, 97%, 98%, 99% or 99.5% of the hydrogel capsules in the composition may comprise a cell, e.g., one or more cells, such as 1, 2, 3, 4, 5, 6, 7, 8, 9, 10, 15, 20, 25, 30 or more cells.

In other embodiments, the present invention also provides a composition comprising a plurality of hydrogel capsules, wherein at least 70% of the hydrogel capsules comprise a single cell and a hydrogel encapsulating the cell, wherein the hydrogel encapsulating the cell has a thickness of less than 20 microns. For example, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.5% of the hydrogel capsules may comprise a single cell.

In some embodiments, the hydrogel encapsulating the cell has thickness of less than 20 microns, e.g., less than 19, 18, 17, 16, 15, 14, 13, 12, 11, 10, 9, 8, 7, 6, 5, 4, 3, 2 or 1 microns.

The hydrogels described herein comprise a polymer, e.g., an alginate, agarose, poly(ethylene glycol dimethacrylate), polylactic acid, polyglycolic acid, PLGA, gelatin, pectin, collagen, agarose, poly(lysine), polyhydroxybutyrate, poly-epsilon-caprolactone, polyphosphazines, poly(vinyl alcohol), poly(alkylene oxide), poly(ethylene oxide), poly(allylamine), poly(acrylate), poly(4-aminomethylstyrene), pluronic polyol, polyoxamer, poly(uronic acid), poly(anhydride) or poly(vinylpyrrolidone). In one embodiment, the hydrogel comprises an alginate.

Alginates are versatile polysaccharide based polymers that may be formulated for specific applications by controlling the molecular weight, rate of degradation and method of hydrogel formation. Coupling reactions can be used to covalently attach bioactive epitopes, such as the cell adhesion sequence RGD to the polymer backbone. Alginate polymers are formed into a variety of scaffold types. Injectable/infusable hydrogels can be formed from low MW alginate solutions upon addition of a cross-linking agents, such as calcium ions, while macroporous hydrogels are formed by lyophilization of high MW alginate discs. Differences in hydrogel formulation control the kinetics of hydrogel degradation. Release rates of morphogens or other bioactive substances from alginate hydrogels is controlled by the formulation to present morphogens in a spatially and temporally controlled manner. This controlled release not only eliminates systemic side effects and the need for multiple injections/infusions, but can be used to create a microenvironment that activates host cells at a hydrogel implant site and transplanted cells seeded onto/into a hydrogel.

cations (e.g., $Ca^{+2}$, $Mg^{+2}$, $Ba^{+2}$) or trivalent cations (e.g., $Al^{3+}$) and form stable hydrogels when exposed to these molecules. See Martinsen A., et al., Biotech. & Bioeng., 33 (1989) 79-89.) For example, calcium cross-linked alginate hydrogels are useful as a matrix for cells, such as MSCs.

An exemplary hydrogel utilizes an alginate or other polysaccharide of a relatively low molecular weight, preferably of size which, after dissolution, is at the renal threshold for clearance by humans, e.g., the alginate or polysaccharide is reduced to a molecular weight of 1000 to 80,000 daltons. Preferably, the molecular mass is 1000 to 60,000 daltons, particularly preferably 1000 to 50,000 daltons. It is also useful to use an alginate material of high guluronate content since the guluronate units, as opposed to

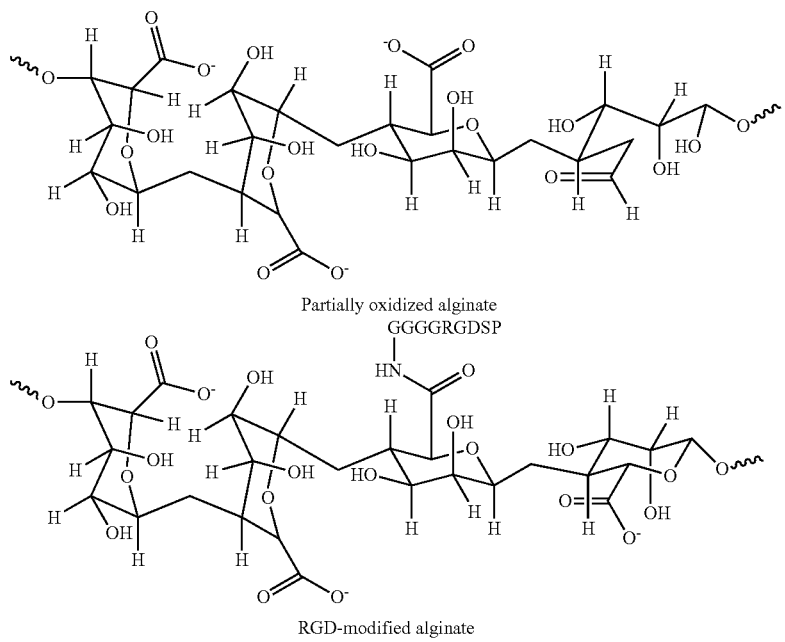

Partially oxidized alginate
GGGGRGDSP

RGD-modified alginate

The hydrogel comprises a biocompatible polymer matrix that is optionally biodegradable in whole or in part. Examples of materials which can form hydrogels include polylactic acid, polyglycolic acid, PLGA polymers, alginates and alginate derivatives, gelatin, collagen, agarose, pectin, natural and synthetic polysaccharides, polyamino acids such as polypeptides particularly poly(lysine), polyesters such as polyhydroxybutyrate and poly-epsilon.-caprolactone, polyanhydrides; polyphosphazines, poly(vinyl alcohols), poly(alkylene oxides) particularly poly(ethylene oxides), poly(allylamines)(PAM), poly(acrylates), modified styrene polymers such as poly(4-aminomethylstyrene), pluronic polyols, polyoxamers, poly(uronic acids), poly (vinylpyrrolidone) and copolymers of the above, including graft copolymers.

The hydrogels may be fabricated from a variety of synthetic polymers and naturally-occurring polymers such as, but not limited to, collagen, fibrin, hyaluronic acid, agarose, pectin, and laminin-rich gels. One preferred material for the hydrogel is alginate or modified alginate material. Alginate molecules are comprised of (1-4)-linked β-D-mannuronic acid (M units) and a L-guluronic acid (G units) monomers, which can vary in proportion and sequential distribution along the polymer chain. Alginate polysaccharides are polyelectrolyte systems which have a strong affinity for divalent the mannuronate units, provide sites for ionic crosslinking through divalent cations to gel the polymer. U.S. Pat. No. 6,642,363, incorporated herein by reference, discloses methods for making and using polymers containing polysaccharides such as alginates or modified alginates that are particularly useful for cell transplantation and tissue engineering applications.

In some examples, the polymer of the hydrogel is modified with (e.g., covalently or noncovalently with) a cell adhesive peptide. Exemplary cell adhesive peptides include arginine-glycine-aspartate (RGD), RGDS (SEQ ID NO: 1), LDV, REDV (SEQ ID NO: 2), RGDV (SEQ ID NO: 3), LRGDN (SEQ ID NO: 4), IKVAV (SEQ ID NO: 5), YIGSR (SEQ ID NO: 6), PDSGR (SEQ ID NO: 7), RNIAEIIKDA (SEQ ID NO: 8), RGDT (SEQ ID NO: 9), DGEA (SEQ ID NO: 10), and VTXG (SEQ ID NO: 11). In some examples, the cell adhesive peptide comprises the RGD amino acid sequence.

The hydrogels of the invention may be porous or nonporous. For example, the hydrogels may be nanoporous having a diameter of less than about 10 nm; microporous wherein the diameter of the pores are preferably in the range of about 100 nm-20 μm; or macroporous wherein the diameter of the pores are greater than about 20 μm, more preferably greater than about 100 μm and even more preferably greater than about 400 μm. Some methods of preparing hydrogels, e.g., hydrogel micro-carriers, are described herein. Other methods of preparing porous hydrogel products are known in the art. (See, e.g., U.S. Pat. No. 6,511,650, incorporated herein by reference).

A hydrogel capsule in the compositions of the invention may comprise 1-50, e.g., 1-40, 1-30, 1-20, 1-10, 9, 8, 7, 6, 5, 4, 3, 2, 1 cells (e.g., mesenchymal stem cells (MSCs) or progenitors thereof, HSCs or progenitor thereof, or endothelial progenitor cells.

Hydrogel encapsulation of a cell prolongs the life/viability of a cell by protecting the cell from immune system mediated cell death, e.g., transplant rejection mechanisms, as well as instructs cells regarding function, e.g., secretion of paracrine factors. For example, hydrogels with specified matrix stiffnesses regulate exocytosis of paracrine factors from cells such as mesenchymal stem cells (MSCs). Mesenchymal stem cells (MSCs) are multipotent stromal cells that can differentiate into a number of different cell types, including osteoblasts, adipocytes, and chondrocytes. In some embodiments, MSCs comprise multipotent cells derived from non-marrow tissues, e.g., umbilical cord blood, adipose tissue, adult muscle, corneal stroma, human peripheral blood, amniotic fluid, or dental pulp of deciduous baby teeth.

In some embodiments, the hydrogel in the compositions of the invention is characterized by a stiffness of 1 Pa-1000 kPa, e.g., 1-10,000 Pa, 10-1000 Pa, 10-500 Pa, 10-100 Pa, 0.1-500 kPa, 1-1000 kPa, 1-500 kPa, 5-1000 kPa, 5-500 kPa, 0.1-500 kPa, 0.1-100 kPa, 1-500 kPa, 1-100 kPa, 5-500 kPa, 5-100 kPa, or 1-50 kPa, e.g., about 1, 5, 10, 15, or 20 kPa.

The polymer in the hydrogel capsule is crosslinked via covalent or noncovalent cross-links. For example, the polymer is crosslinked ionically (i.e., non-covalently) with a divalent or trivalent cation, such as $Ca^{2+}$, $Mg^{2+}$, $Sr^{2+}$, $Ba^{2+}$, $Be^{2+}$ and $Al^{3+}$.

In some examples, the stiffness of the hydrogel encapsulating a cell, e.g., an MSC, induces secretion of a protein factor, e.g., a hematopoietic factor, from the cell, e.g., an MSC. Exemplary protein factors secreted by the cell may include hematopoietic factors, cardiovascular regeneration factors, and graft versus host disease (GVHD) suppression factors. Exemplary hematopoietic factors, cardiovascular regeneration factors, and graft versus host disease (GVHD) suppression factors are described herein. Exemplary hematopoietic factors comprise a stem cell factor (SCF), interleukin-2 (IL-2), interleukin-3 (IL-3), interleukin-6 (IL-6), interleukin-7 (IL-7), granulocyte-macrophage colony stimulating factor (GM-CSF), granulocyte colony stimulating factor (G-CSF), macrophage colony stimulating factor (M-CSF), erythropoietin, thrombopoietin, collagen-I, interleukin-11 (IL-11), angiopoietin-1, or transforming growth factor-beta (TGF-beta). The hydrogel may increase the amount of a protein factor, e.g., a hematopoietic factor, secreted by the cell, e.g., an MSC, by at least 1.5-fold (e.g., at least 1.5, 2, 3, 4, 5, 6, 7, 8, 9, 10, 15, 20, 30, 40, 50, 100-fold, or greater) compared to that of the MSC prior to exposure to the hydrogel.

A cell encapsulated by a hydrogel, e.g., an MSC, may secrete at least one protein factor, e.g., a hematopoietic factor, that is naturally produced by the cell. The cell may also be genetically engineered to modify or eliminate the expression of one or more protein factor that the cell may naturally secrete. For example, the expression of protein factors by such cells may be modified by using techniques known to one of skill in the art, such as plasmid overexpression, RNA interference or CRISPR/Cas9 genome editing.

Alternatively, a cell may secrete at least one protein factor that is not naturally produced by the cell. In such cases, the cell, e.g., an MSC, may be genetically engineered to produce and secrete any protein factor, e.g., using plasmid overexpression.

In some embodiments, a cell encapsulated in the hydrogel capsules of the invention, e.g., an MSC, is capable of immunomodulation. For example, the encapsulated cell, e.g., an MSC, may secrete immunomodulatory factors, e.g., indoleamine 2,3-dioxygenase (IDO), prostaglandin E(2) (PGE(2)), nitric oxide (NO), histocompatibility leucocyte antigen-G (HLA-G), transforming growth factor (TGF)-β, interferon (IFN)-γ and interleukin (IL)-1β. As the immunomodulatory properties of a cell, e.g., an MSC, may depend on its priming with inflammatory factors, a cell may be exposed to priming factors, such as TNF-α and IFN-α, prior to encapsulation. Alternatively, the priming factors, such as TNF-α and IFN-α, may be included in the hydrogel, e.g., an alginate hydrogel, encapsulating a cell, e.g., an MSC. Alternatively, toll like receptor ligands may be covalently coupled to the polymer, e.g., an alginate polymer, used for encapsulation, in order to provide constant stimulation to the encapsulated cells.

In another embodiment, a cell comprised in the hydrogel capsules of the invention may be an MSC-derived induced pluripotent stem cell (an iPS cell).

In some embodiments, an MSC comprised in the hydrogel capsulses of the present invention is a human MSC. In some examples, a cell (e.g., MSC, HSCs/progenitor, or endothelial progenitor) is autologous or heterologous, e.g., allogeneic. For example, a cell (e.g., MSC, HSCs/progenitor, or endothelial progenitor) is autologous. In another example, a cell (e.g., MSC, HSCs/progenitor, or endothelial progenitor) is allogeneic, e.g., a related allogeneic cell or an unrelated allogeneic cell. For example, the hydrogel micro-carrier provides a physical barrier between the encapsulated cell and the body's immune cells, thereby reducing/preventing an adverse host immune response that, in other cases (e.g., where an exogenous cell is administered non-encapsulated) would lead to exogenous cell death mediated by the immune system. As such, the hydrogel micro-carriers described herein permit encapsulation and administration of heterologous cells, e.g., without triggering adverse immune responses.

Figure 7:
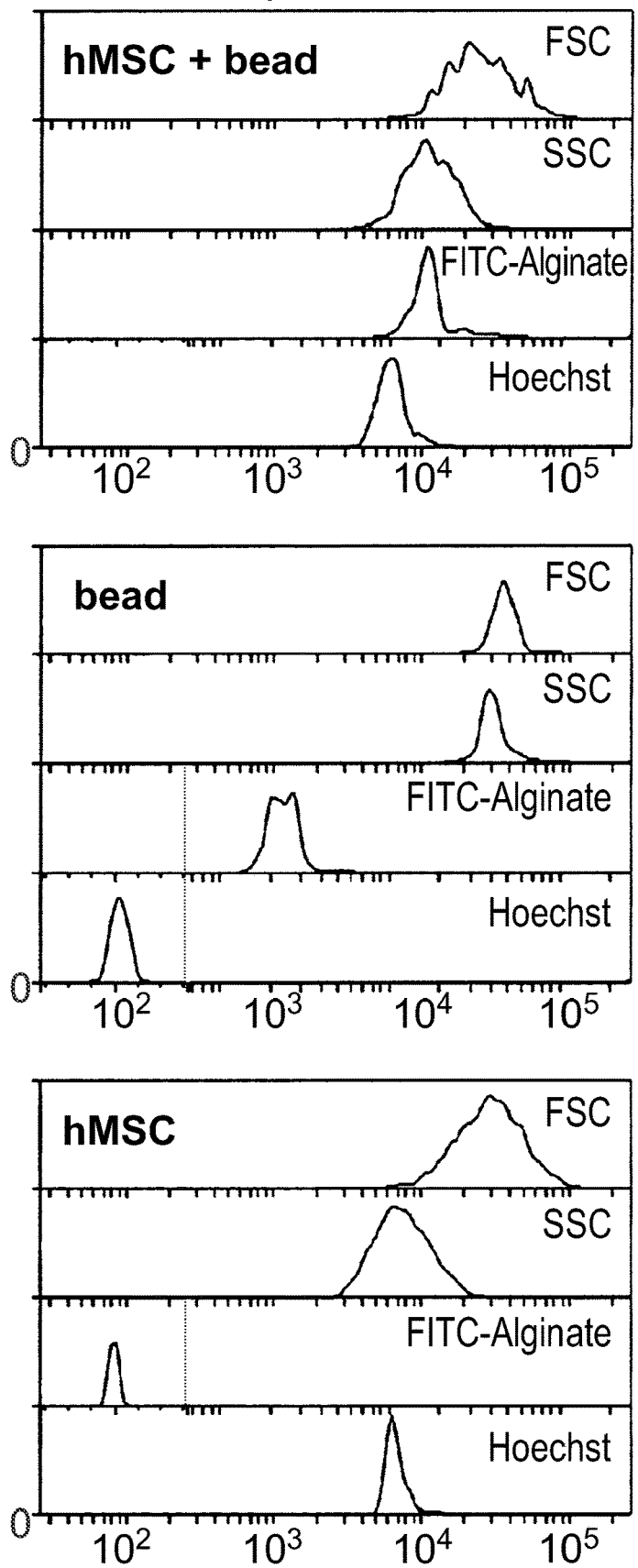
FIG. 7 is a set of images and graphs showing the characterization of single hMSCs encapsulated in alginate beads.

In some examples, the stiffness of the hydrogel microparticles, e.g., alginate microparticles, is controlled by altering initial divalent cation (e.g., calcium carbonate nanoparticle) concentrations, changing polymer (e.g., alginate) concentration, and/or treating the microparticles with additional divalent cations (e.g., calcium ions) after formation. In some cases, to characterize the stiffness, fluorescently labeled microparticles are adhered to a coated glass surface (e.g., poly-1-lysine coated glass surface) or a polydimethylsiloxane (PDMS) microwell, and probed by atomic force microscopy (AFM) to measure Young's Modulus (in Pa) (FIG. 7).

To support cell adhesion to the microparticles, the polymer (e.g., alginate) is optionally conjugated with functional ligands, e.g., by carbodiimide chemistry, with varying degrees of conjugation (substitution) to control ligand density. Exemplary ligands include an Arg-Gly-Asp (RGD) peptide (which binds to integrins αV, α5β1, α8β1, and αIIbβ3) and a Leu-Asp-Val (LDV) peptide (which binds to integrins α4β1, α4β7, α9β1, αEβ7, and the β2 subfamily) (Humphries et al., 2006, J Cell Sci 119, 3901-3903).

Figure 8:
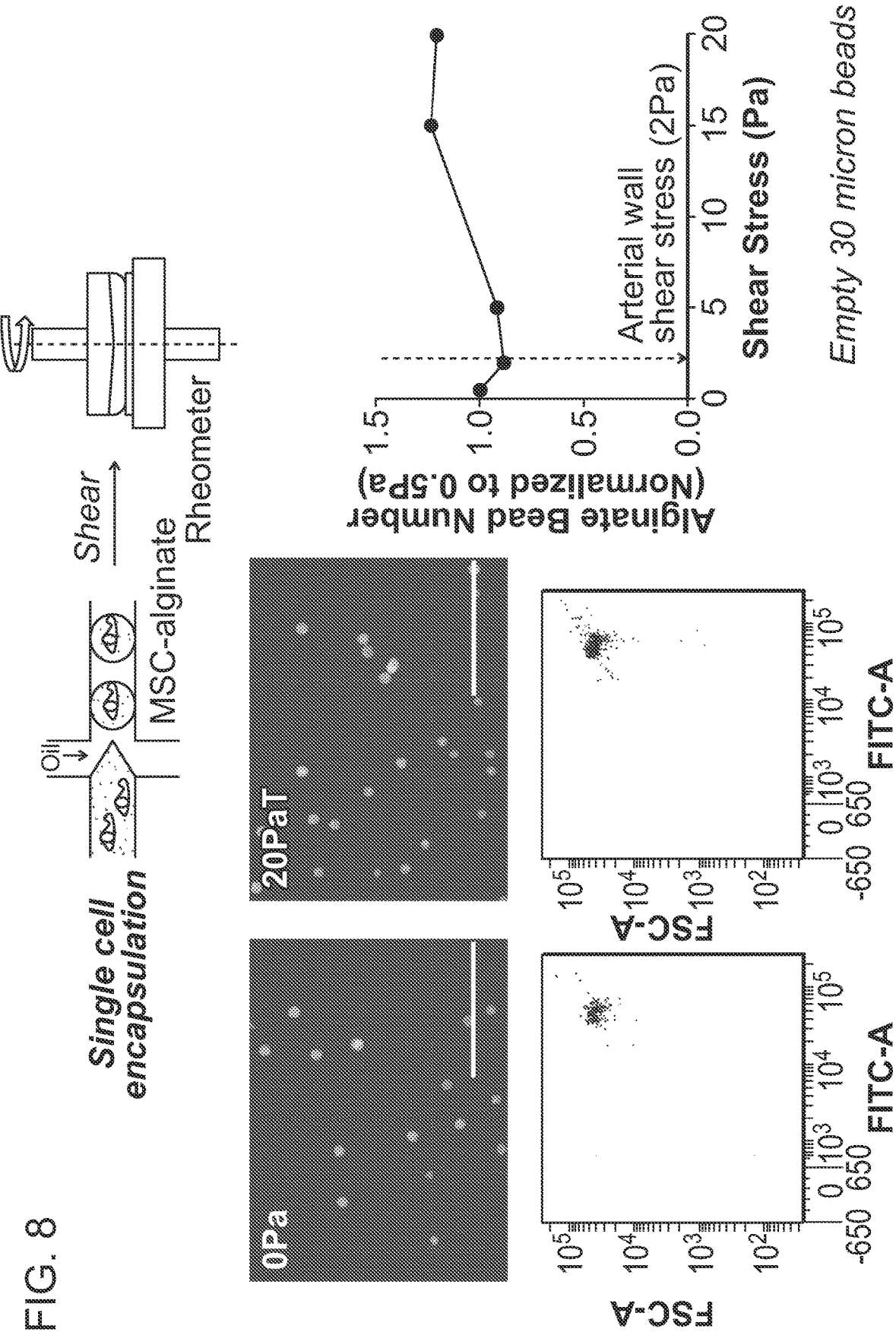
FIG. 8 is a set of images and graphs showing optimization for in vivo delivery alginate beads with stiffness are resistant under in vitro shear.

For example, to test whether hydrogel microparticles can endure shear force experienced by blood circulation after intravenous injection, they were subjected to controlled in vitro shear by a rheometer. Hydrogel (e.g., alginate) microparticles described herein with a Young's Modulus of about 1 kPa (which is in a stiffness range comparable to that of some blood cell types) remained intact after shear force beyond the physiological arterial wall stress (about 2 Pa, FIG. 8), demonstrating that the particles would be able to remain intact in the blood circulation.

The Compositions of the Invention Comprising Hydrogel Capsules Exhibit Prolonged In Vivo Biodistribution Kinetics In some cases, cells encapsulated in hydrogel capsules and administered in vivo remain viable for a longer period of time than cells not encapsulated in the hydrogel capsules, e.g., cells directly injected/infused into a patient. For example, the encapsulated cell(s) comprise a longer serum/plasma stability or half life compared to non-encapsulated cell(s). For example, hydrogel encapsulated cells remain viable after administration in vivo for at least 6 hours, e.g., at least 6, 12, 24, 48 hours, 1, 2, 3, 4, 5, 6, 7 days, 1, 2, 3, 4, 5, 6 weeks, 1, 2, 3, 4, 5, or 6 months, or longer. In other examples, encapsulated cells remain at the site of a targeted tissue (e.g., if injected/infused directly into a target tissue (e.g., lung, heart, kidney, skin, bone marrow) for a longer period of time than non-encapsulated cells. For example, encapsulated cells remain at the site of a targeted tissue for at least 1 hour (e.g., at least 1, 3, 6, 12, 24, 48 hours, 1, 2, 3, 4, 5, 6, 7 days, 1, 2, 3, 4, 5, 6 weeks, 1, 2, 3, 4, 5, or 6 months, or longer). Because of the prolonged biodistribution of the delivered cells, the cell-containing hydrogel microcarriers also circumvent the need for more frequent administrations of cells or cell-secreted factors to a patient.

For example, the hydrogel micro-carriers described herein also increase the cell count, e.g., by physically shielding the cell from immune cells or other clearance mechanisms by the body, and/or by increasing the growth rate of the cell. Exemplary cells included in the micro-carriers comprise MSCs, HSCs or progenitors thereof, or endothelial progenitors. In some cases, the hydrogel micro-carriers comprise a stiffness, e.g., that maintains or increases the cell count compared to other stiffnesses.

To track in vivo biodistribution kinetics of injected cells in hydrogel microparticles by live imaging (e.g. IVIS, Perkin Elmer), the hydrogel is conjugated with fluorescent dyes (e.g. Alexa 750) by carbodiimide chemistry, or with biotin first, followed by binding streptavidin-conjugated fluorescent dyes. For example, cells are labeled with vital dyes (DiR) or are genetically engineered to express fluorescent (e.g. mCherry) or luminescent (e.g. luciferase) proteins. Firefly luciferase is used, e.g., to track the localization of the injected cells, while *Gaussia* luciferase is used, e.g., as a surrogate marker for proteins that are secreted from the transplanted cells into biological fluids, including blood and urine (Tannous, 2009, Nat Protoc 4, 582-591).

In some embodiments, once cells are encapsulated in hydrogel microparticles, they are injected into the body via different administration routes. Exemplary routes include intravenous (retro-orbital, tail-vein), intraperitoneal, subcutaneous, intracardial, intrabone, intratracheal, intramuscular, topical, and oral.

Figure 9:
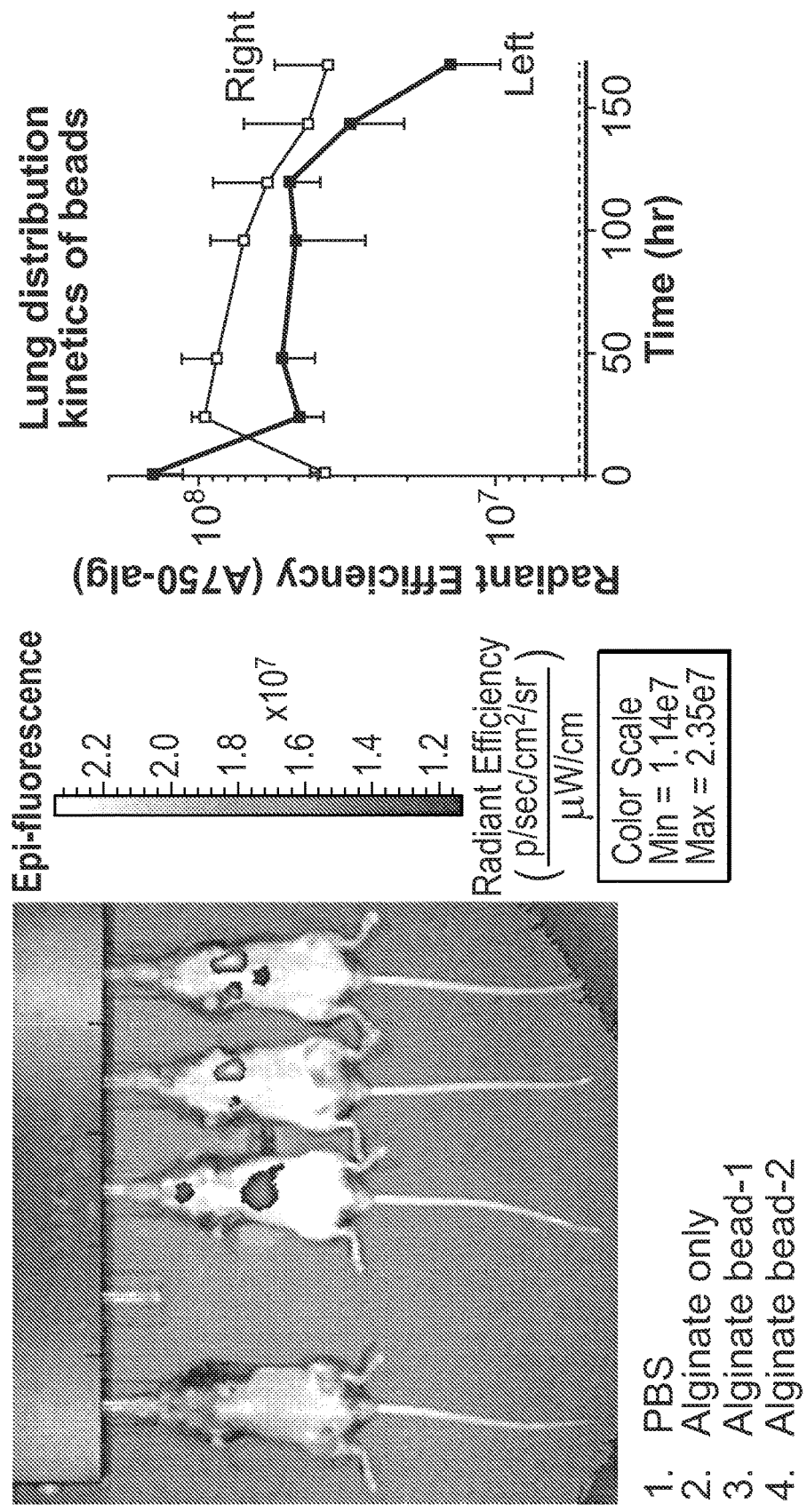
FIG. 9 is a set of images and graphs showing live imaging of alginate beads in C57BL6/J mice.

Retro-orbital injection of a solution containing fluorescent dye-conjugated alginate hydrogel into mice (C57BL/6J) showed sustained accumulation of alginate in the body for more than 2 weeks without compromising health, indicating that alginate is biocompatible (FIG. 9). As shown in FIG. 9, cell-free alginate microparticles with a diameter of 30 μm were produced by a microfluidic method as described above, and injected intravenously. The particles remained in lungs for at least 1 week after intravenous delivery. Particle diameter was about 25-30 μm, and particle stiffness was about 0.3 to 1 kPa. Microparticles were injected retroorbitally (left side). More particles were observed in the left lung at day 0 (P<0.03) than at day 1. At day 1, the signal in the left lung was decreased and that in the right lung was increased. The signals in both the left and right lungs were then decreased over time after more than 1 week.

As shown in FIG. 10, mouse (D1) mesenchymal stem cells (MSCs) were overexpressed with mCherry and firefly luciferase. They were then encapsulated in alginate microparticles conjugated with Alexa 750. An amount of $10^5$ MSCs per mouse was injected. After retro-orbital injection, both luciferase and Alexa 750 signals were tracked for 1 week. While directly injected cells were cleared in 24 hours, the cells encapsulated in alginate microparticles lasted longer in lungs than free cells that were not encapsulated, e.g., by greater than 2-fold (e.g., greater than 2, 3, 4, 5, 6, 7, 8, 9, or 10-fold, e.g., greater than 10-fold), as indicated by the calculation of the area under curve.

Further, to confirm that that prolonged biodistribution of MSCs in lungs after intravenous injection was due to physical shielding of single cells rather than mixing with alginate, cells in alginate microparticles were compared with unencapsulated cells that were mixed with empty alginate microparticles. The results showed that unencapsulated cells mixed with empty alginate beads were cleared within 24 hours, while encapsulated cells were alive and remained in lungs at this 24 hours (e.g., at least 24 hours, e.g., at least 24, 36, 48 hours or greater) (FIG. 11).

Figure 12:
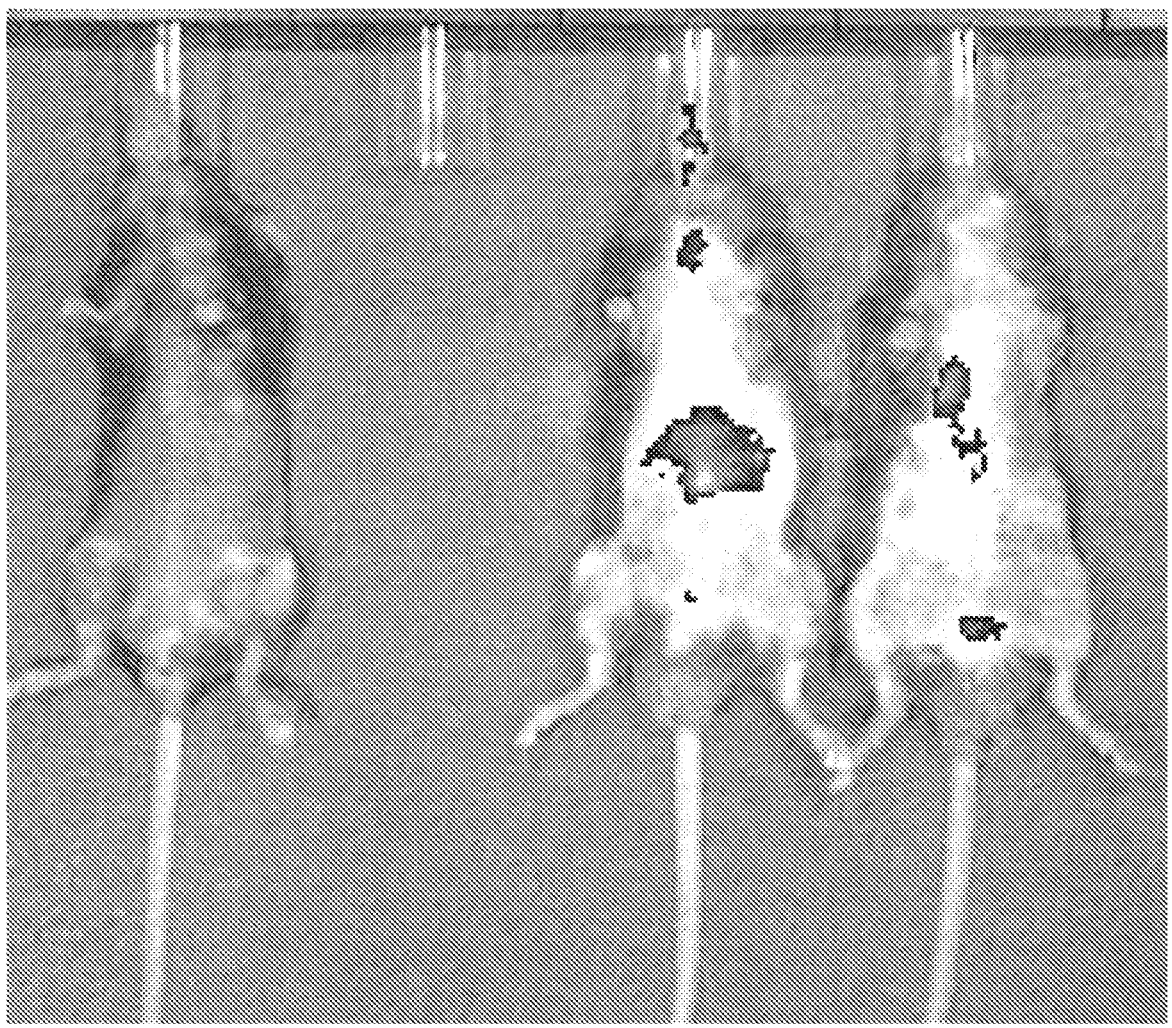
FIG. 12 is an image showing that injection of the beads into the left ventricle of the heart led to localization in the liver.

In addition, as shown in FIG. 12, alginate capsules without cells were localized in the liver when they were injected directly into the left ventricle of the heart. This was in contrast to the retro-orbital injection, where the particles were localized predominantly in the lungs.

Figure 13:
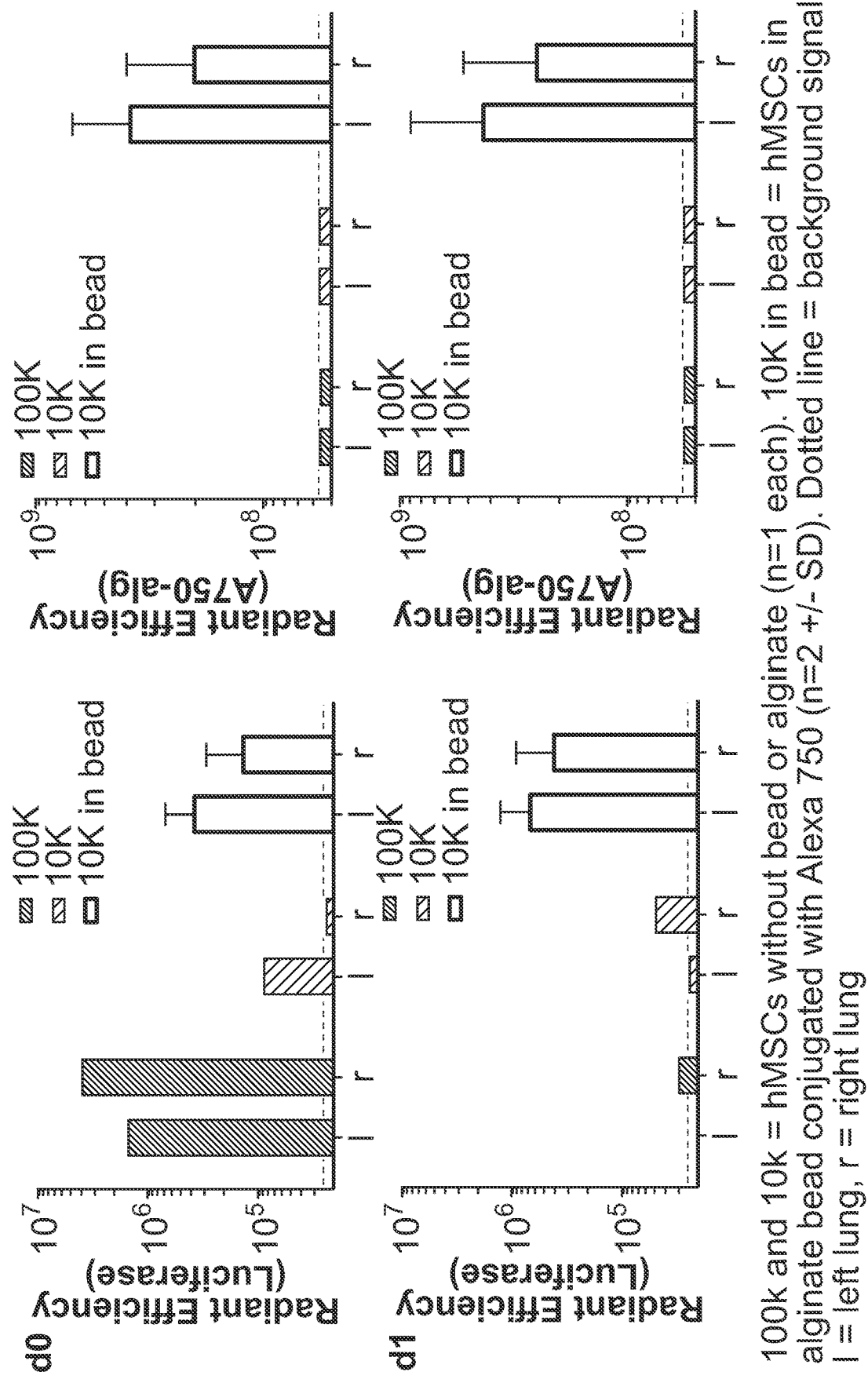
FIG. 13 is a set of graphs showing live imaging of human MSC-luciferase in NSG mice.

Further, experiments were done with human MSCs that express mCherry and luciferase. After encapsulation, human MSCs were injected intravenously in NOD/SCID/IL2gamma$^{-/-}$ mice that were sublethally irradiated (2.5 Gy). The results showed a similar trend as those from the experiments with mouse cells described above, demonstrating prolonged biodistribution after encapsulation (FIG. 13).

Figure 14:
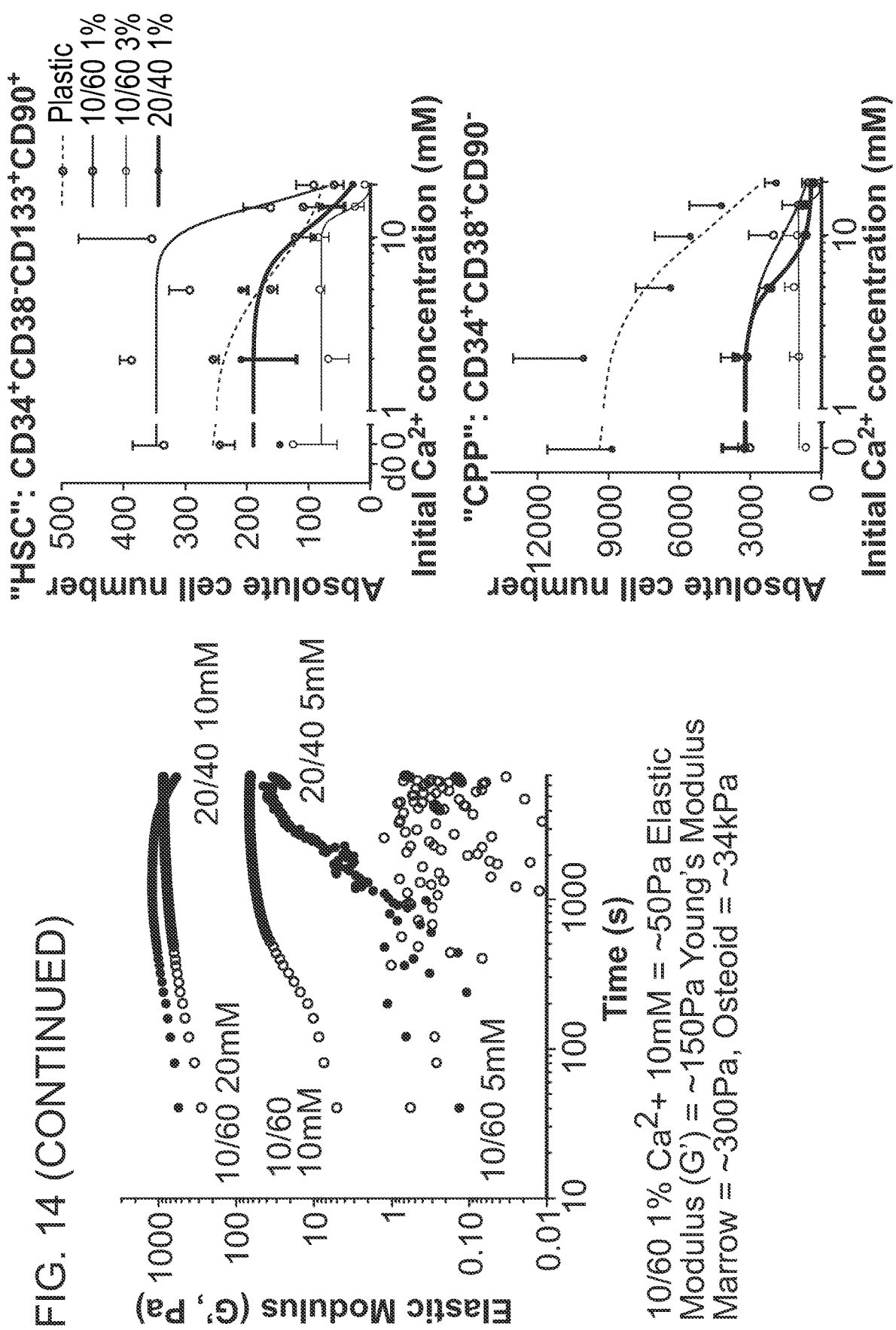
FIG. 14 is a set of schematics and graphs showing that soft substrate stiffness maximized HSC-enriched subpopulation, e.g., in gels comprising HSCs.

In the hydrogel capsules of the invention, physical properties of the hydrogel encapsulating the cells may be altered. Changes in the physical properties of the hydrogel may, in turn, alter the biological effect that the hydrogel capsules exert on a subject being administered the compositions of the invention. For example, changing the stiffness of the hydrogel may alter secretion of protein factors, e.g., hematopoietic factors, from an encapsulated cell, e.g., an MSC. For example, FIG. 14 demonstrates the effect of altering physical properties of the hydrogel on the number of hematopoietic stem cells (HSC) and committed progenitors (CPP). Specifically, physical properties of alginate hydrogels were altered either by changing concentration of calcium used for the cross-linking reaction; by varying alginate concentration; or by varying alginate molecular weight ("¹⁰⁄₆₀": 120 kDa or "²⁰⁄₄₀": 250 kDa). The physical properties of the resulting hydrogels were characterized using a rheometer. Soft hydrogels that comprised HSCs/progenitors were more effective at increasing the number of HSCs, as compared to stiffer hydrogels. Accordingly, by varying the stiffness/composition of the hydrogels, the number of HSCs and progenitors is maximized in vivo by encapsulating the HSCs/progenitors in soft alginate microparticles followed by injection.

For example, hydrogel microparticles may comprise a cell, e.g., an HSC or an CPP. Such hydrogel microparticles are characterized by low stiffness, e.g., have an elastic modulus of about 1-5000 Pa, e.g., 10-1000 Pa, e.g., 10-500 Pa, e.g., 20-300 Pa, e.g., 30-300 Pa, e.g., 50-300 Pa, e.g., 50-150 Pa. Optionally, such hydrogels comprises a divalent cation (e.g., calcium ion) at the concentration of about 1-10 mM, e.g., 1-5 mM, e.g., 1-2 mM, and, e.g., an alginate molecular weight of about 120 kDa.

In some examples, the physical properties of the hydrogel capsules control the release kinetics of secretions from encapsulated cells. For example, as shown in FIG. 15, there was an optimal stiffness for alginate hydrogels to control the release of secretory factors from MSCs, which in turn maximized the number of HSCs. Hydrogel stiffness increased the total amount of proteins released per cell (e.g., MSC). The release kinetic profiles of individual proteins in response to hydrogel stiffness was distinct depending on the size of the proteins.

Given the prolonged biodistribution of in vivo injected single cells encapsulated in hydrogel microparticles (FIGS. 10-13), the results show that the mechanics of the hydrogels can be harnessed to control the release of proteins from the encapsulated single cells in vivo.

This approach is not limited to the delivery of endogenously secreted factors. In some examples, cells are engineered to overexpress exogenous (e.g., recombinant) secretory proteins (e.g. *Gaussia* Luciferase), and their release kinetics are controlled by hydrogel microparticles that encapsulate the cells (and their stiffness).

In some cases, to control the release of secreted factors from cells, the pore size of alginate microparticles is varied. Alginate hydrogels without any modification are nanoporous (<5 nm pore size), permitting the passage of proteins up to the size of 50 kDa (e.g. *Gaussia* Luciferase, which is ~19 kDa). However, in some cases, hydrogels are modified to comprise pores of other sizes, e.g., >5 nm, e.g., at least 10 nm, e.g., 10-500 nm, e.g., 10-100 nm.

Tuning the stiffness of hydrogels induces protein release from cell, e.g., MSCs. Proteins can be secreted directly into the extracellular space via conventional exocytosis pathways (e.g., direct release without extracellular vesicles). In other examples, proteins can also be released indirectly, e.g., by packaging into extracellular vesicles that include exosomes (40-100 nm in diameter) and microvesicles (0.1-1 μm). For example, these vesicles are also known to contain small RNAs, such as microRNAs. Directly released proteins are capable of leaving a hydrogel micro-carrier comprising pores of 5 nm or less, e.g., alginate-based hydrogel microcarrier (which comprise a pore size of 5 nm or less). However, for those proteins that are released indirectly via extracellular vesicles (e.g, size/diameter >50 nm), the vesicles cannot leave the hydrogel micro-carrier on their own (FIG. 15). To allow the release of the vesicles, the pore size of the hydrogel micro-carrier is, e.g., increased, e.g., to hundreds of nm or more. For example, hematopoietic or other factors (e.g., those that aid in recovery of damaged heart tissue) are secreted directly or via extracellular vehicles.

In some examples, a hydrogel described herein, e.g., alginate hydrogel, does not allow the passage of an extracellular vesicle (FIG. 15). In some cases, to enable the release of extracellular vesicles from hydrogel capsules, rapidly degradable nanoparticles with a defined size are incorporated when the hydrogel capsules are synthesized, e.g., to generate pores in the hydrogel capsules. The materials appropriate for degradable nanoparticles include, e.g., oxidized alginate and poly (D,L-lactide-co-glycolide) (PLGA). Sub-micron porous hydrogel micro-carriers are also useful for the delivery of synthetic nanoparticles, such as gold and magnetic nanoparticles.

In some examples, to permit the release of cell-derived microparticles, e.g., exosomes, microvesicles, or other parts of a cell, that are larger than nanoparticles but smaller than the size of a cell (e.g., between 1 and 10 μm), monodisperse spherical porogens with a size (e.g., diameter) between 1 and 10 μm are microfluidically formed as described above, e.g., with oxidized alginate. In some cases, the porogens are then encapsulated along with cells in larger hydrogel microparticles, and they are degraded to form pores in the hydrogel microparticles. Naturally occurring cell-derived microparticles that are delivered by the method include platelets and apoptotic bodies. These particles are directly incorporated into the microparticles or produced by encapsulating their precursors, including megakaryocytes and apoptotic cells, respectively.

In some examples, pore size of the hydrogel capsules is controlled such that certain secreted molecules are released from the hydrogel, e.g., into the rest of the body, and other secreted molecules are trapped inside the hydrogel, e.g., kept from diffusing into the rest of the body. For example, nanoporous hydrogels (e.g., alginate hydrogels) comprise a pore size of 20 nm or less (e.g., 20, 15, 10, 5, 4, 3, 2, 1 nm or less). Such pore sizes permit the migration, e.g., outward migration, of proteins of about 200 kDa or less (e.g., 200, 150, 100, 90, 80, 70, 60, 50, 40, 30, 20, 10, 5, 2 kDa or less) through the pores. Such pore sizes exclude the migration, e.g., outward migration, of larger molecules, e.g., with a molecular weight of greater than 200 kDa, e.g., exosomes, microvesicles, or other microparticles (such as platelets or apoptotic bodies) through pores. In other examples the hydrogel micro-carrier comprises larger pores. For example, larger pores, e.g., comprising a diameter of greater than 20 nm (e.g., 30 nm, or greater, 30, 40, 50, 60, 80, 100, 120, 150, 200, 400, 600, 800 nm, 1 μm, 2 μm, 4 μm, 8 μm, or greater) permit the migration of secreted proteins as well as secreted exosomes, microvesicles, and microparticles (e.g., platelets and apoptotic bodies) through the pores, e.g., out of the hydrogel.

In accordance with the hydrogels and methods described herein, prolonged in vivo delivery of MSCs improves the treatment of a range of disease conditions. Cell therapies using MSCs are currently tested for over 300 clinical trials, but the biodistribution kinetics of MSCs after intravenous injection is generally too short, as shown in FIGS. 10 and 13. Prolonging the biodistribution of MSCs by single cell encapsulation, as provided by the methods herein, is thus useful for treating a number of disease conditions where MSCs have been shown to be beneficial. For example, MSCs have been shown to be useful in the treatment of degenerative, inflammatory, and autoimmune diseases. See, e.g., Farini et al. Stem Cells Intl. 2014, 2014:306573. MSCs have immunomodulatory effects, e.g., they inhibit cytotoxic T cells and natural killer (NK) cells, e.g, by secreting suppressors of T-cell development (such as TGF-beta and hepatocyte growth factor (HGF)) and suppressors of proliferation (such as leukemia inhibitory factor (LIF) and interferon-gamma (IFN-gamma)). MSCs can also induce expression of tumor necrosis factor-alpha (TNF-alpha) and interleukin-1 (IL-1), which can lead to secretion of chemokines and inducible nitric oxide synthase (iNOS). See id. Also, MSCs have been used in the treatment of musculoskeletal diseases, such as Duchenne muscular dystrophy (DMD), as well as in the regeneration of muscle, e.g., skeletal muscle tissue, and the treatment of osteonecrosis, spinal fusion disease, severe osteogenesis imperfect. See id. MSCs are also useful in the treatment of cardiovascular diseases/cardiovascular repair, as MSCs secrete molecules that have important effects on the cellular microenvironment and also differentiate into cardiomyocytes. MSCs decrease fibrosis in the myocardium and improve myocardial contractility and ventricular function, and are useful for treating dilated cardiomyopathy. See id. For example, molecules secreted by MSCs are able to protect the myocardium by preserving its contractile capacity; in particular, MSCs-derived cytokines inhibit the apoptosis of cardiomyocytes, allowing the formation of new vessels in damaged tissues. See id. MSCs are also useful for treating liver diseases, e.g., cirrhosis, end-stage liver disease, and fulminant hepatic failure (FHF), e.g., by reducing hepatocellular death and increasing hepatocellular proliferation. See id. In addition, MSCs have been used to block the development of chronic inflammatory processes that occur in autoimmune arthritis, diabetes, and lupus. Accordingly, MSCs are useful for the treatment of rheumatoid arthritis, systemic lupus erythematosus, and Type 1 diabetes. In other cases, MSCs are useful for treating neurodegenerative diseases, such as amyotrophic lateral sclerosis, multiple sclerosis, Alzheimer's disease, and Parkinson's disease. See id.

The single cell encapsulation methods and hydrogels described herein are useful for improving the secretion of therapeutic factors from the encapsulated MSC and/or the integration of the delivered MSC into the host. Disease conditions treatable using the hydrogels/methods described herein include hematological malignancies, bone marrow failure, bone marrow transplantation, graft versus host disease (GVHD), acute radiation syndrome, cardiac regeneration, acute respiratory distress syndrome, and septic shock (Syed and Evans, 2013, Nat Rev Drug Discov 12, 185-186). For example, MSCs suppress T-cell activation under some conditions in vitro (Di Nicola et al., 2002, Blood 99, 3838-3843), but the efficacy of MSCs is likely to be diminished in vivo due to the rapid clearance after injection. Single cell encapsulation is thus useful to improve the efficacy of MSCs to prolong the suppression of donor T-cells that cause GVHD in patients that undergo hematopoietic transplantation, e.g., HSC transplantation.

For example, a MSC described herein, e.g., encapsulated in a hydrogel described herein, secretes a cardiovascular regeneration factor and/or a GVHD suppression factor. Cardiovascular regeneration factors from MSCs include vascular endothelial growth factor (VEGF), stromal cell derived factor 1 (SDF-1), tumor necrosis factor-inducible gene 6 protein (TSG-6), interleukin-6 (IL-6), interleukin-8 (IL-8), basic fibroblast growth factor (bFGF or FGF-2), insulin-like growth factor 1 (IGF-1), hepatocyte growth factor (HGF), Thrombospondin-4, secreted frizzled-related protein 2 (Sfrp2), matrix metalloproteinase 9 (MMP-9), tissue inhibitior of metalloproteinases (TIMP) metallopeptidase inhibitor 2 (TIMP-2), monocyte chemotactic protein 1 (MCP-1), thrombospondin 1 (TSP-1), chemokine (C-X-C motif) ligand 6 (CXCL6), interferon gamma-induced protein 10 (IP-10). For examples, Genbank Accession Nos. for these protein factors are incorporated herein by reference and are as follows: VEGF (P15692.2), SDF-1 (P48061.1), TSG-6 (P98066.2), IL-6 (P05231.1), IL-8 (P10145.1), FGF-2 (P09038.3), IGF-1 (CAA01955.1 or CAA01954.1), HGF (P14210.2), thrombospondin-4 (NP_003239.2), Sfrp2 (Q96HF1.2), MMP-9 (P14780.3), TIMP-2 (P16035.2), MCP-1 (P13500.1), TSP-1 (Q9HCB6.2 or NP_003237.2), CXCL6 (P80162.4), and IP-10 (P02778.2).

GVHD suppression factors from MSCs include transforming growth factor-beta (TGF-beta), hepatocyte growth factor (HGF), prostaglandin E2 (PGE2), galectin, and Indoleamine 2,3-dioxygenase (IDO). For examples, Genbank Accession Nos. for the protein factors are incorporated herein by reference and are as follows: TGF-beta (AAA36738.1), HGF (P14210.2), galectin (88922.1), and IDO (P14902.1). The structure of PGE2 is shown below:

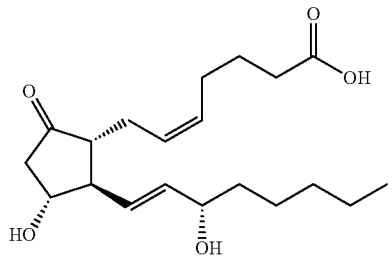 [SMILES: CCCCC[C@H](O)/C=C/[C@H]1[C@H](O)CC(=O)[C@@H]1C/C=C\CCCC(=O)O]

In addition, prolonged in vivo delivery of endothelial progenitors is useful for improving treatment of a number of diseases. For example, endothelial progenitors are delivered via single cell encapsulation methods as described herein to improve the regeneration of tissues in vivo. Tissues to be regenerated by endothelial progenitors include blood, damaged muscles, liver, and lungs (Manavski et al., 2014, Circ Res 114, 1077-1079).

Further, prolonged delivery of engineered cells and microorganisms is applicable to approaches in synthetic biology. For example, cells and microorganisms are engineered to express a genetic circuit that can respond to specific factors known to be present in physiological and pathological conditions (Wieland and Fussenegger, 2012, Annu Rev Chem Biomol Eng 3, 209-234). The single encapsulation method described herein permits the in vivo application of the synthetic biology approach by improving the biodistribution kinetics of the engineered cells and microorganisms that can sense and respond to signals from their milieu. From a safety perspective, because alginate microparticles without modification have a small pore size (<5 nm), they can be used to physically shield engineered microorganisms within the host after transplantation, while still permitting the passage of therapeutic molecules from the engineered microorganisms into the host.

II. Methods of Preparing Hydrogel Capsules Containing Cells

High-throughput encapsulation of cells into microscale hydrogels is a technology that has great utility and promise but that currently involves several challenges. For example, challenges include achieving a thin hydrogel layer around encapsulated cells, increasing the yield of cell-containing particles, controlling the mechanical properties of the hydrogel, and enabling long-term culture of encapsulated cells. The present invention provides a gentle method for single-cell encapsulation that may comprise the following steps:

a) contacting a cell with a moiety capable of adhering to a cell and comprising a cross-linking catalyst; and b) contacting the cell and the moiety with at least one polymer comprising a plurality of polymer chains;

wherein the cross-linking catalyst catalyzes a reaction that cross-links said plurality of polymer chains. In certain examples, the moiety capable of adhering to a cell and comprising a cross-linking catalyst may be a nanoparticle, such as a $CaCO_2$ nanoparticle, a $BaCO_3$ nanoparticle, or a $SrCO_3$ nanoparticle.

Without wishing to be bound by a specific theory, it is believed that adherence of the moiety comprising a cross-linking catalyst to a cell prior to hydrogel formation is important for increasing encapsulation yield, i.e., fraction of all hydrogel capsules in the composition that comprise a cell, e.g., one or more cells. It is also believed, without wishing to be bound by a specific theory, that adherence of the moiety comprising a cross-linking catalyst to a cell prior to hydrogel formation is important for increasing encapsulation efficiency, i.e., fraction of all cells in the composition that become encapsulated. Accordingly, adherence of a moiety comprising a cross-linking catalyst to a cell prior to hydrogel, allows for producing compositions with at least 90% encapsulation yield and at least 90% efficiency.

In specific examples provided herein, single-cell encapsulation in alginate is achieved by adsorbing calcium carbonate nanoparticles to cells prior to forming cell droplets. The method was tested on three cell types, a mesenchymal stem cell line (D1), a preadipocyte cell line (OP9), and primary outgrowth endothelial cells (OEC). Depending on the cell type, the efficiency and yield of encapsulation ranged from 49% to 88%, and the viability over a three-day period ranged from 60% to 90%. Using D1s, the hydrogel capsules were mechanically tractable, and hybrid hydrogel capsules were successfully formed from a mixture of polymers. Also, a PDMS microwell culture system was used to study osteogenic differentiation of encapsulated mesenchymal stem cells.

The methods described herein overcome many of the previous challenges with high-throughput encapsulation of cells into hydrogels. Encapsulation of single cells by a thin hydrogel layer is useful for a variety of fields, including the assembly of complex tissues, high throughput small molecule and drug screens, and cell delivery therapies. Microfluidics and surfactant chemistry have been used to encapsulate cells in microscale hydrogels (>60 µm), but these approaches suffer several drawbacks. For example, previously described hydrogel capsules are generally much larger than the cells they encapsulate, and, in most approaches, increasing the fraction of droplets containing cells requires high cell densities and often results in multiple cells per droplet. See, e.g., Selimovic et al. Polymers (Basel). 4, 1554 (2013); Chung et al. *Lab Chip.* 12, 45-59 (2012); Martinez et al. *Macromol. Biosci.* 12, 946-951 (2012); and Tan et al. *Adv Mat.* 19, 2696-2701 (2007). Little work has been done on controlling hydrogel properties and on long-term culture of cells encapsulated in hydrogel capsules.

The methods and compositions described herein provide advancements to the field of single-cell encapsulation, including cell encapsulation within a thin hydrogel layer; a one-step method for increasing the fraction of hydrogel capsules containing cells; control over mechanical properties of the hydrogel matrix; fabrication of cell-encapsulating hybrid hydrogel capsules; and demonstration that assembled encapsulated cells can function analogously to cells in 2D at similar size scales.

Provided herein is a method for encapsulating cells in a thin hydrogel coating and creating hydrogel capsules comprising cells. The method achieves high yield, i.e., results in composition that comprises a high fraction of hydrogel capsules that contain a cell, e.g., one or more cells. The method also achieves high efficiency, i.e., results in a high fraction of cells that are encapsulated into hydrogel capsules. The encapsulated cells produced by the method of the invention are also characterized by high long-term viability. Further, physical properties of the hydrogel encapsulating the cells may be altered, thereby controlling the behavior of microencapsulated cells.

In some embodiments, the present invention provides a hydrogel capsule comprising a polymer and 50 or fewer cells (e.g., 50, 40, 30, 20, 15, 10, 9, 8, 7, 6, 5, 4, 3, 2, or fewer, e.g., 1 cell), where the hydrogel capsule comprises a diameter of 500 µm or less (e.g., 500, 400, 300, 200, 150, 100, 90, 80, 70, 60, 50, 40, 30, 20 µm or less), and where the cells are fully surrounded by a layer of hydrogel. In other embodiments, the hydrogel capsule bead diameter is at least 20 µm (e.g., at least 20, 30, 35, 40, 45, 50, 55, 60, 65, 70, 75, 80, 85, 90, 95, 100 µm, or greater). For example, the diameter is 20-500 µm. For example, the layer of hydrogel surrounding the cells is 0.5 to 20 µm thick (e.g., 0.5-15 µm, 0.5-12 µm, 0.5-10 µm, 0.5-7.5 µm, 1-20 µm, 1-15 µm, 1-10 µm, 1-5 µm, 0.8-12 µm, or about 4.8 µm thick). As used herein, the term "diameter", when used in reference to the hydrogel capsule having an irregular spherical shape, refers to the longest dimension of the hydrogel capsule. The term "diameter", as used herein, also refers to the diameter of a hydrogel capsule having a perfect spherical shape.

Polymers include biocompatible polymers, e.g., that can be cross-linked in a cell-compatible, gentle, way. In the presence of calcium, the polymer forms a solid, and its elastic modulus is adjusted by changing the concentration of its cross-linker. An exemplary suitable polymers include alginate, collagen, fibrin, agarose, poly(ethylene glycol dimethacrylate), polylactic acid, polyglycolic acid, PLGA, gelatin, agarose, poly(lysine), polyhydroxybutyrate, poly-epsilon-caprolactone, polyphosphazines, poly(vinyl alcohol), poly(alkylene oxide), poly(ethylene oxide), poly(allylamine), poly(acrylate), poly(4-aminomethylstyrene), pluronic polyol, polyoxamer, poly(uronic acid), poly(anhydride) or poly(vinylpyrrolidone). In one embodiment, the polymer is alginate.

For example, the polymer (e.g., alginate) is ionically crosslinked by a divalent cation, such as $Ca^{2+}$, $Mg^{2+}$, $Sr^{2+}$, $Ba^{2+}$, $Be^{2+}$ or $Al^{3+}$. In one embodiment, the divalent cation comprises $Ca^{2+}$. In one embodiment, alginate is used in an encapsulating hydrogel. Alginate is a biocompatible polymer capable of a gentle mode of cross-linking. In the presence of a divalent ion (e.g., calcium), alginate crosslinks to form a hydrogel, and it elastic modulus can be adjusted by changing the concentration of the divalent ion (e.g., calcium).

A multitude of cell types are suitable for encapsulation using the methods described herein. For example, a cell may be a mesenchymal stem cell (MSC) or a progenitor thereof, a hematopoietic stem cell (HSC) or a progenitor thereof, pre-adipocyte cell, or an endothelial cell.

In the studies described herein, cells were pre-coated with cation-containing nanoparticles (e.g., calcium carbonate), mixed with liquid polymer (e.g., sodium alginate), and extruded through a small aperture within a microfluidic device. Dissolution of the nanoparticles led to polymer (e.g., alginate) cross-linking, producing a thin hydrogel layer around encapsulated cells. Because nanoparticles containing the cation crosslinker were adsorbed to the cells prior to cross-linking, the method achieved a high fraction of cell-containing hydrogel capsules.

Accordingly, a method of encapsulating a cell in a hydrogel capsule may comprises the following steps:

a) providing a microfluidic device comprising intersecting open channels;

b) providing an aqueous phase liquid comprising a cell, a divalent cation or salt thereof, and a polymer;

c) providing a nonaqueous phase liquid comprising an oil and an acid;

d) injecting the aqueous phase liquid into a channel of the device while simultaneously injecting the nonaqueous phase into a separate channel of the device to form an emulsion; and e) contacting the emulsion with a cell-compatible solution to form an individual polymeric hydrogel capsule bead comprising a cell encapsulated within the hydrogel capsule.

In some embodiments, the aqueous phase liquid of step b) is made by the following steps:

mixing cells with nanoparticles comprising the divalent cation or salt thereof, thereby coating the cells with the nanoparticles;

removing unbound nanoparticles from mixture; and mixing the nanoparticle coated cells with the polymer.

For example, the nanoparticle, e.g., comprising a divalent cation or salt thereof, comprises a diameter of 400 nm to 1000 nm (e.g., 450-950 nm, 500-900 nm, 400-800 nm, 500-900 nm, 550-800 nm, 600-800 nm, 550-750 nm, or about 680 nm). In some examples, the nanoparticle is present at a concentration of 1-50 mg/mL or 50 mM or less (e.g., 1-40 mg/mL, 1-30 mg/mL, 1-20 mg/mL, 1-10 mg/mL, 5-50 mg/mL, 10-50 mg/mL, 20-50 mg/mL, 30-50 mg/mL, 40-50 mg/mL, 20-40 mg/mL, 20-30 mg/mL, 30-40 mg/mL; or 40 mM, 30 mM, 25 mM, 20 mM, 15 mM, 10 mM, 5 mM, 2.5 mM, 1.5 mM, 1 mM or less).

In some examples, a nanoparticle described herein comprises a zeta potential in media of −10 mV or lower (more negative), e.g., −10 mV to −60 mV, e.g., about −20 mV, for example, −23 mV. The magnitude of (absolute value of) the zeta potential is a measure of the degree of electrostatic repulsion between adjacent, similarly charged particles in a dispersion. For example, a high zeta potential (negative or positive) indicates that the solution or dispersion is more electrically stabilized and will resist aggregation, while a low zeta potential (negative or positive) indicates that the dispersion is more likely to break and aggregate or flocculate.

In some cases, the aqueous phase liquid comprises a divalent cation at a concentration of 1-50 mg/mL or 50 mM or less (e.g., 1-40 mg/mL, 1-30 mg/mL, 1-20 mg/mL, 1-10 mg/mL, 5-50 mg/mL, 10-50 mg/mL, 20-50 mg/mL, 30-50 mg/mL, 40-50 mg/mL, 20-40 mg/mL, 20-30 mg/mL, 30-40 mg/mL; or 40 mM, 30 mM, 25 mM, 20 mM, 15 mM, 10 mM, 5 mM, 2.5 mM, 1.5 mM, 1 mM or less).

In some embodiments, the divalent cation is $Ca^{2+}$, $Mg^{2+}$, $Sr^{2+}$, $Ba^{2+}$, or $Be^{2+}$. For example, the divalent cation is $Ca^{2+}$. In other embodiments, the trivalent cation comprises $Al^{3+}$.

In some cases, the oil of step c) of the method is a fluorinated oil, soybean oil, corn oil, mineral oil, hexadecane, or a combination thereof. Exemplary acids suitable for the method include acetic acid, formic acid, benzoic acid, oxalic acid, lactic acid, propionic acid, butyric acid, and combinations thereof.

In some examples, the nonaqueous phase liquid further comprises a surfactant.

In some embodiments, a cell compatible solution, e.g., as used in step e) of the method, includes cell culture media.

In accordance with the methods described herein, the channels microfluidic device comprise a diameter of 10-500 µm (e.g., 10-400 µm, 10-300 µm, 10-250 µm, 10-200 µm, 10-150 µm, 10-100 µm, 10-80 µm, 10-60 µm, 10-40 µm, 20-500 µm, 40-500 µm, 60-500 µm, 80-500 µm, 100-500 µm, 150-500 µm, 200-500 µm, 250-500 µm, 300-500 µm, 400-500 µm, 100-400 µm, 100-300 µm, 200-400 µm, or 200-300 µm).

In some examples, the hydrogel capsule bead comprises a diameter of 10-500 µm (e.g., 10-400 µm, 10-300 µm, 10-250 µm, 10-200 µm, 10-150 µm, 10-100 µm, 10-80 µm, 10-60 µm, 10-40 µm, 20-500 µm, 40-500 µm, 60-500 µm, 80-500 µm, 100-500 µm, 150-500 µm, 200-500 µm, 250-500 µm, 300-500 µm, 400-500 µm, 100-400 µm, 100-300 µm, 200-400 µm, or 200-300 µm). For example, the hydrogel capsule bead diameter is at least 20 µm (e.g., at least 20, 30, 35, 40, 45, 50, 55, 60, 65, 70, 75, 80, 85, 90, 95, 100 µm, or greater).

In some embodiments, to encapsulate single cells in hydrogel capsules, e.g., with a diameter ranging from 10 to 100 µm, calcium (or other divalent or trivalent cations) carbonate nanoparticles are adsorbed to cell membrane, washed out, and mixed with alginate (or other crosslinkable biomaterial) solutions. For example, the mixture is then passed through a microfluidic device to form an emulsion comprising microparticles that contain cells. The hydrophobic phase contains oil, e.g., fluorocarbon oil, mixed with a surfactant and an acid, e.g., acetic acid. The acid, e.g., acetic acid, releases the divalent cation from the salt, e.g., carbonate, thereby ionically crosslinking alginate in the presence of cells. In some cases, a chemical such as perfluoro-1-octanol is then used to break the emulsion and isolate the aqueous phase that contains single cells encapsulated in hydrogel microparticles. This method may yield about 50% of hydrogel capsules that contain single cells with the cell viability after encapsulation of at least 10%, e.g., at least 10, 20, 30, 40, 50, 60, 70, 80, 90 or higher. For example, as shown in FIG. 7, this method may yield cell viability after encapsulation of about 50%, based on flow cytometry analysis.

In some cases, before encapsulation, the polymer, e.g., alginate, agarose, or gelatin, is mixed with naturally occurring extracellular matrix proteins, such as collagen, fibronectin, and/or laminin.

In accordance with the method, 50 or fewer cells (e.g., 50, 40, 30, 20, 15, 10, 9, 8, 7, 6, 5, 4, 3, 2, or fewer cells) are encapsulated in the hydrogel capsule bead. In one embodiment, one cell is encapsulated in the hydrogel capsule bead. Exemplary cells include a mesenchymal stem cell (MSC), a pre-adipocyte cell, or an endothelial cell. Multiple different cell types are suitable for encapsulation by the methods described herein. For example, the encapsulation yield, efficiency, and long-term viability of mesenchymal stem cells (MSCs) (e.g., D1 s, which are a murine MSC line), pre-adipocyte cells (which support differentiation of embryonic stem cells into hematopoietic stem cells), and human outgrowth endothelial cells (OECs) are described in the Examples.

As shown in the results herein, cells were encapsulated in hydrogel capsules were as small as about 30 microns in diameter, such that the hydrogel layer around encapsulated cells averaged about 4.8 µm in thickness. The thickness was as thin as about 0.8 um in some areas. There was no region in which the hydrogel layer around the cell was absent. This is equal in size to cell-encapsulating hydrogel capsules fabricated in a high-throughput manner (see, e.g., Park et al. Lab Chip 14(2014):1873-1879), and roughly half the size of the smallest hydrogel capsules demonstrated thus far with non-cancerous cells (see, e.g., Martinez et al. *Macromol. Biosci.* 12, 946-951 (2012)). The hydrogel capsules presented here are also smaller than those reported using photolithography, the smallest of which are 50 µm in diameter (see, e.g., Liu et al. *Sci. China. Chem* 55, 494-501

(2012)). The smaller hydrogel capsule size provided by the invention is beneficial in a number of ways. Constructs assembled from cells encapsulated in smaller hydrogel capsules have a higher maximal cell density. The thinner gel layer improves diffusion of nutrients to the cells as well as signaling and communication between cells. Also, smaller hydrogel capsule sizes make cell injection therapies easier and more feasible by permitting encapsulated cells to enter blood vessels of smaller diameter.

As described in the Examples, the variation in polymer content of cell-encapsulating hydrogel capsules was assessed by flow cytometry, and hydrogel capsule size variation was assessed by microscopy. The variability in empty hydrogel capsule size was similar to values obtained in previous studies on the fabrication of monodisperse beads and hydrogel capsules. As unencapsulated cells were found to have a CV in diameter of 0.23, it is likely that greater variation in polymer content and size in cell-encapsulating hydrogel capsules were due to the presence of cells. Cell-encapsulating hydrogel capsules exhibited a quasi-monodisperse size distribution (see, e.g., de la Vega et al. Nanomedicine (Lond). 8.2(2013):265-85). This finding demonstrates that encapsulated cells are exposed to similar extracellular environments, which is useful for studies assessing cell-cell variability on a single cell level.

As described in the Examples, a high encapsulation yield was achieved by pre-coating cells with divalent cation nanoparticles (e.g., calcium carbonate nanoparticles). The exact yield varied with cell type, but was consistently an order of magnitude higher than the yield following direct injection of non-coated cells into a microfluidic device.

Encapsulation of cells into droplets has been found to follow a Poisson distribution, $$P(k)=\lambda^k e^{-\lambda}/k!$$

where $P(k)$ is the fraction of droplets expected to contain $k$ cells, and $\lambda$ is the average number of cells per drop, which is affected by droplet size and cell density. The actual fraction of hydrogel capsules with D1 cells encapsulated by direct injection (0.073) was slightly lower than the expected value predicted with a Poisson process (0.087). Encapsulation yields of OECs (0.028) and OP9s (0.066) with the direct injection process were slightly higher than those predicted by a Poisson process (0.024 and 0.057, respectively). See, e.g., FIGS. 18E-F. Direct injection encapsulation yields were similar to Poisson distribution prediction. This demonstrates that most alginate droplets crosslinked and that the encapsulation yield was determined by droplet size and cell density. However, by preventing the cross-linking of non-cell containing droplets via the cation nanoparticle pre-coating step, the fraction of hydrogel capsules containing cells was greatly enriched without increasing hydrogel capsule size or cell density. See, e.g., FIG. 18A-F. Few studies have been conducted with the aim of improving encapsulation yield either in liquid droplets or in hydrogels, and attempts to address this issue in the past utilized two-step processes (see, e.g., Wu et al. *Biomed Microdevices* 15, 553-560 (2013)) or low-throughput approaches. The methods provided herein are advantageous for approaches or compositions that require a pure population of cell-encapsulating hydrogel capsules.

The impact of polymer molecular weight (MW) on cell behavior, e.g., cell division and egress from encapsulating hydrogel capsules, is described herein. Different MW of polymer (e.g., alginate) were used to modulate cell division within and cell egress from hydrogel capsules. Exemplary MW of polymer (e.g., alginate) suitable for use in accordance with the compositions and methods described herein include MW of at least 50 kDa (e.g., at least 50, 75, 100, 125, 150, 175, 200, 230, 250, 260, 275, 300, 350, 400, 450, 500, or greater). Other MWs of polymers are, e.g., 50-500 kDa (e.g., 50-400 kDa, 50-300 kDa, 50-250 kDa, 50-200 kDa, 50-150 kDa, 50-100 kDa, 100-500 kDa, 100-400 kDa, 100-300 kDa, or 100-250 kDa). For example, the MW of a polymer (e.g., alginate) is 54 kDa, 139 kDa, or 232 kDa.

Higher MW polymers (e.g., alginates) decreased cell egress from and cell division within each hydrogel capsule bead. Mechanical testing revealed that higher MW (e.g., about 232 kDa) polymer (e.g., alginate) hydrogel capsules had a greater elastic modulus than hydrogel capsules fabricated from lower MW polymer (e.g., alginate). This finding shows that the stiffer matrix may have prevented cell-mediated remodeling of the matrix required to make space for cell division and migration. The elastic moduli of hydrogel capsules described herein were an order of magnitude lower than that of large, bulk hydrogels with the same composition. Moreover, the bulk elastic moduli of the same alginate hydrogels were found to be higher than those obtained through AFM. In some cases, this finding is due to the mechanical behaviors of alginate hydrogels differing on different size scales. In other cases, as the AFM probe is of similar dimensions to pores in the alginate network, a larger tip may be needed to accurately measure alginate hydrogels. The increase of the elastic moduli of cell-encapsulating hydrogel capsules with increasing calcium concentration and increasing polymer weight shows that ECM properties were manipulated in hydrogel capsules to control the behavior of encapsulated cells.

As extracellular matrix (ECM) mechanical properties have been shown to strongly influence cell behavior, modulating hydrogel capsule mechanical properties, e.g., by changing the polymer MW, provides a means to control the behavior of encapsulated cells. In some examples, divalent cation (e.g., calcium) treatments were used to alter matrix mechanics after fabrication. For example, cation (e.g., calcium) concentration is used to further modulate the elastic moduli of cell-encapsulating hydrogel capsules after the encapsulation process. For example, the results described herein show that addition of divalent cation (e.g., calcium) to the cell-encapsulated hydrogel capsules after the hydrogel capsule formation increased the elastic moduli. See, e.g., FIG. 18L.

Since hydrogels composed of proteins native to the body, e.g., collagen and fibrin, possess properties lacking in alginate alone, the fabrication of collagen-alginate and fibrin-alginate hybrid hydrogel capsules using the methods described herein was also developed. As described in the Examples, cell-encapsulating hybrid hydrogel capsules made of collagen and alginate, or fibrin and alginate, were fabricated. The two components of each hydrogel capsule (e.g., alginate and collagen, or alginate and fibrin) were evenly distributed within/among hydrogel capsules, and the resultant hydrogel capsules supported cells in long-term culture. Some phase separation of the alginate in fibrin-alginate hydrogel capsules was observed, likely due to the natural calcium-binding properties of fibrinogen. The alginate polymers were evenly distributed on a larger size scale. Greater variation in hydrogel capsule composition was observed in fibrin-alginate hydrogel capsules than collagen-alginate hydrogel capsules. This is likely due to the rapid fibrin cross-linking at the junction of the two aqueous phases affecting the laminar flow of the two polymer components. The fibrin-alginate hydrogel capsules were also significantly poorer in maintaining cell viability, likely due to fibrin formation being insufficiently rapid to prevent cell exposure to the oil-surfactant phase. Consistently, cells encapsulated in fibrin-only hydrogel capsules, which were made with a higher concentration of thrombin, showed higher viability. The ability to fabricate cell-encapsulating hydrogel capsules of different polymers and different combinations of polymers expands the potential applications of hydrogel capsules, for example to wound healing therapies (see, e.g., Gorodetsky et al. *J. Invest. Dermatol.* 112, 866-872 (1999)). Hybrid hydrogel capsules combine the properties of two types of polymers. Because the protein network (e.g., collagen or fibrin network) of hybrid hydrogel capsules maintains structural integrity to some extent independently of the alginate portion, the hybrid hydrogel capsules are advantageous in that they permit switching of the cell microenvironment from hybrid to unitary using protein digestion (e.g., to digest the protein network) or divalent ion (e.g., calcium) chelation (e.g., to remove the alginate crosslinks).

Accordingly, also provided herein is a composition comprising hybrid hydrogel capsules, wherein the hydrogel comprises a first polymer and a second polymer, wherein each of the hybrid hydrogel capsules comprise 50 cells or fewer, where the microgel comprises a diameter or longest dimension of 500 μm or less, and where the cells are fully surrounded by a layer of hydrogel.

In some embodiments, the first polymer is a polysaccharide, e.g., alginate. In some cases, the second polymer is a protein, e.g., collagen or fibrin.

A method for making hybrid microgels may involve the following steps:

a) providing a microfluidic device comprising intersecting open channels;

b) mixing a divalent cation nanoparticle with cells, a first polymer (e.g., polysaccharide, such as alginate), and a second polymer (e.g., protein, such as collagen or fibrin) to produce an aqueous phase liquid;

c) providing a nonaqueous phase liquid comprising an oil and an acid;

d) injecting the aqueous phase liquid into a channel of the device while simultaneously injecting the nonaqueous phase into a separate channel of the device to form an emulsion; and e) contacting the emulsion with a cell-compatible solution to form an individual polymeric microgel bead comprising a cell encapsulated within the microgel.

In some embodiments, the method further comprises a step of incubating the aqueous phase liquid and nonaqueous phase in the device as an emulsion for a specified period of time (e.g., at least 15 s, e.g., at least 15 s, 30 s, 1 min, 2 min, 4 min, 6 min, 10 min, 20 min, 30 min, 45 min, 60 min, 1.5 h, or more) before contacting the emulsion with a cell-compatible solution. In some cases, step d) of the method is performed at a temperature of about 30-40° C., e.g., about 30° C., 31° C., 32° C., 33° C., 34° C., 35° C., 36° C., 37° C., 38° C., 39° C., or 40° C.

In some examples, the second polymer is present in a neutral-pH liquid form.

In some examples, the injection step b) is performed at a temperature of 10° C. or less (e.g., 10, 8, 6, 4° C., or less).

As discussed in the Examples, the osteogenic differentiation potential of encapsulated cells (e.g., D1 MSCs) assembled in a microwell-containing device (e.g., PDMS microwells) was tested. PDMS microwells were capable of templating and culturing singly encapsulated cells. The resultant assemblages had similar densities across microwell sizes. Deeper wells prevented sample loss from the larger-diameter microwells during washing and media change steps. Two-dimensional micropatterning studies have linked increased homotypic cell-cell contact in MSCs with increased differentiation (Tang et al. *Biomaterials* 31, 2470-76 (2010); and Wang et al. *J Biomed Mater Res Part A.* 101A(12), 3388-95 (2013)).

A comparable relationship between cell number and differentiation was found in the microwell assemblages in the results herein. The use of microwells to assemble and culture encapsulated cells improves techniques for fabricating microscale tissues. Although bioprinting techniques can pattern single cells with high spatial resolution on a two-dimensional (2-D) surface, cells cultured in 2-D do not always behave in a way that accurately reflects their behavior in native 3D environments. Printing of hydrogel encapsulated cells, for example, can combine high spatial resolution with a more relevant 3D environment. Moreover, as the PDMS microwells remain open to addition of other cells or soluble factors, the microwell-templated assemblages are a useful platform for co-culture experiments with timed entries, e.g., for drug screens.

Accordingly, the invention also provides a device comprising a microwell, where the microwell comprises a hydrogel capsule or hybrid hydrogel capsule described herein. For example, the microwell comprises a diameter of 25 um to 500 um. In other examples, the microwell comprises a surface area of about 400,000 $\mu m^2$ to about 600,000 $\mu m^2$ (e.g., 400,000-550,000 μm, 400,000-500,000 μm, 450,000-600,000 μm, 500,000-600,000 $\mu m^2$). In some cases, the microwell comprises a depth of at least 100 μm (e.g., at least 100 μm, 150 μm, 200 μm, 250 μm, 300 μm, 350 μm, 400 μm, 450 μm, 500 μm or greater). For example, the microwell comprises 1 to 50 cells, e.g., 1-40, 1-35, 2-50, 2-40, 2-37, 2-35, 2-30, 3-50, 3-40, 3-37, 3-35, 3-30, 5-50, 5-40, 5-35, 5-30, 10-50, 10-40, 10-35, or 10-30 cells.

In some embodiments, the device comprises polydimethylsiloxane (PDMS). For example, the device is useful as a template for cell culture or tissue growth, e.g., microscale tissue fabrication.

III. Methods of Using Hydrogel Capsules Containing Cells

The present invention provides methods for delivering cells and protein factors that may be secreted by the cells, to a subject in need thereof, as well as methods for treating subjects, e.g., subjects having a cardiovascular disease or an immunological disorder, using the hydrogel capsules of the invention.

Delivering cells and their secretions to the body remains a major challenge due to rapid clearance of exogenous cells by physical and immune barriers (Yoo et al., 2011, Nat Rev Drug Discov 10, 521-535). The ability to control the shielding of exogenously administered cells from the body's natural clearance mechanism can potentially lead to significant improvement in the in vivo delivery of cells and biologics that the cells produce. While a bulk crosslinked hydrogel has been used for this purpose (Nicodemus and Bryant, 2008, Tissue Eng Part B Rev 14, 149-165), it is difficult to inject the bulk gel into the body, and the administration route is generally limited to subcutaneous. The compositions of the invention comprising hydrogel capsules overcome this challenge, as the hydrogel capsules formed from a crosslinked hydrogel encapsulate individual cells so that they can be delivered in the body using a wide range of injection routes. In addition to improving cell delivery, physical and chemical properties of the hydrogel capsules can be altered to direct cellular behavior in vivo for diagnostic and therapeutic purposes.

Since the first human bone marrow transplantation (BMT) (Thomas et al., 1957, N *Engl J Med* 257, 491-496) and the revelation of hematopoietic stem cell/progenitors (HSC/Ps) by clonal assay (Becker et al., 1963, *Nature* 197, 452-454), HSC/Ps have become an intense focus of research to improve sustained in vivo regeneration and ex vivo production of blood for patients. Lamins have been described to regulate cell trafficking and lineage maturation of adult human hematopoietic cells. See, e.g., Shin et al. *Proc. Natl. Acad. Sci.*, 2013 Nov. 19; 110(47):18892-7, incorporated herein by reference. Contractile forces have been shown to sustain and polarize hematopoiesis from stem and progenitor cells. See, e.g., Shin et al. Cell Stem Cell. 14, 1-13 (2014), incorporated herein by reference. Also, myosin-II inhibition and soft 2D matrices have been shown to maximize multinucleation and cellular projections typical of platelet-producing megakaryocytes. See, e.g., Shin et al. Proc. Natl. Acad. Sci. 2011 Jul. 12; 108(28):11458-63, incorporated herein by reference. The bone marrow (BM) 'niche' or 'microenvironment' was proposed to be a basic unit that regulates HSC self-renewal and differentiation (Schofield, 1978, Blood Cells 4, 7-25). It has been suggested that multipotent BM mesenchymal stromal cells (MSCs) provide key regulatory signals to program hematopoiesis, based on studies with cultures derived from the adherent fraction of the BM stroma (Dexter et al., 1977, J Cell Physiol 91, 335-344; Friedenstein et al., 1976, Exp Hematol 4, 267-274). A number of studies explored the ability of this 2D stromal culture system or isolated growth factors from the stroma to expand HSC/Ps ex vivo, but no methods have been described that are sufficient to preserve long-term repopulating HSCs and to achieve clinically relevant effects (Broxmeyer, 2011, Cell Prolif 44 Suppl 1, 55-59).

Limitations of using MSCs to facilitate clinical blood production are in part due to at least two issues. First, MSCs are not well defined at a clonal level. For example, MSCs need to be better defined at a clonal level using a serial transplantation assay to assess their capability of forming a new BM niche upon subcutaneous implantation (Bianco et al., 2013, Nat Med 19, 35-42). Recent studies revealed human BM MSCs as CD146+(Sacchetti et al., 2007, Cell 131, 324-336) and Nestin+(Pinho et al., 2013, J Exp Med. 210(7): 1351-1367) cells. These purified cells expanded HSC/Ps ex vivo in a paracrine manner (Isern et al., 2013, Cell Rep 3, 17141724). Second, rigid plastic dishes have been used in many past studies, such dishes do not reflect the native BM milieu, which may provide necessary cues for MSCs to secrete appropriate hematopoietic factors. Cells generate contractile forces via actomyosin, and they pull on and respond to the mechanical properties of the substrates they are grown on, followed by the activation of mechanosensitive transcription factors (Discher et al., 2005, Science 310, 1139-1143). The in situ BM exhibits heterogeneous matrix stiffness measured in Young's modulus (E, unit: Pa). The central marrow is generally soft (<0.3 kPa), while the osteoid is rigid (~1,000 kPa), but much less than plastic (~GPa) (Shin et al., 2014, Cell Stem Cell 14, 81-93). Using hydrogels with tunable physical properties, MSCs specify their lineages based in part on the stiffness of the substrate they are grown on in both 2D (Engler et al., 2006, Cell 126, 677-689) and 3D (Huebsch et al., 2010, *Nat Mater* 9, 518-526).

Cells secrete molecules either directly into the extracellular space or through small extracellular vesicles, which are made up of exosomes (40-200 nm in diameter) and/or microvesicles (~1 μm or greater in diameter) (Raposo and Stoorvogel, 2013, *J Cell Biol* 200, 373-383) or other types of microparticles (such as platelets and apoptotic bodies). For example, microvesicles are vesicles derived from cells, e.g., containing biological material. For example, microvesicles are at least 1 μm in diameter (e.g., at least 1, 2, 3, 4, 5, 6, 7, 8, or 9 μm) and are, e.g., smaller than a cell (e.g., 10 μm or less, e.g., 10, 9, 8, 7, 6, 5, 4, 3, 2 μm, or less). Microparticles, e.g., platelets, are about 1-7 μm in diameter, e.g., 1, 2, 3, 4, 5, 6, or 7 μm. In the hematopoietic system, recent studies described that exosomes released from MSCs impact blood cancer cell proliferation (Roccaro et al., 2013, J Clin Invest 123, 1542-1555), but their roles in normal hematopoiesis remain unknown. In some cases, actomyosin contractile forces drive the final factor release step at the cell membrane (Masedunskas et al., 2011, Proc Natl Acad Sci USA 108, 13552-13557; Muralidharan-Chari et al., 2009, Curr Biol 19, 1875-1885). Cells pulling on the stiff substrate experience high plasma membrane tension generated by actomyosin forces (Engler et al., 2006, Cell 126, 677-689), and increased membrane tension activates exocytosis (Gauthier et al., 2011, Proc Natl Acad Sci USA 108, 14467-14472). However, prior to this disclosure, it was unclear whether substrate stiffness controls factor secretion from MSCs.

Human bone marrow (BM) generates $10^5$ to $10^6$ nucleated blood cells, anucleated red blood cells, and platelets every second. A single stem cell can generate the entire blood hierarchically, and this ability is clinically important to improve therapies with hematopoietic stem cell and progenitors (HSC/Ps). HSC/Ps are regulated by BM niches, which are made up of mesenchymal stromal cells (MSCs) and their lineages. MSCs generate force through cytoskeletons, engage extracellular matrix (ECM), and sense the local matrix stiffness. Matrix stiffness regulates lineage differentiation and migration of MSCs, but the role of matrix stiffness in other force-dependent biological functions has been unclear. MSCs secrete various soluble factors that support hematopoiesis, and cytoskeletal forces regulate exocytosis. The present invention provides methods to harness matrix stiffness, e.g., of hydrogels used to encapsulate cells, to control secretion of soluble factors from MSCs, which in turn, e.g., influences hematopoiesis in a paracrine manner.

The stiffness of the hydrogels encapsulating cells in the compositions of the invention may be altered to regulate release of protein factors secreted from the cells. For example, the hydrogel stiffness may be altered to regulate secretion of hematopoietic factors from MSCs that may regulate hematopoiesis. To induce mechanical triggering of paracrine release from MSCs in vivo and sustainably deliver factors that impact BM resident HSC/Ps in vivo, a microfluidics method is described herein that encapsulates individual cells, e.g., MSCs, in micro-hydrogel droplets so that they can be infused in an intravenous or intrabone route (FIG. 1).

The stiffness and viscoelasticity of materials, such as the hydrogels described herein, are determined by applying a stress (e.g., oscillatory force) to the material and measuring the resulting displacement (i.e., strain). For an applied oscillatory stress or strain, the stress and strain occur in phase in purely elastic materials, such that the response of one (stress or strain) occurs simultaneously with the other. In purely viscous materials, a phase difference is detected between stress and strain. The strain lags behind the stress by a 90 degree (radian) phase lag. Viscoelastic materials have behavior in between that of purely elastic and purely viscous—they exhibit some phase lag in strain. The storage modulus in viscoelastic solid materials are a measure of the stored energy, representing the elastic portion, while the loss modulus in viscoelastic solids measure the energy dissipated as heat, representing the viscous portion. In some examples, the hydrogels described herein are characterized as viscoelastic.

The elastic modulus (also called Young's modulus) is a measure of stiffness of a material, such as a hydrogel. The elastic modulus is the slope of the initial straight portion, e.g., the first 5-10% of strain, of a stress-strain curve. The modulus is the ratio of the change in stress to the change in strain expressed as a fraction of the original length. The elastic modulus has units of Pa (or N/m$^2$ or m$^{-1}$·kg·s$^{-2}$). For viscoelastic materials, the measured elastic modulus can depend on the timescale of the stress-strain measurement, since viscoelastic materials can exhibit stress relaxation leading to a decrease in the measured modulus for measurements taken over longer timescales. For materials that exhibit significant stress relaxation, the initial elastic modulus is defined as the elastic modulus for a stress-strain measurement that is performed over a timescale at which there is minimal stress relaxation. The initial elastic modulus can be determined using standard methods available in the art, e.g., by a compression test or rheology. For example, a hydrogel is compressed, e.g., to 15% strain, e.g., with a deformation rate of about 1 mm/min. With 15% compression, the stress versus strain relations of the hydrogels are almost linear, and the slope of the initial portion (first 5-10% strain) of the stress strain curves gives the initial elastic modulus.

For example, the stiffness of a hydrogel described herein can be tuned/modulated over the range of typical tissues, e.g., from liquid (blood) to soft tissues to harder tissues (e.g., bone). For example, the stiffness of a hydrogel can be tuned over the range of soft tissues (heart, lung, kidney, liver, muscle, neural, etc.) from an elastic modulus of ~20 Pascals (fat) to ~100,000 Pascals (skeletal muscle). Bone marrow is about 300 Pa. An osteoid is about 34 kPa. Different tissue types are characterized by different stiffness, e.g., normal brain tissue has a shear modulus of approximately 200 Pascal. For example, blood is characterized by stiffnesses of less than 1 kPa. Brain tissue is characterized by stiffnesses of about 1 kPa. Muscle has a stiffness of about 10 kPa. Collagenous bone has a stiffness of about 100 kPa. Blood, bone marrow, and neuronal cells have a physiological stiffness of about 0.1 kPa to about 1 kPa, adipose cells have a physiological stiffness of about 0.1 kPa to about 3 kPa, liver, kidney, fat, lung, and endothelial cells have a physiological stiffness of about 1 kPa to about 10 kPa, muscle and heart cells have a physiological stiffness of about 10 kPa to about 20 kPa, and cartilage and bone cells have a physiological stiffness of about 20 kPa to about 500 kPa. For example, a hydrogel described herein comprises a stiffness that matches that of the normal stiffness of a cell/tissue type described above, e.g., a cell type that is encapsulated into the hydrogel.

BM MSCs secrete molecules not only directly to the extracellular space but also through vesicles. Effects of matrix stiffness on the extracellular vesicle release from MSCs are described herein. For example, matrix stiffness affects the quantity of vesicles released from MSCs and/or the content of the vesicles released from MSCs. In some cases, the quantity and content of these vesicles impacts HSC/P differentiation, e.g., in vitro and/or in vivo. For example, the protein quantity and contents of the vesicles and the conditioned media from MSC cultures are determined. In some examples, mechano-sensitive transcription is required for matrix stiffness-dependent release of soluble factors. In some cases, RNA interference against Yes-associated protein and serum response factor in MSCs is used to determine whether mechano-sensitive transcription is required for the matrix stiffness-dependent release of the soluble factors. In addition, small molecules against the myosin pathway are used to determine the involvement of contractile forces in the stiffness dependent release of soluble factors. Exemplary small molecules that inhibit the myosin pathway include (+/−)-blebbistatin (EMD Biosciences), reversine, ML-7, and Y-27632 (Sigma).

In some examples, the invention also provides a method of promoting secretion of a protein factor, e.g., a hematopoietic factor, from a cell (e.g., a MSC, HSC or progenitor thereof, or endothelial progenitor) through release of vesicles, comprising contacting the cell with a hydrogel micro-carrier described herein. In other examples, the invention provides a method of promoting secretion of a protein factor, e.g., a hematopoietic factor, from a cell (e.g., an MSC, HSC or progenitor thereof, or endothelial progenitor) through direct secretion (e.g., without exosome release into an extracellular space), comprising contacting the cell with a hydrogel micro-carrier described herein. In some examples, the invention provides a method of preferentially promoting secretion of a hematopoietic factor from a mesenchymal stem cell (MSC) through release of vesicles as opposed to other mechanisms of secretion (e.g., direct secretion), comprising contacting the MSC with a hydrogel micro-carrier described herein. In some examples, the vesicles comprise a diameter of at least about 1 μm, e.g., at least about 1, 2, 3, 4, 5, 6, 7, 8, 9, 10, 20, 40, 60, 80, or 100 μm. In other examples, the vesicles comprise a diameter of 1000 nm or less (e.g., 1000, 900, 800, 500, 250, 150, 100, 80, 60, 50, 40, 30, 20, 10 nm or less).

The invention is based in part on the discovery of how matrix mechanics regulate paracrine release. This knowledge, in addition to the biomaterials and microtechnologies described herein, are used to develop an infusible microvesicle that can mechanically trigger sustainable factor secretion from cells, e.g., MSCs. MSCs secrete factors, including factors that treat heart damage/disease and factors that regulate hematopoiesis. In one example, the methods and hydrogels described herein produce mechano-sensitive factors from MSCs capable of programming hematopoiesis both ex vivo and in vivo. The hydrogel capsules and methods described herein are also applicable to the treatment and prevention of hematopoietic and cardiovascular diseases. For example, the hydrogel capsules and methods described herein are useful for the improvement of hematopoietic engraftment, e.g., for bone marrow transplantation, and the exploration of the MSC secretome is applicable to the treatment of cardiovascular and other diseases. In some cases, MSCs release proteins that are known to treat myocardial infarction, hypertrophy, and arrhythmia. For example, such factors include cardiovascular regeneration factors, e.g., vascular endothelial growth factor (VEGF), stromal cell derived factor 1 (SDF-1), tumor necrosis factor-inducible gene 6 protein (TSG-6), interleukin-6 (IL-6), interleukin-8 (IL-8), basic fibroblast growth factor (bFGF or FGF-2), insulin-like growth factor 1 (IGF-1), hepatocyte growth factor (HGF), Thrombospondin-4, secreted frizzled-related protein 2 (Sfrp2), matrix metalloproteinase 9 (MMP-9), tissue inhibitior of metalloproteinases (TIMP) metallopeptidase inhibitor 2 (TIMP-2), monocyte chemotactic protein 1 (MCP-1), thrombospondin 1 (TSP-1), chemokine (C-X-C motif) ligand 6 (CXCL6), or interferon gamma-induced protein 10 (IP-10).

In some examples, an MSC is included in/on a hydrogel micro-carrier and administered to a subject intravenously or directly into a tissue, e.g., a heart tissue. For example, by including, e.g., encapsulating, a MSC in a hydrogel microcarrier and directly injecting the micro-carrier into a heart tissue, the factors from MSCs are secreted in a prolonged and controlled manner to treat heart conditions.

The present invention provides infusible hydrogel capsules that mechanically trigger hematopoietic factor release from encapsulated MSCs in vivo. MSCs likely secrete a number of factors that act together to regulate hematopoiesis. This invention harnesses these mechano-sensitive secretory factors to program BM resident HSC/Ps in vivo by using a microfluidics-based technique to achieve single cell encapsulation of MSCs. In particular, alginate gel droplets, e.g., with a size appropriate for intravenous and intrabone infusion, are fabricated by varying cross-linker (e.g., divalent cation, e.g., $Ca^{2+}$) and gel concentrations to achieve optimal mechanical properties for MSCs to induce HSC expansion. The stiffness and size of the droplets are varied in order to optimize in vivo clearance kinetics of the droplets after infusion. In some cases, factors released from MSCs, e.g., the MSCs encapsulated in the hydrogel droplets described herein, enhance human hematopoiesis. For example, such enhancement of human hematopoiesis is detected by transplantation of immunocompromised xenograft mice with human BM $CD34^+$ cells, followed by infusion of MSC droplets and standard characterization of human hematopoietic reconstitution.

In some cases, the hydrogel capsules and methods described herein are useful for generation of blood, e.g., for transfusions. There is a need for adequate supplies of blood components, including red blood cells (RBCs). Methods have been described for producing mature human RBCs having the characteristics of native adult RBCs from hematopoietic stem cells of diverse origins, e.g., blood, bone marrow, or cord blood. See, e.g., Douay et al. Transfus. *Med. Rev.* 2007, 21(2):91-100. The invention provides a method of generating RBCs in vitro/ex vivo by using matrix stiffness-modulated MSCs that stimulate hematopoiesis by HSCs by paracrine signaling between MSCs and HSCs. For example, the invention includes a method comprising providing a hydrogel comprising a MSC and a stiffness, e.g., where the stiffness of the hydrogel promotes secretion of hematopoietic factors from the MSC. In some examples, the stiffness preferentially promotes secretion of hematopoietic factors via release of vesicles as opposed to other mechanisms of secretion. The method optionally comprises a step of collecting an extracellular content, e.g., secreted substance, from the MSC. The method further comprises contacting a secreted substance from the MSC with a HSC. In some cases, the hydrogel comprising a MSC is located in the same closed container as the HSC, e.g., such that a secreted substance from the MSC is capable of coming into contact with the HSC, e.g., by diffusion through a liquid (e.g., culture medium), e.g., via diffusion through a pore of a membrane that separates the MSC from the HSC. For example, the method preserves long-term repopulating HSCs that are capable of producing blood cells, e.g., RBCs. For examples, the method increases the number of HSCs in culture, e.g., by promoting the growth rate and/or survival of HSCs.

In some embodiments, the invention also provides a method of enhancing secretion of a hematopoietic factor by a MSC by contacting the MSC with a 2-dimensional or 3-dimensional hydrogel described herein, e.g., comprising a stiffness that enhances secretion of the hematopoietic factor by the MSC.

Secretion is the process for releasing and/or oozing a substance, e.g., a chemical or biological substance/molecule, from a cell or gland. Several mechanisms exist for secretion of biological substances, e.g., proteins, from cells. For example, proteins targeted for secretion into the extracellular space of a cell are translated at the rough endoplasmic reticulum (ER), where they are glycosylated, folded, and shuttled into the Golgi apparatus. In the Golgi, glycosylation of the protein is modified and posttranslational modifications occur. The proteins to be secreted are shuttled into secretory vesicles that travel to the cell membrane, where the vesicle fuses with the cell membrane in a process called exocytosis. In some types of secretion, the contents of the vesicle, e.g., including secreted proteins, are dumped into the extracellular space. In other types of secretion, proteins are secreted by release of exosomes/vesicles containing the protein(s) from a cell. This process involves endosomes themselves invaginating their membrane. As the invaginations break off, they produce vesicles within vesicles, called multivesicular bodies. When these vesicles fuse with the cell's plasma membrane, these tiny (e.g., 40-100 nm) internal vesicles—called exosomes—are secreted. Yet other mechanisms of secretion can involve, e.g., direct translocation of a protein across a cell membrane, e.g., through transporters in the membrane. Another secretion mechanism is lysosomal secretion. Yet another secretion mechanism involves release of molecules, e.g., proteins, from cells by mechanical or physiological wounding, e.g., through non-lethal, transient pores in the cell membrane.

The secretion of protein factors from a cell occurs by exosomal release or by direct secretion of the protein factor into an extracellular space of the cell, e.g., an MSC. In some cases, the hydrogel encapsulating cells in the compositions of the invention promotes exosomal release of the hematopoietic factor by the MSC. In other cases, the hydrogel promotes direct secretion of the hematopoietic factor into an extracellular space of the MSC. In some examples, the hydrogel preferentially promotes exosomal release as opposed to direct secretion of the hematopoietic factor by the MSC. In other examples, the hydrogel preferentially promotes direct secretion of the hematopoietic factor as opposed to exosomal release of the factor.

For example, the secretion occurs by exosomal release or by direct secretion of the hematopoietic factor into an extracellular space of the MSC. In some cases, the hydrogel promotes exosomal release of the hematopoietic factor by the MSC. In other cases, the hydrogel promotes direct secretion of the hematopoietic factor into an extracellular space of the MSC. In some examples, the hydrogel preferentially promotes exosomal release as opposed to direct secretion of the hematopoietic factor by the MSC. In other examples, the hydrogel preferentially promotes direct secretion of the hematopoietic factor as opposed to exosomal release of the factor.

The invention further features a method of enhancing HSC engraftment following bone marrow transplantation or HSC transplantation in a subject by administering to the subject a 2-dimensional or 3-dimensional hydrogel described herein, e.g., comprising a stiffness and a MSC.

Bone marrow is the soft, spongy tissue found inside bones that comprises stem cells, e.g., hematopoietic stem cells (HSCs). Bone marrow is the medium for development and storage of most of the body's blood cells.

Bone marrow transplant (BMT) is a therapy used for patients suffering from diseases such as cancer, immunodeficiency disorders, and blood disorders. In some examples, a BMT taking cells normally found in bone marrow (e.g., stem cells), filtering those cells, and administering them to the patient (e.g., where the patient is the same or different person as the donor). In some examples, the BMT transfuses healthy bone marrow cells into a patient after his or her bone marrow has been entirely or partially destroyed by treatment that kills abnormal cells in the patient's body. Such treatments can include cancer therapies, e.g., chemotherapy, radiation, and/or cancer vaccines. For example, BMT has been used to effectively treat diseases such as leukemias, lymphomas, aplastic anemia, immune deficiency disorders, and some solid tumor cancers.

Exemplary cancers include a melanoma, a central nervous system (CNS) cancer, a CNS germ cell tumor, a lung cancer, leukemia, multiple myeloma, a renal cancer, a malignant glioma, a medulloblatoma, a breast cancer, an ovarian cancer, a prostate cancer, a bladder cancer, a fibrosarcoma, a pancreatic cancer, a gastric cancer, a head and neck cancer, or a colorectal cancer. For example, a cancer cell is derived from a solid tumor cancer or hematological/blood cancer. The hematological cancer is, e.g., a leukemia or a lymphoma. A leukemia is acute lymphoblastic leukemia (ALL), acute myelogenous leukemia (AML), chronic lymphocytic leukemia (CLL), small lymphocytic lymphoma (SLL), chronic myelogenous leukemia (CML), or acute monocytic leukemia (AMoL). A lymphoma is follicular lymphoma, Hodgkin's lymphoma (e.g., Nodular sclerosing subtype, mixed-cellularity subtype, lymphocyte-rich subtype, or lymphocyte depleted subtype), or Non-Hodgkin's lymphoma. Exemplary solid cancers include but are not limited to melanoma (e.g., unresectable, metastatic melanoma), renal cancer (e.g., renal cell carcinoma), prostate cancer (e.g., metastatic castration resistant prostate cancer), ovarian cancer (e.g., epithelial ovarian cancer, such as metastatic epithelial ovarian cancer), breast cancer (e.g., triple negative breast cancer), and lung cancer (e.g., non-small cell lung cancer).

In some examples, a BMT or HSC transplant is useful for cures a disease, e.g., a type of cancer or blood disorder. In other examples, a BMT or HSC transplant is useful for replenishing a damaged bone marrow after a treatment, e.g., chemotherapy or radiation. For example, the doses of chemotherapy or radiation required to cure a cancer are so high that a person's bone marrow stem cells are sometimes permanently damaged or destroyed by the treatment. Other times, a person's bone marrow can be destroyed by a disease.

For example, a bone marrow transplant or HSC transplant is used to replace diseased, nonfunctioning bone marrow/HSCs with healthy functioning bone marrow/HSCs, e.g., for conditions such as leukemia, aplastic anemia, or sickle cell anemia. BMT or HSC transplant is also used to regenerate a new immune system in order to fight existing or residual leukemia or other cancers not killed by the chemotherapy or radiation used in the transplant. In addition, BMT or HSC transplant is used to replace the bone marrow and restore its normal function after high doses of chemotherapy and/or radiation are given to treat a malignancy. This process is often called rescue (e.g., for diseases such as lymphoma and neuroblastoma). Also, BMT or HSC transplant is used to replace bone marrow with genetically healthy functioning bone marrow to prevent further damage from a genetic disease process (such as Hurler's syndrome and adrenoleukodystrophy).

Types of BMT include autologous bone marrow transplant, allogeneic bone marrow transplant, or umbilical cord blood transplant. In autologous BMT, the donor is the patient himself or herself. Stem cells are taken from the patient either by bone marrow harvest or apheresis (a process of collecting peripheral blood stem cells), frozen, and then administered to the patient after a treatment. In allogeneic BMT, the donor shares the same genetic type as the patient. Stem cells are taken either by bone marrow harvest or apheresis from a genetically matched donor, e.g., a relative, e.g., a brother or sister. Other donors for allogeneic bone marrow transplants can include a parent or an unrelated donor, e.g., found through national bone marrow registries. In umbilical cord blood transplant, stem cells are taken from an umbilical cord immediately after delivery of an infant. These stem cells reproduce into mature, functioning blood cells quicker and more effectively than do stem cells taken from the bone marrow of another child or adult. The stem cells are tested, typed, counted, and frozen until they are needed for a transplant. A HSC transplant can also involve an autologous HSC or allogeneic HSC.

After BMT/HSC transplant, engraftment occurs, in which the donated cells travel to the bone marrow of the patient and begin producing new blood cells. In some examples, engraftment can be delayed because of infection, medications, low donated stem cell count, or graft failure. New bone marrow may begin making cells in the first 30 days following transplant, but it may take months, even years, for the entire immune system to fully recover after a BMT/HSC transplant. Sometimes, complications occur after transplant that can delay engraftment. Exemplary complications include infections, low platelets (thrombocytopenia) and low red blood cells (anemia), pain (e.g., related to mouth sores and gastrointestinal irritation), fluid overload (e.g. which can lead to pneumonia, liver damage, and high blood pressure), respiratory distress, organ damage (e.g., liver or heart damage), graft failure (e.g., failure of the graft (transplant) to take hold in the marrow), and Graft-versus-host disease (GVHD) (e.g., where the donor's immune system reacts against the recipient's tissue/cells).

In some cases, the hydrogel capsules and methods of the invention mitigate one or more of these complications associated with BMT or HSC transplantation. In other cases, the hydrogels and methods of the invention enhance engraftment of stem cells (e.g., from a bone marrow or HSC transplant), e.g., decrease the time for engraftment after transplantation.

As used herein, autologous refers to donor cells that are provided by the patient himself/herself. Allogeneic refers to donor cells that are of the same species but genetically non-identical to the patient. Related allogeneic refers to cells provided by patient's sibling or other family member. Unrelated allogeneic refers to cells provided by a volunteer donor, e.g., who is not the patient's family member.

A hydrogel is a gel comprising interconnected crosslinked polymer strands. For example, a hydrogel comprises pores, e.g., that can hold passenger molecules/cells. In such a way, the hydrogel can serve as a carrier/delivery vehicle for molecules/cells. A hydrogel micro-carrier is a hydrogel for delivery a passenger molecule/cell that is small enough to be injected/infused into a subject, e.g., through a blood stream of the subject. For example, a hydrogel micro-carrier carries a small number of cells, e.g., 50 or fewer, e.g., 50, 40, 30, 20, 10, 9, 8, 7, 6, 5, 4, 3, 2, or fewer cells. For example, hydrogel micro-carrier carries one single cell. For example, the hydrogel micro-carrier surrounds a cell, e.g., a single cell, on one or more (e.g., all) dimensions of the cell, e.g., the hydrogel micro-carrier encapsulates the cell. In some cases, the hydrogel micro-carrier is in the form of a liquid droplet, e.g., of picoliter volume. For example, the droplet has a volume of about 0.1-1000 pL, e.g., about 1-1000 pL, 1-500 pL, 1-100 pL, 10-500 pL, or 10-100 pL.

Hematopoietic factors are proteins that cause blood cells, e.g., HSCs, to grow and/or mature. For example hematopoietic factors regulate, e.g, enhance, blood production. Exemplary hematopoietic factors include stem cell factor (SCF), interleukin-2 (IL-2), interleukin-3 (IL-3), interleukin-6 (IL-6), interleukin-7 (IL-7), granulocyte-macrophage colony stimulating factor (GM-CSF), granulocyte colony stimulating factor (G-CSF), macrophage colony stimulating factor (M-CSF), erythropoietin, thrombopoietin, collagen-I, interleukin-11 (IL-11), angiopoietin-1, and transforming growth factor-beta (TGF-beta).

In some examples, cell growth/behavior differs relative to the disease state of a given tissue, e.g., the shear modulus (a measure of stiffness) of normal mammary tissue is approximately 100 Pascal, whereas that of breast tumor tissue is approximately 2000 Pascal. Similarly, normal liver tissue has a shear modulus of approximately 300 Pascal compared to fibrotic liver tissue, which is characterized by a shear modulus of approximately 800 Pascal. Growth, signal transduction, gene or protein expression/secretion, as well as other physiologic parameters are altered in response to contact with different substrate stiffness and evaluated in response to contact with substrates characterized by mechanical properties that simulate different tissue types or disease states. In one embodiment, the stiffness of a hydrogel is tuned to enhance hematopoiesis. For example, the stiffness of a hydrogel is tuned to enhance secretion of hematopoietic factors from MSCs.

In accordance with any method described herein, a subject as described herein is a mammal, e.g., a human, dog, cat, horse, cow, pig, goat, sheep, rabbit, or monkey. In some examples, a subject described herein is one who suffers or has suffered from a cancer, immune deficiency disorder, or a blood disease. For example, the cancer comprises a blood cancer or a solid tumor cancer. Exemplary blood cancers include a leukemia, lymphoma, and myeloma. Solid tumor cancers, e.g., comprise an adrenocortical tumor, colorectal carcinoma, breast cancer, lung cancer, ovarian cancer, uterine cancer, endometrial cancer, cervical cancer, gliobastoma, colon cancer, stomach cancer, pancreatic cancer, desmoid tumor, desmoplastic small round cell tumor, endocrine tumor, Ewing sarcoma, hepatocellular carcinoma, melanoma, neuroblastoma, osteosarcoma, retinoblastoma, rhabdomyosarcoma, Wilms tumor, nasopharyngeal cancer, testicular cancer, thyroid cancer, thymus cancer, gallbladder cancer, central nervous system (CNS) cancer, bladder cancer, or bile duct cancer. Exemplary blood diseases include thalassemia, aplastic anemia, and sickle cell anemia. Also, exemplary immune deficiency disorders include X-linked agammaglobulinemia (XLA), severe combined immunodeficiency (SCID disorder), common variable immunodeficiency, alymphocytosis.

In some cases, a subject as described herein has undergone or is undergoing a chemotherapy or a radiation treatment.

In addition to hematopoietic factors, cells, e.g., MSCs, also secrete other factors, e.g., ones that ameliorate myocardial infarction. As such, the invention further provides a method for treating or preventing a cardiovascular disease in a subject in need thereof, comprising administering to the subject a hydrogel described herein, e.g., a 2-dimensional or 3-dimensional hydrogel comprising a stiffness and a mesenchymal stem cell (MSC). For example, the cardiovascular disease comprises coronary artery disease, cardiomyopathy, hypertensive heart disease, heart failure, cor pulmonale, cardiac dysrhythmia, indocarditis, inflammatory cardiomegaly, myocarditis, valvular heart disease, cerebrovascular disease, peripheral arterial disease, congenital heart disease, or rheumatic heart disease. For example, hydrogel micro-carriers that contain MSCs are injected directly to a damaged heart. In some examples, the hydrogel micro-carriers provide prolonged delivery of factors that ameliorate myocardial infarction compared to direct administration of the factors or administration of MSCs that are not encapsulated in hydrogel micro-carriers.

Exemplary factors that promote cardiovascular regeneration, e.g., that ameliorate myocardial infarction, include vascular endothelial growth factor (VEGF), stromal cell derived factor 1 (SDF-1), tumor necrosis factor-inducible gene 6 protein (TSG-6), interleukin-6 (IL-6), interleukin-8 (IL-8), basic fibroblast growth factor (bFGF or FGF-2), insulin-like growth factor 1 (IGF-1), hepatocyte growth factor (HGF), Thrombospondin-4, secreted frizzled-related protein 2 (Sfrp2), matrix metalloproteinase 9 (MMP-9), tissue inhibitior of metalloproteinases (TIMP) metallopeptidase inhibitor 2 (TIMP-2), monocyte chemotactic protein 1 (MCP-1), thrombospondin 1 (TSP-1), chemokine (C-X-C motif) ligand 6 (CXCL6), interferon gamma-induced protein 10 (IP-10). For example, one of more of these factors are secreted by a MSC.

In some cases, the hydrogel comprises 50 or fewer (e.g., 50, 40, 30, 20, 10, or fewer) MSCs. For example, the hydrogel comprises one single MSC.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

The invention will be further illustrated in the following non-limiting examples.

EXAMPLES

The following materials and methods were used in Examples 1-7.

Statistical Analysis.

For the experiments described below, two-tailed student t-test is performed with the data from ≥3 experiments. Multiple group analysis is done using ANOVA. $P<0.05$ is considered statistically significant between control and perturbations.

Sources of Cells and Tissues.

Adult human stem cells from bone marrow are purchased from commercial vendors. Primary mouse tissues are obtained using established mouse strains.

Species/Strain/Age/Sex

Mice, NOD/scid-IL-2Rgc null (NSG, JAX stock 005557). Animals are normally studied between 2-6 months of age. Both sexes are used in the experiments described herein.

Genomic DNA Testing

In some cases, development and breeding of genetically modified animals are not performed with recombinant DNAs.

Peripheral Blood Sampling

For a period up to 5 months after the transplantation, the mice are anesthetized using isoflurane inhalation, and a small amount of blood (50 μL per adult mouse, about 25

~35 g) is sampled from the transplanted mice from the retro-orbital capillary bed once a month. The mice are euthanized afterwards.

Human Bone Marrow (BM) Cell Xenotransplantation

Human BM CD34+ hematopoietic stem cell and progenitors (HSC/Ps), with or without culture, are transplanted either via the intrabone or intravenous route into sublethally irradiated (~250 rads) NSG mice, which is the optimal dosage to keep mice alive in sterile conditions, while clearing enough host mouse blood cells to maintain human donor cells in vivo. Recipient mice are subjected to the transplantation within 8 hours of sublethal irradiation. The animals are fed with 8 mL of antibiotic Septra water for two weeks after cell transplantation. The animals are observed 3 times a week for the duration of each experiment, followed by euthanization. Any sick mice, which show signs of dehydration, hunched posture, or decreased activity will be euthanized. The total blood counts are typically recovered to normal levels in less than two weeks.

Human Mesenchymal Stromal Cell (MSCs) Xenotransplantation

Human MSCs are isolated by plastic adherence and expanded, followed by incorporation into polymer constructs. Up to two cylindrical polymer discs with or without MSCs (1 cm diameter, 0.5 cm height) are implanted subcutaneously per NSG mouse by performing survival surgery. Briefly, mice are anesthetized utilizing ketamine/xylazine injection (80-120 mg/kg ketamine+5-10 mg/kg xylazine per mouse). A small incision (1-3 cm) is then be made through the subcutaneous tissue, and scissors are used to create a small pocket suitable for the implantation. Several stitches (Maxon 7-0, a monofilament synthetic absorbable suture) are placed within the subcutaneous pocket to immobilize the polymer. The incisions are then closed with closure clips (REFLEX™ clips). The animals are allowed to recover from anesthesia and returned to cages. Skin sutures or clips are removed within 10-14 days post-surgery, and the longest duration for implants is 6 months. Human BM CD34$^+$ transplantation in these mice is done in limiting dilution 8 weeks after MSC implantation to test human HSC engraftment in the newly formed ectopic niche.

Anticipated Numbers of Animals

In the studies described herein, the number of animals required per arm is estimated based on prior studies that would be the minimum needed to reach a statistical difference of 0.05 by a Student t-test.

Breeding

Animals are procured from the Jackson Laboratory which provides both naïve NOD-scid-IL-2Rgc null mice. Animals are bred according to standard protocols. If there are 10 breeding pair per year, 10 pair×2 mice/pair (male and female)×2 years=40 mice for breeding purposes.

For the studies involving the quantification of human HSC number by limiting dilution from human BM CD34$^+$ cells cultured in the presence of human BM MSC-conditioned medium, the total number of animals is calculated as follows:

1. Different stiffness for human BM MSCs: soft (1 kPa), intermediate (10 kPa), and stiff (40 kPa) cultured in either undifferentiating or differentiating medium=3×2=6 medium conditions;
2. Undifferentiating or differentiating medium without MSCs=2 medium controls;
3. Different stiffness for human BM HSCs: very soft (0.05 kPa) and soft (1 kPa)=2;
4. The number of limiting dilution doses=3;
5. The number of mice per dose=5; with a total number of animals of (6+2)×2×3×5=240 mice.

For studies involving the subcutaneous implantation of human BM MSCs in polymer scaffolds, followed by the ectopic niche formation and subsequent transplantation with different doses of human BM CD34$^+$ cells to test HSC engraftment in the ectopic niche in vivo, the total number of animals is calculated as follows:

1. Bulk hydrogel with different stiffness for human BM MSCs: soft (1 kPa), intermediate (10 kPa), and stiff (40 kPa)=3 conditions;
2. Single encapsulated MSC droplets mixed in different ratios. soft (1 kPa):stiff (40 kPa)=1:9, 5:5, 9:1=3 conditions;
3. The number of limiting dilution doses=3;
4. The number of mice per dose=5, 2 scaffolds per recipient; with a total number of animals of (3+3)×3×5=90 mice.

Thus, the total number of animals used for the studies described herein is about 40 (Breeding)+240+90=370 mice.

In some examples, an immune-deficient mouse is used to characterize human hematopoietic and mesenchymal cells in vivo. For example, immune-deficient mice represent the only in vivo model for the study of human hematopoietic niche and blood cell formation and for the development of therapeutic strategies for blood disorders. This model is used for the study of bone formation, angiogenesis via human endothelial progenitors in ischemic muscle injury models, and human hematopoietic system reconstitution. Instead of NSG mice, alternative previous generation immuno-deficient mice models, including nude and NOG/SCID mice, can be used.

Mouse models are useful for developing mechanically controlled strategies to form the BM niche and engineer blood formation and for recapitulating the complexity of an animal blood network. In some examples, in vivo studies described herein demonstrate the functionality of HSCs to reconstitute blood long-term, and to induce hematopoietic niche formation by MSCs incorporated in designed polymer constructs. The results herein show that gel/matrix/substrate mechanics play roles in HSC differentiation in vitro. The therapeutic potential of mechanically controlling the BM niche formation to engineer blood formation is further confirmed, e.g., by studying mice xeno-transplanted with human cells. For example, only immune-deficient mice will accept human xenografts. These immune-deficient mice are sensitive to pathogens—as such, mice are handled in a sterile environment, e.g., in a BSL-2 space equipped with double HEPA-filtered microisolator cages. Mice are given irradiated chow and acidified water, and they are housed in microisolator cages contained in ventilated racks. Personnel handling the mice wear gowns, caps, masks, foot coverings and sterile gloves. All manipulations of the mice such as feeding and changing cages are done under a laminar flow hood within the sterile room.

Intrabone or intravenous injections of primary human CD34$^+$-derived cells are performed in mice. In some cases, sublethal irradiation can lower the total blood count for at least two weeks post-irradiation and transplantation. Injected animals are monitored within 24 hours of the injection, and then at least 3 times a week thereafter. Prophylactic Septra water and wet food are provided on the cage floor for all recipient mice for two weeks post-transplantation. If the mice display a marked decreased activity, decreased intake of water and food, and hunched posture, they are euthanized. Mice experiencing weight loss greater than 30% within a 14-day period are sacrificed as well. Euthanasia comprises $CO_2$ narcosis as approved by the Panel on Euthanasia of the American Veterinary Medical Association, and e.g., animals are observed for 15 min afterwards for loss of heartbeat and movement.

Materials and experimental methods used in Examples 8-11 are as follows.

Microfluidic Device and Microwell Fabrication

Soft lithography was used to fabricate microfluidic devices and microwells.

Negative photoresist SU-8 3025 (MicroChem, Newton, Mass.) was deposited onto clean silica wafers to a thickness of 25, 50, 100 or 200 um, and patterned by UV light exposure through a transparency photomask (CAD/Art Services, Bandon, Oreg.). After the photoresist was developed, polydimethylsiloxane (PDMS) (Dow Corning, Midland, Mich.) was mixed with crosslinker (ratio 10:1), degassed, poured, and cured for at least 1 hour at 65° C. For microfluidic devices, the PDMS replicas were peeled off the wafer and bonded to glass slides by oxygen-plasma activation of both surfaces. Microfluidic channels were then treated with Aquapel (PPG Industries, Pittsburgh, Pa.) by passing the solution through the channels, to improve wetting of channels with fluorinated oil. Polyethylene tubing with inner diameter 0.38 mm and outer diameter 1.09 mm and 27 G×½ needles were used to connect channels to plastic syringes (all from Becton Dickinson, Franklin Lakes, N.J.).

PDMS microwell replicates were peeled off of the wafer, and 3D-printed polyurethane structures were glued onto the microwell fields using PDMS. After curing for at least 1 hour at 65° C., microwell-structures were incubated in 70% ethanol for 2 h. Microwell fields were washed with deionized $H_2O$ and treated with 3% Pluronic F68 for 10 minutes under vacuum, followed by two washes with Dulbecco's phosphate buffered solution. Hydrogel capsule-encapsulated cells suspended in complete DMEM were then seeded and allowed to settle by gravitational sedimentation for 1 h.

Alginate Preparation and Formation of Bulk Hydrogels

Sodium alginate with high molecular weight and high guluronic acid content was purchased from FMC Biopolymer (Princeton, N.J.). To produce lower molecular weights alginate, the high molecular weight alginate was irradiated by a 3 Mrad cobalt source. Alginates were covalently coupled with the integrin-binding peptide (Gly)4-Arg-Gly-Ala-Ser-Ser-Lys-Tyr (SEQ ID NO: 1) (Peptides International) and either Fluoresceinamine, isomer I (Sigma-Aldrich) or Lissamine™ Rhodamine B Ethylenediamine (Setareh Biotech).

Bulk alginate hydrogels were fabricated with a calcium sulfate slurry as the calcium source. Alginate was transferred to a 3 mL syringe, and the calcium slurry to another syringe (BD). The two syringes were connected with a female-female Luer lock coupler (ValuePlastics), without introducing air bubbles, and the two solutions were rapidly together with eight pumps of the syringe handles. The alginate was deposited on a glass plate and allowed to cross-link for 45 minutes. Bulk alginate gels were either 1% alginate for lower elastic moduli, or 2% for higher elastic moduli.

Cell Culture

Clonally derived mouse MSCs (D1s) purchased from American Type Cell Culture (ATCC) were expanded subconfluently in high-glucose, 10% fetal bovine serum-supplemented Dulbecco's Modified Eagle media (complete DMEM). OP9s were purchased from ATCC and expanded subconfluently in Alpha Minimum Essential Medium supplemented with 20% fetal bovine serum. OECs were isolated from human cord blood within 12 hours from collection using standard techniques. Colonies were replated and expanded subconfluently in EGM-2MV (Lonza #CC-3202, Walkersville, Md.) media prior to use, and cells were used for studies between passages 5-7.

Encapsulation

Calcium carbonate nanoparticles (CalEssence® 70 PCC) were suspended in complete DMEM buffered with pH 7.7 25 mM HEPES (HEPES-DMEM) (Sigma-Aldrich, St. Louis, Mo.) and sonicated for 15 seconds with a Vibra-Cell Sonicator at 70% amplitude. The suspension was mixed with 25 mL HEPES-DMEM, centrifuged for 50 rcf for 5 minutes, and the supernatant removed. This was spun at 1000 rcf, and the pellet was resuspended to 10 mg/mL, based on initial mass. Cells were incubated in nanoparticle suspension for 40 minutes with gentle agitation. Excess nanoparticles were removed using centrifugation, and the coated cells were suspended in complete DMEM buffered with 50 mM HEPES to pH 7.7. This was combined with polymer precursor solutions for injection. In direct injection experiments, cells at the same concentration as in the pre-coated experiment were directly mixed with calcium carbonate nanoparticles before combining with alginate. The continuous phase was prepared by mixing 1% fluorosurfactant (Holtze 2008) and sterile-filtered 0.31% acetic acid (EMD Chemicals, Gibbstown, N.J.) in a fluorinated oil (3M™ Novec™ Engineering Fluid HFE-7500). The continuous and aqueous phases were injected into the microfluidic device at flow rates of 3.2 uL/min and 1 uL/min, respectively. Emulsions were broken after a 40 minute incubation by the addition of 20% 1H,1H,2H,2H-perfluorooctanol (Alfa Aesar).

To fabricate hybrid collagen-alginate hydrogel capsules, a cell and polymer precursor suspension containing 3 mg/mL calcium carbonate nanoparticles, 0.93% 139 kDa alginate, and 0.66 mg/mL rat tail collagen I (Corning, Bedford, Mass.) was injected at 4° C. into a microfluidic device of the same design as that used for alginate hydrogel capsules and operated with the same parameters. The resulting emulsion was incubated at 37° C. for 30 minutes. To fabricate hybrid fibrin-alginate hydrogel capsules, two solutions were prepared: one combining fibrinogen (20.3 mg/mL) and aprotinin (45 ug/mL); and one combining calcium carbonate nanoparticles (6.7 mg/mL), 2.1% alginate, and thrombin (22 U/mL). Cells were suspended in the solution containing fibrinogen. The two aqueous phases and the continuous phase were injected into separate inlets of the microfluidic device at flow rate of 0.5 uL/min and 3.2 uL/min, respectively.

Analysis of Cell Egress and Hydrogel Capsule Size

Alginate hydrogel capsules encapsulating cells were themselves encapsulated in a bulk collagen hydrogel. Following manufacturer's instructions, rat tail collagen I (Santa Cruz Biotechnology, Santa Cruz, Calif.) was first mixed with Dulbecco's phosphate buffered saline and sodium hydroxide to achieve a neutral pH, and then mixed with a suspension containing cells encapsulated in alginate hydrogel capsules to obtain a final collagen concentration of 1.85 mg/mL. The suspension was added to wells in a 48-well plate and allowed to cross-link at 37° C. for 30 minutes. Collagen gels were fixed after 1 day of culture. Cells were stained with rhodamine- or fluorescein-conjugated phalloidin (Biotium, Hayward, Calif.) and DAPI, and imaged with a Nikon E800 upright microscope. Only hydrogel capsules that showed a morphology of having contained cells (e.g., hollowed out) were considered to have led to cell-egress.

Mechanical Testing

Prior to atomic force microscopy measurement, encapsulated cells in fluorescently labeled alginate were adhered to a polylysine-coated glass slide. Glass microscope slides (VWR International, Radnor, Pa.) were cleaned in a solution of 10% sodium hydroxide and 60% ethanol, rinsed with deionized water, and incubated with poly-L-lysine (Handary SA, Belgium). MFP-3D system (Asylum Research) was used to perform AFM measurements of Young's modulus of hydrogels, using silicon nitride cantilevers (MLCT, Broker AFM Probes). The stiffness was calibrated by determining a spring constant of the cantilever from the thermal fluctuations at room temperature, ranging from 20~50 mN/m. The cantilever was moved towards the stage at a rate of 1 μm s$^{-1}$ for indentations. For bulk hydrogels, a disc of 5 mm×2 mm was placed onto a PDMS mold on a glass slide. Force-indentation curves were fit using the Hertzian model with a pyramid indenter. The elastic modulus of bulk alginate hydrogels was measured by casting 10-mm diameter and 2-mm thick cylindrical discs and compressing without confinement using an Instron 3342 mechanical apparatus at 1 mm min$^{-1}$.

Osteogenic Induction and Analysis of Alkaline Phosphatase (ALP) Production

To induce osteogenesis, D1s encapsulated in hydrogel capsules were cultured with complete DMEM supplemented with 10 mM β-glycerophosphate and 250 μM L-ascorbic acid, cycling every two days. D1s were fixed six days after osteogenic induction and stained with elf-97, following the manufacturer's instructions. Staining was stopped through washing with excess of PBS after 90 seconds. Fixed cells were further stained with rhodamine-conjugated phalloidin (Biotium, Hayward, Calif.). Fluorescence images for immunohistochemistry, elf-97 staining, and alginate were acquired using an Olympus IX81 inverted microscope equipped with a Cary II Nipkow-type Spinning Disc Confocal Attachment (BD Biosciences, San Jose, Calif.) and a Coolsnap HQ2 camera (Prior Scientific, Rockland, Mass.). The area-average fluorescence of cells stained with elf-97 and of alginate was quantified with ImageJ (FIG. 21).

Expression of Exogenous Genes in Cells

To introduce mCherry and Firefly Luciferase in MSCs, lentiviral particles containing the vector with mCherry-IRES-Firefly Luciferase driven by the CMV promoter were purchased from the Vector Core at Massachusetts General Hospital. Cells were incubated with viral particles for 2 days. Cells expressing mCherry were then sorted via flow-activated cell sorting (FACS). In some cases, Cyan Fluorescence Protein (CFP) and *Gaussia* Luciferase were introduced to MSCs using the same approach.

Animal Experiments

All animal experiments were performed in accordance with institutional guidelines approved by the ethical committee from Harvard University. To evaluate the biodistribution of donor cells in vivo, MSCs expressing firefly luciferase either with or without single cell encapsulation were injected into mice. Subsequently, 3 mg of D-luciferin was injected intraperitoneally into the 25 g mice followed by luminescence imaging with the IVIS Spectrum (PerkinElmer) at indicated times. The systemic secretions of donor cells were evaluated in two ways. For allogeneic transplantation, mMSCs from Balb/c mice expressing *Gaussia* luciferase were injected into C57/BL6 mice, followed by blood collection at regular time intervals. 10 uL blood was mixed with 100 uL of 20 ug/ml coelenterazine-h substrate in a white, opaque 96-well plate and luminescence was detected using a BioTek microplate reader. For xenograft, human MSCs were injected into NOD/SCID/IL-2γ-/- mice. For each sample, 50 μL of blood plasma was used to evaluate the systemic level of human IL-6 by using an ELISA kit (R&D Systems).

Figure 2B:
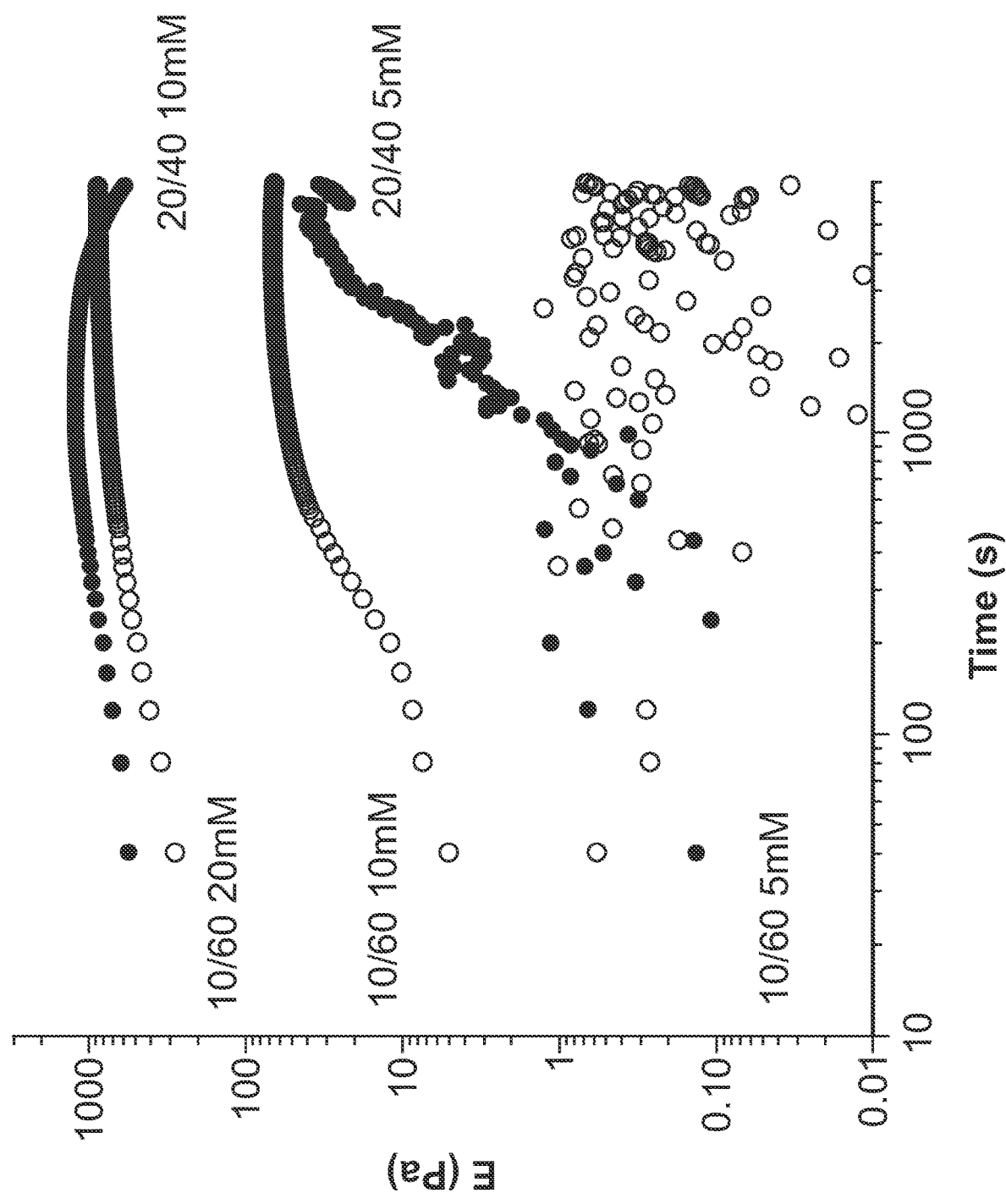
FIG. 2B is a graph showing gelation kinetics of 1% alginate with different $Ca^{2+}$ concentrations and molecular weights. The rheological measurements of alginate hydrogels during gel formation were performed at 37° C. with a frequency of 0.05 Hz and a stress of 1 Pa.

Example 1: Alginate Hydrogel Recapitulated a Range of Mechanical Properties of the Native Marrow To model a range of bone marrow (BM) mechanics in vitro, an alginate-based hydrogel conjugated with an integrin-binding RGD peptide was used. Alginate is non-adhesive to cells, so the adhesion to gels was mostly through the RGD. Mechanical properties of the hydrogel were controlled by $Ca^{2+}$ cross-linking and gel concentrations (FIG. 2A). Without gel cross-linking, 1% of the low molecular weight alginate ("1%", 150 kDa) fluid recapitulated the known viscosity value of BM (40-400 cP) (Gurkan and Akkus, 2008, Ann Biomed Eng 36, 1978-1991). The minimum $[Ca^{2+}]$ required for gelation of the 1% 1% alginate was 10 mM with E=50 Pa (FIG. 2B). In contrast, the same $[Ca^{2+}]$ led to E=1000 Pa with 1% of the higher molecular weight ("2%", 250 kDa) alginate or 2% of 1% alginate. Since increasing $[Ca^{2+}]$ beyond 10 mM may affect cell viability, a combination of RGD-modified and unmodified alginate gels were used to further increase stiffness by increasing gel concentration but maintaining the same RGD density.

Figure 3B:
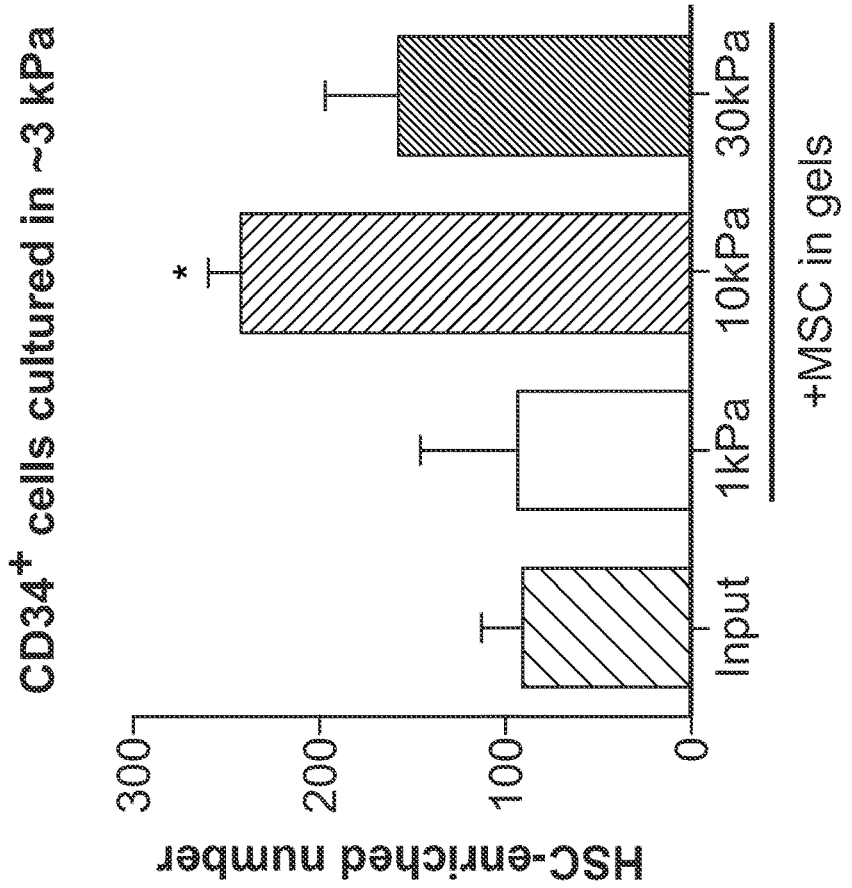
FIG. 3B is a bar graph showing that matrix stiffness regulates the release of soluble factors from MSCs that impact HSC/P differentiation in vitro. MSC:CD34+ ratio=5:1. *$P<0.05$ from one-way ANOVA with Tukey's HSD test. The absolute cell number was normalized by the total 10,000 cell input. $n\geq 3$.
Figure 3A:
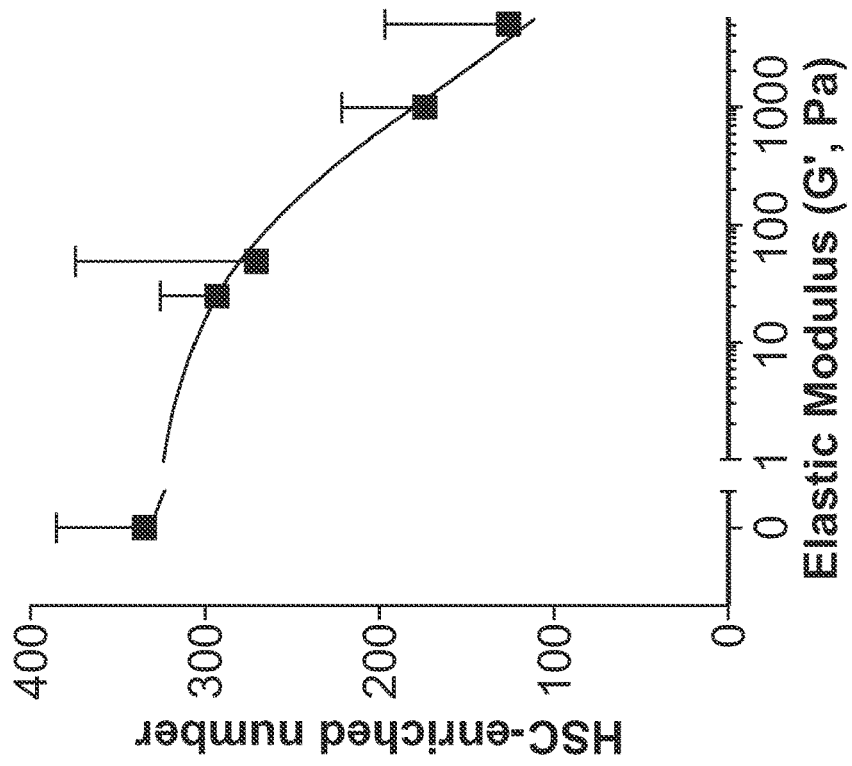
FIG. 3A is a graph showing the effect of matrix stiffness on CD34+ subpopulations in vitro. Matrix stiffness decreases the number of HSC-enriched subpopulations. Maximum=331, $IC_{50}$=1384 Pa, Hill coefficient=−0.5.

Example 2: Matrix Stiffness Regulated the Release of Paracrine Factors from MSCs that Control the Number of an HSC-Enriched Subpopulation In Vitro Matrix stiffness directly regulates HSC/P number in 2D culture with tropoelastin matrix (Hoist et al., 2010, Nat Biotechnol 28, 1123-1128). Here, matrix stiffness monotonically decreased the number of a human HSC-enriched subpopulation (defined as CD34+CD38−CD133+CD90+) (Majeti et al., 2007, Cell Stem Cell 1, 635-645) in the 3D alginate hydrogel with the half-maximal value=1.3 kPa (FIG. 3A). While the HSC-enriched population was highly sensitive to matrix stiffening, MSCs showed distinct biological responses, such as cell spreading and differentiation, across a large dynamic range of matrix stiffnesses (0.1-100 kPa) (Engler et al., 2006, Cell 126, 677-689; Huebsch et al., 2010, Nat Mater 9, 518-526). The ability of matrix stiffness to further regulate HSC/P differentiation by modulating paracrine secretion from MSCs was examined by using a transwell assay with 400 nm pore polycarbonate membrane to physically separate HSC/Ps and MSCs. Human BM CD34+ cells were encapsulated in the 3 kPa gel in the lower chamber, and MSCs were put in gels with a range of stiffness (1-30 kPa) in the upper chamber. Soluble factors from MSCs at 10 kPa further increased the HSC-enriched subpopulation number (FIG. 3B), indicating that an optimal stiffness exists for MSCs to release factors that maximize the HSC number.

Example 3: Encapsulation of Single Cells in Alginate Hydrogel with Distinct Matrix Stiffness A droplet microfludics-based method (Guo et al., 2012, Lab Chip 12, 2146-2155, incorporated herein by reference) was adapted to encapsulate a few cells or single cells in alginate-based gel droplets (FIG. 4A), which were then immobilized in a micro-well to characterize their mechanical properties by atomic force microscopy (AFM) (FIG. 4B). The analysis showed that it was possible to make alginate droplets with biologically relevant stiffness by changing initial calcium cross-linker concentrations (FIG. 4C) or alginate concentrations.

Figure 5:
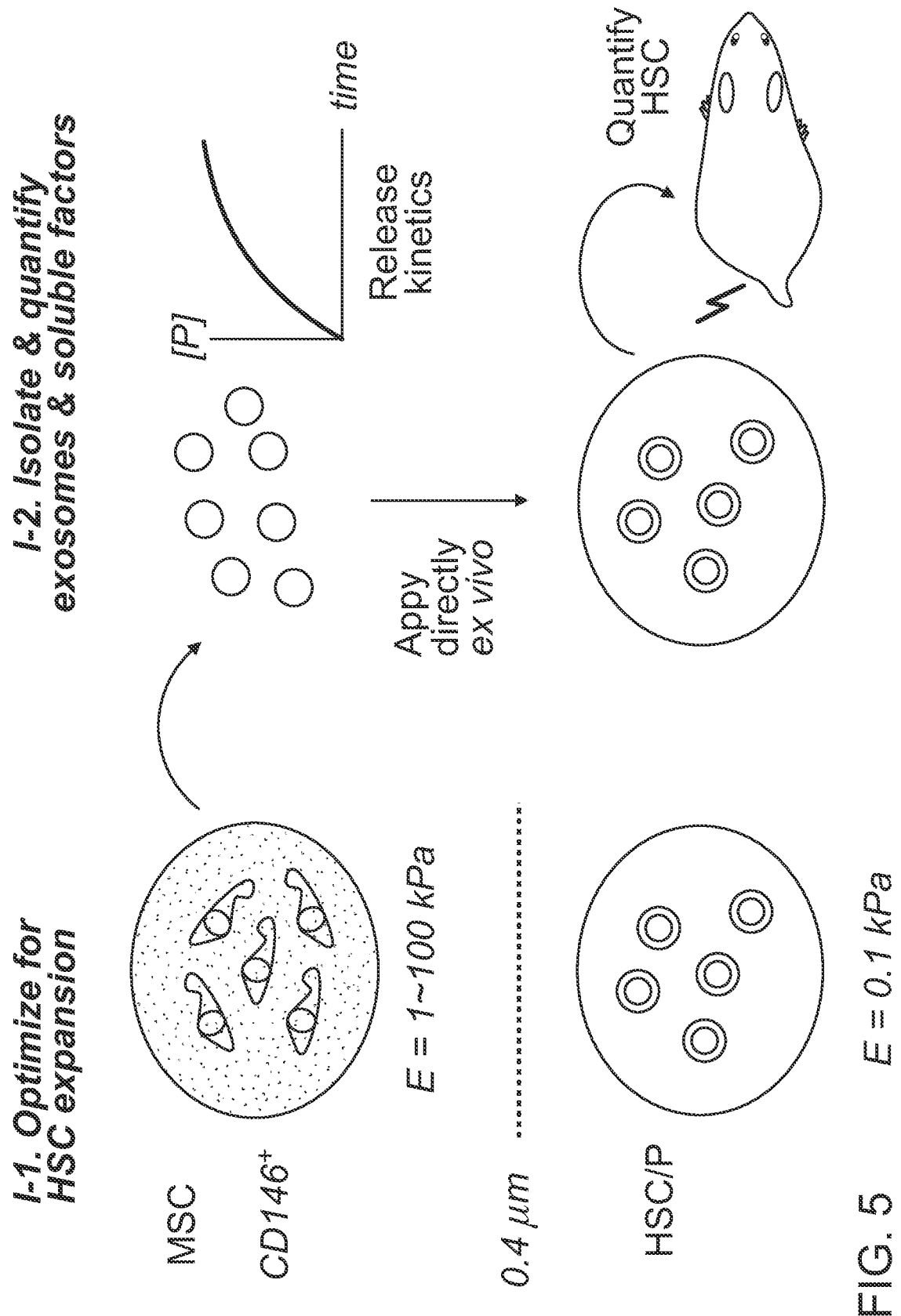
FIG. 5 is a schematic showing the methods used to characterize and quantify the hematopoietic factors released from MSCs in different matrix rigidities, as well as the methods used to delineate the mechanisms behind the stiffness-dependent factor release.

Example 4: Systematically Investigate and Validate Experimental Conditions where HSC-Enriched Population can be Maximized Experiments are conducted to elucidate mechanisms behind matrix stiffness-dependent release of hematopoietic factors from MSCs, e.g., to determine how matrix stiffness regulates paracrine release of hematopoietic factors from MSCs. (FIG. 5).

The results described above showed that HSC enrichment can be maximized by putting together CD34$^+$ cells in soft gels and MSCs in intermediate stiffness gels via a transwell setting (FIG. 3). Here, additional experimental conditions are tested for their ability to maximize HSC-enriched population. Homogenous populations of human MSCs (CD146$^+$) as defined previously (Sacchetti et al., 2007, Cell 131, 324-336) are tested. Also, different ratios between MSCs and HSCs are tested. For example, HSCs are encapsulated in soft (<100 Pa) gels to ensure the maximum HSC-enriched number. To validate the findings with human cells, mouse cells (D1 MSCs and Lin$^-$Sca-1$^+$cKit+CD48$^-$CD150$^+$ HSC/Ps) are tested. To test the generality of the relationship between matrix elasticity and paracrine regulation of hematopoiesis by MSCs, RGD-modified agarose or poly(ethylene glycol dimethacrylate) hydrogels of varying rigidity are used, as previously described (Huebsch et al., 2010, Nat Mater 9, 518-526).

Example 5: Determination of the Roles of Extracellular Vesicles Released from MSCs on HSC/P Differentiation Since BM MSCs are known to secrete exosomes and impact blood cancer cell proliferation (Roccaro et al., 2013, J Clin Invest 123, 1542-1555), the present study initially focuses on this mode of secretion to assess its impact on normal hematopoiesis. Since the alginate gels used in this study have a pore size of <100 nm and the transwell membrane filter has that of ~400 nm, it is likely that the paracrine effects described in FIG. 3B are due to either exosomes or soluble factors, but not microvesicles (~1 μm). The experiments described in this example focus on quantifying and characterizing potential hematopoietic factors released from MSCs cultured in different matrix rigidity. In some cases, to minimize the contribution from initial cell-cell contact on the MSC secretome, cells are cultured at low density (e.g., 1 million cells/mL or lower, e.g., $10^6$, $5\times10^5$, $1\times10^5$, $0.5\times10^5$ cells/mL or lower) by controlling cell number to gel volume ratios.

In some cases, if exosomes or soluble factors released from MSCs in standard alginate gels with pore size <100 nm (FIG. 2) do not play significant roles in hematopoiesis, macroporous cryogels with larger pore size (>10 μm) (Bencherif et al., 2012, Proc Natl Acad Sci USA 109, 19590-19595) will be tested to address if larger particles such as microvesicles from MSCs in different stiffness impact hematopoiesis.

Isolation and Quantification of MSC Exosome Release.

Exosomes are isolated from the conditioned media of MSCs cultured in alginate hydrogels with various stiffnesses, using size exclusion filters and ultracentrifugation as described previously (Roccaro et al., 2013, J Clin Invest 123, 1542-1555). The isolated exosomal content is then quantified by performing Western blotting with antibodies against exosome-specific markers (e.g. CD63 and CD81) and normalizing the signal by the total protein content for each sample. Alternatively, electron microscopy is used to count the number of exosomes labeled by their markers with a standard immunogold method. By counting the number of exosomes from MSCs at different culture time points, it is possible to calculate the general exosome release kinetics and model it as a function of matrix rigidity.

Effects of MSC Exosomes on HSC/Ps Ex Vivo.

An equal amount of exosomes isolated from MSCs at day 1, 3, and 7 cultures in different stiffnesses are directly applied to human BM CD34$^+$ cells encapsulated in the soft gel (~100 Pa). After a 7-day culture, flow cytometry is used to evaluate HSC/P subpopulations and hematopoietic lineages as described in FIG. 3. If significant expansion of HSC-enriched population is observed, HSC number will be functionally quantified by collecting cultured CD34$^+$-derived cells, serially diluting and xenotransplanting in sub-lethally irradiated (250 cGy) NOD/Shi-scid/IL-2Rγ$^{-/-}$ (NSG) mice. Human reconstitution in the recipient blood is analyzed at 4, 8, and 16 weeks after transplantation using an antibody against human-CD45 and CD47. Mice are then sacrificed to analyze BM engraftment. To functionally assess human hematopoietic progenitors, cells from culture are plated into semi-solid methylcellulose medium with growth factors to quantify colony-forming unit (CFU)—granulocyte-macrophage (GM), CFU-granulocyte, erythroid, macrophage, megakaryocyte (GEMM), and burst-forming unit (BFU-E). In some cases, instead of xenotransplantation to quantify human HSC number, studies are done with mouse BM D1 MSCs and HSC/Ps from donor mice (CD45.2), followed by competitive transplantation of donor cells into irradiated CD45.1 recipient mice.

Hematopoietic Factors Released from MSCs.

To address the possibility that the content of secreted hematopoietic proteins from MSCs is changed by matrix elasticity, isolated exosomes, or more broadly, conditioned media concentrated with the 3 kDa cut-off filter is subjected to separation by SDS-PAGE gel electrophoresis. The gel is stained with Coomassie blue and selected bands (<50 kDa) are excised. Sequencing grade-modified trypsin is used to digest proteins in the bands. Peptides are separated by liquid chromatography, followed by mass spectrometry through a LTQ-Orbitrap XL ("LC-MS/MS"). Raw mass spectrometry data is annotated by SEQUEST (≥3 peptides per protein). The label-free "Peptide Ration Fingerprint" algorithm is used to quantify peptides in different samples (Swift et al., 2013, Science 341, 1240104). In some cases, instead of LC-MS/MS to analyze proteomes, antibody-based protein array methods will be used (Parekkadan et al., 2007, PLoS One 2, e941).

Example 6: Mechanisms Behind Mechanical Regulation of Factor Release from MSCs To confirm the immediate involvement of actomyosin forces in mechano-sensitive factor release, MSCs cultured in hydrogels with different matrix stiffnesses for 1-2 days are treated with blebbistatin (myosin-II ATPase inhibitor) or Y-27632 (Rho-associated protein kinase inhibitor) for 1 day, and their exosome numbers are quantified. For indirect long-term regulation, mechanical stress triggered by stiff substrates activates mechano-sensitive transcription factors and alters gene expression to further augment cellular tension (Wang et al., 2009, Nat Rev Mol Cell Biol 10, 7582), which may then affect exocytosis. Therefore, whether or not the mechano-sensitive factor release from MSCs also requires transcription factors is tested (FIG. 5). Transcription factors are activated by matrix stiffness either indirectly by biochemical changes in cytoskeletal networks or directly by attachment to the force-generating cytoskeleton (Janmey et al., 2013, Differentiation 86, 112-120). Representative transcription factors from indirect and direct modes of activation are tested: Megakaryocyte acute leukemia protein (MAL)/Serum Response Factor (SRF) (Miralles et al., 2003, Cell 113, 329-342) and Yes-associated protein (YAP)/Transcriptional coactivator with PDZ-binding motif (TAZ) (Dupont et al., 2011, Nature 474, 179-183), respectively. Short hairpin RNA (shRNA) lentivirus is used to downregulate these transcription factors in MSCs, followed by testing their ability to regulate HSC/P differentiation using a transwell assay across different stiffnesses. Both exosome release kinetics and soluble factor contents are also evaluated after shRNA downregulation.

Figure 6:
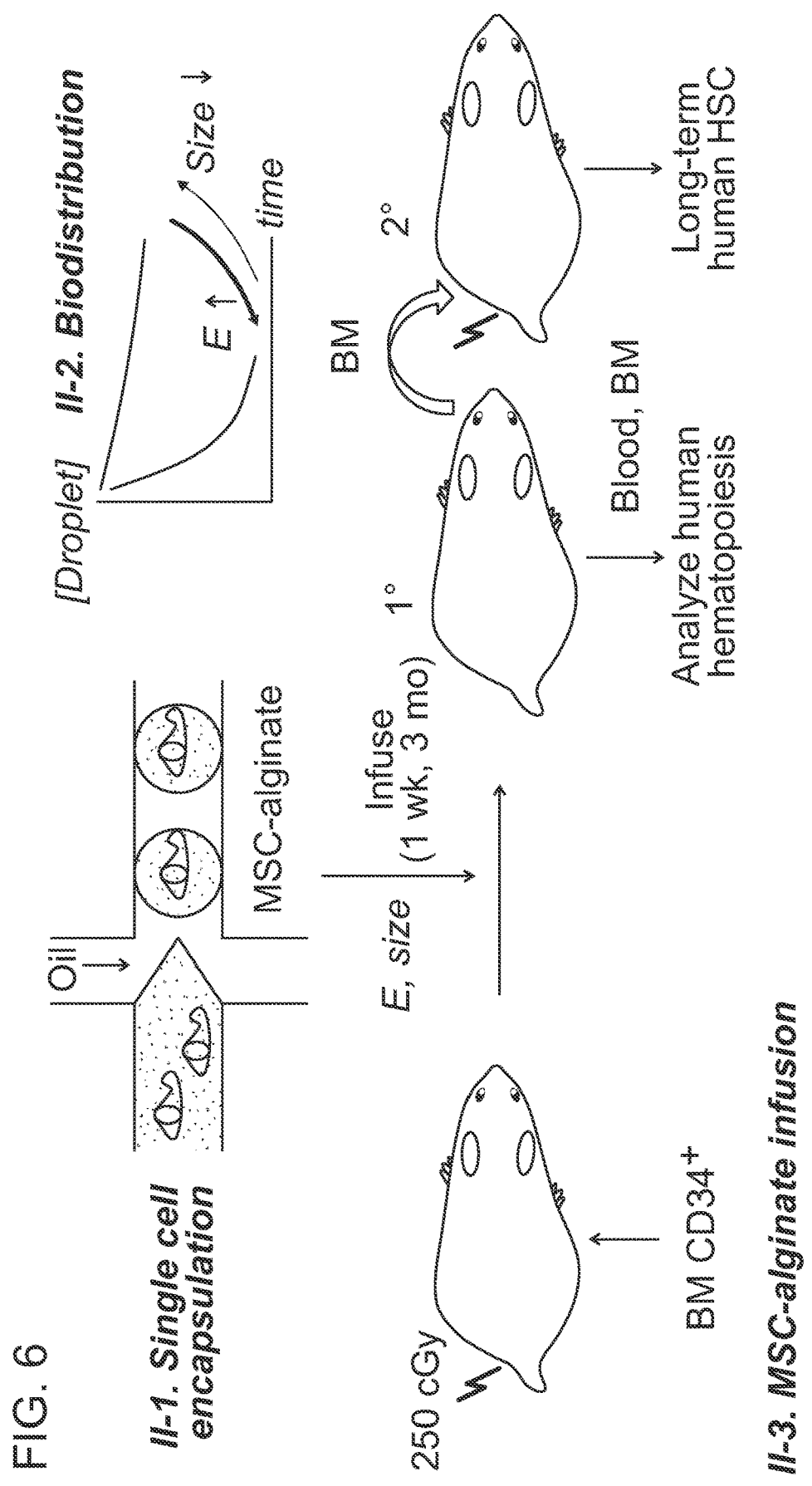
FIG. 6 is a schematic showing the encapsulation of single cells, e.g., MSCs, in alginate droplets with substrates of different stiffness, followed by infusion into a subject to program hematopoiesis in vivo.

Example 7: Infusible Hydrogel Micro-Carriers that can Mechanically Trigger Hematopoietic Factor Release from Encapsulated MSCs In Vivo Bulk hydrogels have been used for subcutaneous implantation of cells, but they are not currently suitable for other routes of in vivo administration, including intravenous or intrabone. MSCs in hydrogels have been implanted subcutaneously to study their indirect impact on hematopoiesis by forming a bone nodule, which will then recruit marrow cells. To study the direct impact of MSCs on BM-resident HSC/Ps in vivo via hematopoietic factor release triggered by substrate stiffness, a microfluidic method is optimized to encapsulate individual MSCs in alginate gels, followed by infusion for sustained delivery of secreted factors in vivo (FIG. 6).

A microfluidic system to encapsulate single cells in spherical alginate picoliter droplets was developed (FIG. 4). This technique is adapted and used to vary matrix stiffness and size of the droplets, place them in microwells, and confirm their mechanical properties by AFM. In this way, single cell encapsulation into hydrogels with controlled matrix stiffness and size is achieved.

Single Cell Encapsulation:

Cells, e.g., MSCs, are incubated with $CaCO_3$. After washing out excess $CaCO_3$, the aqueous phase (containing liquid RGD-conjugated alginate and cells) is injected into a microfluidic system. A continuous flow of oil with acetic acid is applied to pinch off the aqueous phase into beads and dissolve $CaCO_3$ into $Ca^{2+}$ ions, which cross-link alginate beads that encapsulate cells. To control substrate rigidity, different concentrations of alginate or $CaCO_3$ are used. To control alginate bead diameters, a microfluidic channel with different widths is used.

Microwell Fabrication:

Soft lithography is used to fabricate microwells in poly (dimethyl siloxane) (PDMS) (Qin et al., 2010, Nat Protoc 5, 491-502). A photomask is designed using computer-aided design software and printed. The master is fabricated by shining ultraviolet light on a silicon wafer with photoresist through the photomask. PDMS is then polymerized using the master as a mold to create microwells. Encapsulated cells are then seeded in each well.

Mechanical Testing of Droplets by AFM:

Single droplets in PDMS microwells are probed with AFM. Young's modulus of each droplet is calculated from linear indentation measurements with pyramidal tip attached to a cantilever (Engler et al., 2007, Methods Cell Biol 83, 521-545).

In Vivo Biodistribution of Hydrogel Droplets with Different Substrate Rigidity and Size.

The biodistribution of micro-scale hydrogel particles is dictated both by their sizes and elastic moduli, which likely affect circulation times upon intravenous injection. In past studies, gel particles with lower elastic moduli had higher circulation times (Merkel et al., 2011, Proc Natl Acad Sci USA 108, 586591), but increasing particle diameters decreased the circulation times (Kohane, 2007, Biotechnol Bioeng 96, 203-209). To control for the biodistribution kinetics while altering substrate rigidity, alginate droplets are systematically characterized in terms of elastic moduli (1-100 kPa) and diameters (10-50 µm) for their biodistribution kinetics in vivo. To facilitate in vivo non-invasive imaging in living mice by the Xenogen IVIS Imaging System (PerkinElmer), RGD-modified alginate is conjugated with amine-cy5.5 (Lumiprobe) (excitation: 678 nm, emission: 701 nm) to minimize background fluorescence from tissues. The equal weight of alginate droplets is injected per mouse via either an intravenous or intrabone route. For the intravenous route, 200 µl of 0.4 mg polymer/20 g mouse is injected retro-orbitally (e.g. 10 million 20 µm diameter 1% alginate droplets). After injection, the IVIS is used to study particle distribution across different organs. In addition, peripheral blood is sampled and the presence of gel droplets in circulation is detected by flow cytometry. Mice are analyzed every 30 min for the first hour, followed by every two days for at least one week. Droplets from blood samples are also sorted after 1-3 days of infusion, and their integrities and mechanical properties are confirmed by AFM. Post-mortem histological analyses are performed on tissues, including lung, spleen, and marrow, to further characterize the tissue localization of injected gel droplets.

Impact of MSCs Encapsulated in Hydrogel Droplets with Different Substrate Stiffness on In Vivo Hematopoiesis.

After establishing appropriate size parameters to vary substrate stiffness of hydrogel droplets without substantially altering their in vivo biodistribution kinetics, human MSCs are encapsulated in the droplets. Prior to infusion of MSC-droplets, human BM $CD34^+$ cells are intravenously transplanted into sub-lethally irradiated NSG mice. MSC-droplets with varied stiffness are then infused within 1 week or after 3 months of $CD34^+$ transplantation to assess their effects on early HSC/P engraftment and steady-state hematopoiesis, respectively. This will follow the analysis of human blood reconstitution using flow cytometry. If blood reconstitution is substantially enhanced by MSC-droplets, the mice will be sacrificed to analyze the human HSC/Ps in BM by flow cytometry. To functionally confirm whether enhanced human hematopoiesis is due to HSC expansion, BM is serially transplanted to new recipients followed by tracking human reconstitution up to 4 months. The efficacy of the MSC-droplets on hematopoiesis is compared with the direct injection of soluble factors, extracellular vesicles from MSCs, or non-encapsulated MSCs.

MSC homing after intravenous injection is a rare event (Ranganath et al., 2012, Cell Stem Cell 10, 244-258), and in some examples, the hydrogel further prevents homing. The presence of non-hematopoietic human cells in recipient tissues is evaluated by histological analysis to confirm whether any effect on hematopoiesis by MSCs is due to their secreted factors. If intravenous infusion does not lead to any satisfactory effect, intrabone infusion of MSC-droplets will be performed and their effects on hematopoiesis analyzed within a week to avoid effects from MSCs integrating into BM. Although purifying alginate increases biocompatibility, it is possible that alginate droplets are physically trapped into spleen or lungs. While such an entrapment will still allow factors to be secreted from MSCs (Lee et al., 2009, Cell Stem Cell 5, 54-63), entrapment may increase the probability for MSC-droplets to be engulfed by macrophages. If significant clearance by macrophages occurs, alginate will be conjugated with a minimal 'self' peptide derived from CD47 that impedes phagocytosis (Rodriguez et al., 2013, Science 339, 971-975). If ionic cross-linking of alginate hydrogels is too weak for in vivo circulation, a bioorthogonal 'click' chemistry method will be used to covalently cross-link alginate. If size is not sufficient to normalize the biodistribution kinetics caused by changes in substrate stiffness, other parameters will be varied, such as surface charge, e.g., by coating with poly-L-lysine.

Example 8: Encapsulation of Cells

Figure 16A:
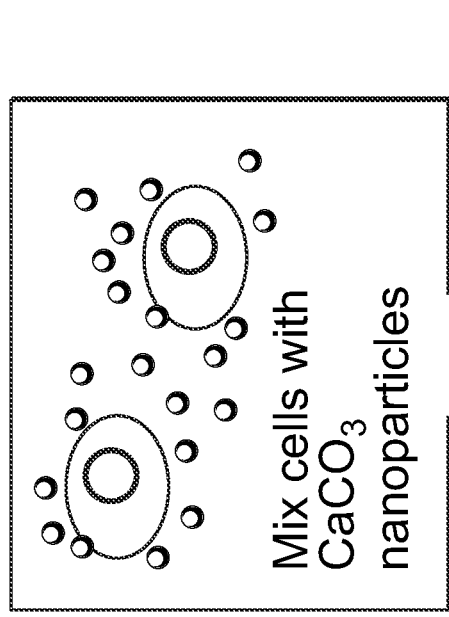
FIG. 16A is a part of a schematic of a cell encapsulation procedure, showing cells coated with calcium carbonate nanoparticles.
Figure 16B:
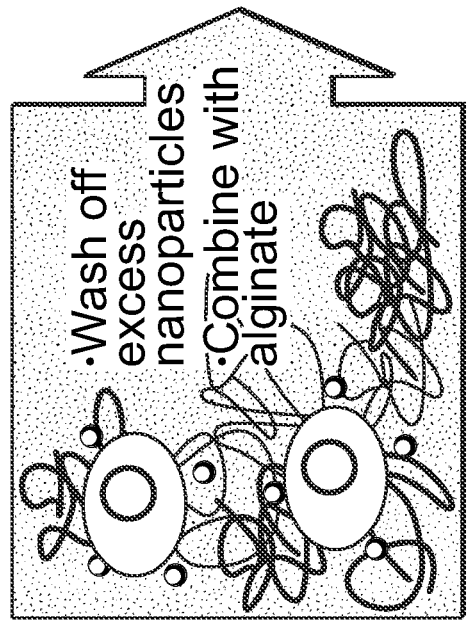
FIG. 16B is a part of a schematic of a cell encapsulation procedure, showing that excess nanoparticles are removed, and nanoparticle-coated cells are mixed with alginate.
Figures 16C, 16D:
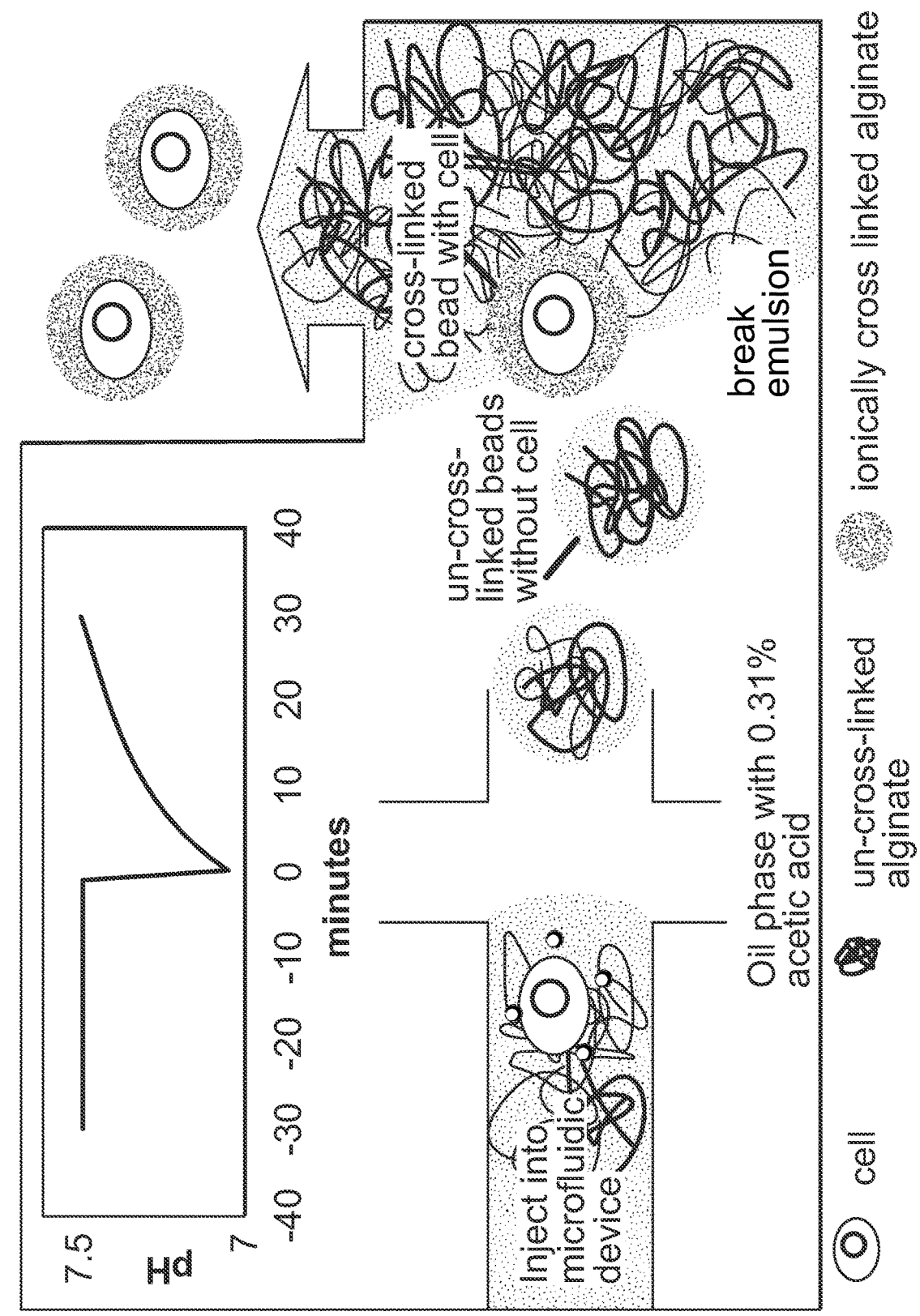
FIG. 16C is a part of a schematic of a cell encapsulation procedure, showing that the suspension and a fluorinated oil-surfactant-acetic acid solution are injected into a microfluidic device. An aqueous-in-oil emulsion is formed at the T-junction in the device. Acetic acid diffuses into the aqueous phase. Only cell- and nanoparticle-containing droplets cross-link.
FIG. 16D is a part of a schematic of a cell encapsulation procedure, showing that the emulsion is mixed with cell medium and broken by addition of perfluoro-octanol.
Figure 21B:
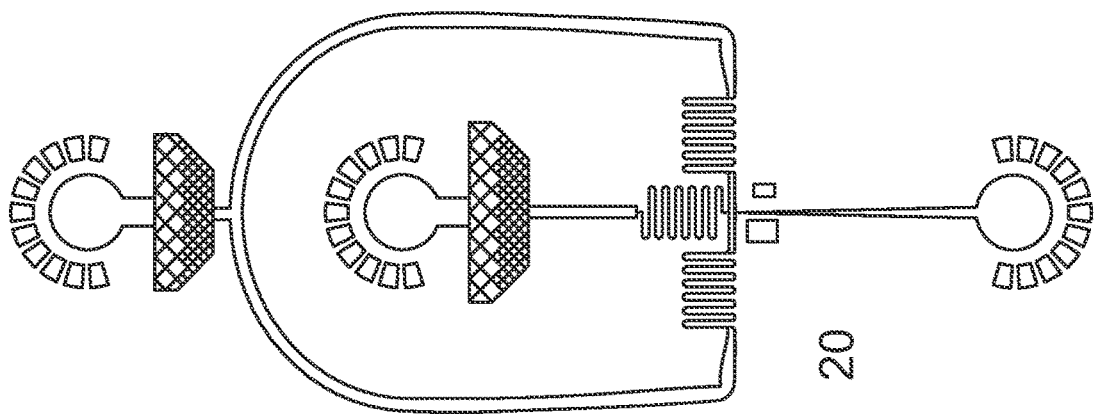
FIG. 21B is a schematic of a microfluidic device used for encapsulations.
Figure 21A:
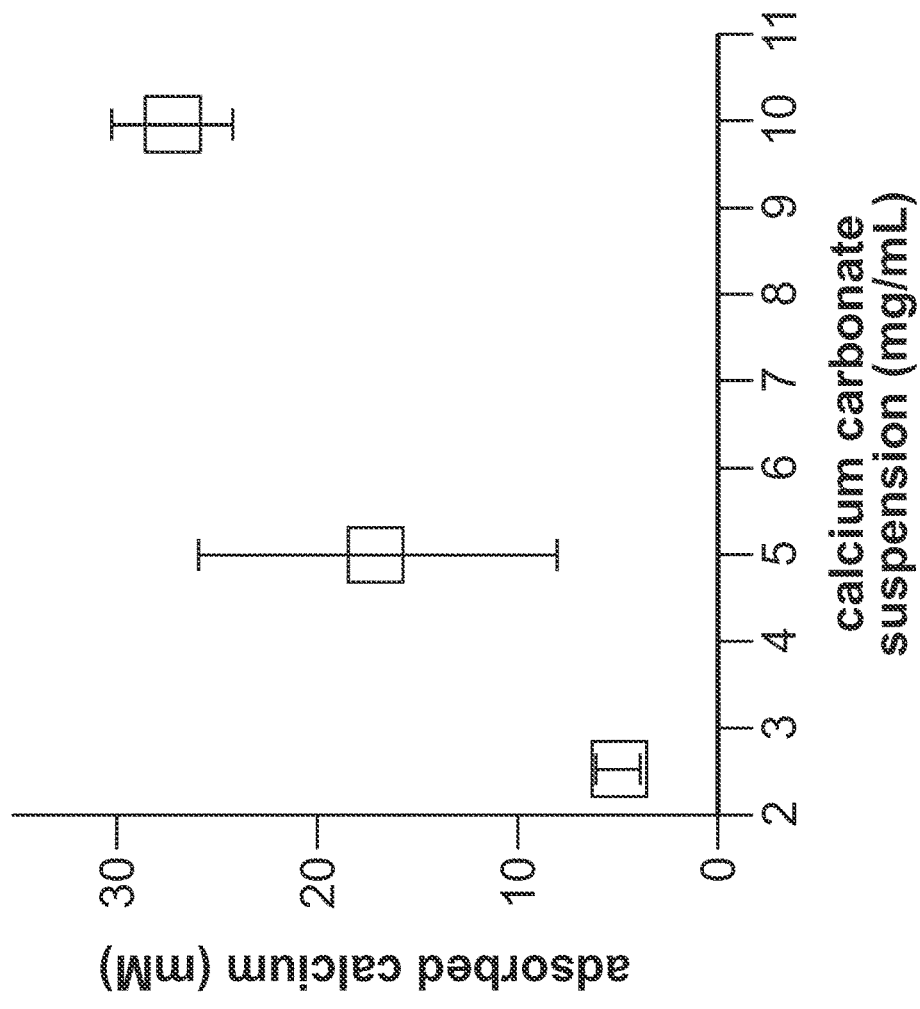
FIG. 21A is a graph showing calcium adsorption to cells as a function of concentration of calcium carbonate nanoparticles in suspension incubated with cells.
Figure 21C:
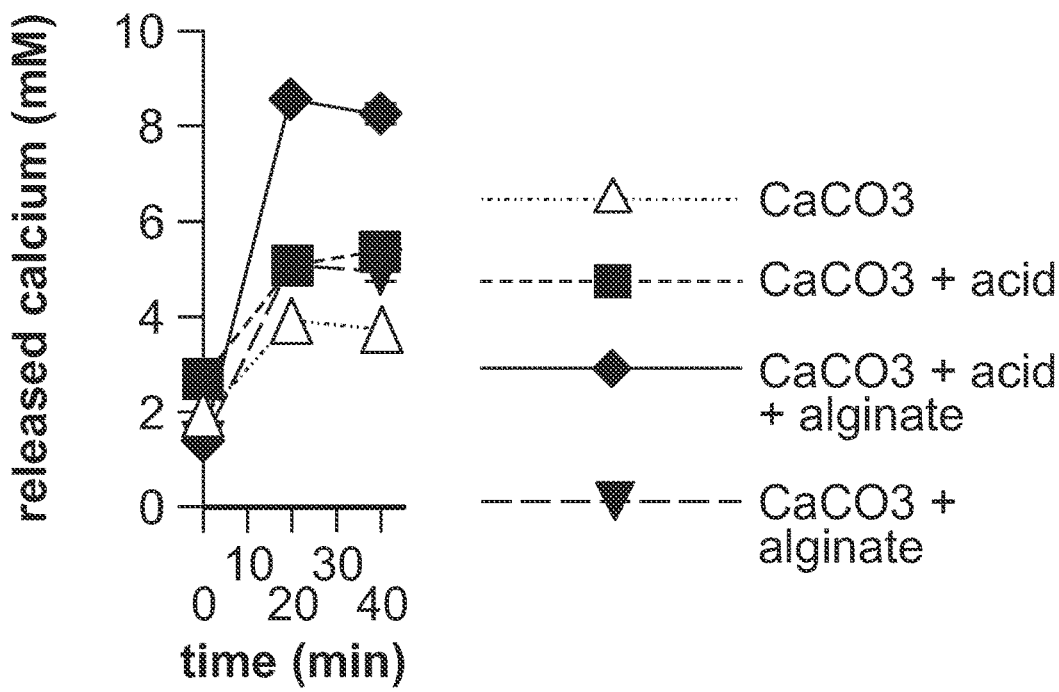
FIG. 21C is a graph showing the concentration of calcium released from calcium carbonates nanoparticles in a 3.0 mg/mL suspension upon exposure to cell medium, acetic acid, alginate, and a combination of acetic acid and alginate.

D1 cells were first incubated with calcium carbonate nanoparticles, which adsorbed to the cell surface (FIG. 16A) as a function of nanoparticle concentration (FIG. 21A). After non-adsorbed nanoparticles were washed away, coated cells were mixed with liquid sodium alginate (FIG. 16B) and injected into a microfluidic device (FIGS. 16C and 21B). Droplets of alginate, both with and without cells, were pinched off by a continuous phase composed of hydrofluoroether 7500, 1% fluorosurfactant, and 0.31% acetic acid. Diffusion of the acid into the alginate droplet caused a pH drop from 7.5 to 6.1 that, in the presence of nanoparticles, was transient and mediated the dissolution of calcium from the nanoparticles (FIG. 21C). Only cell- and nanoparticle-containing droplets cross-linked. After a 30 minute incubation, the emulsion was broken to retrieve the encapsulated cells (FIG. 16C).

Figure 17D:
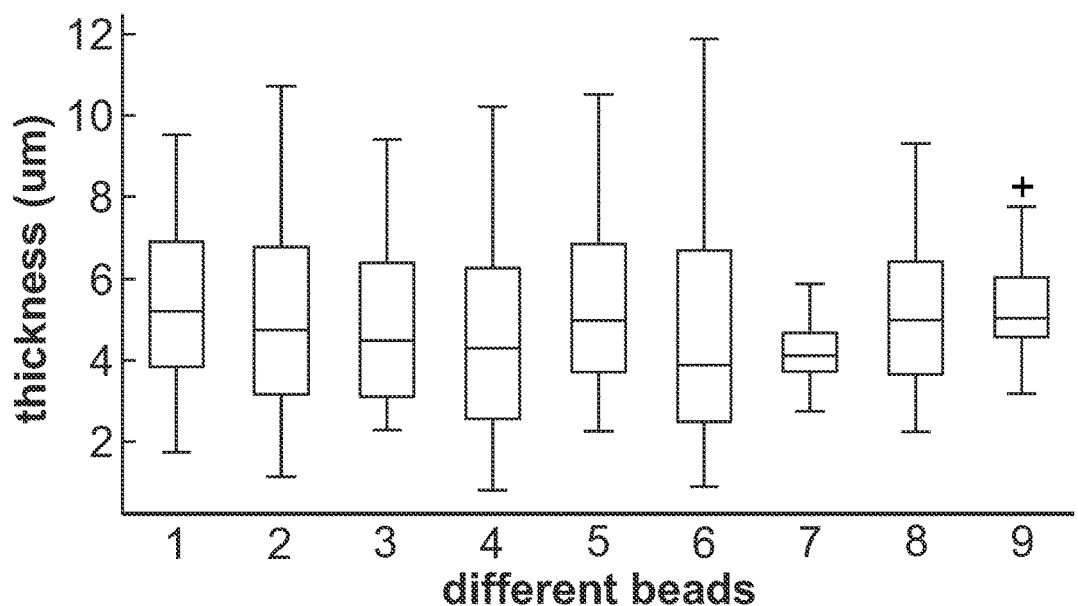
FIG. 17D is a graph showing the thickness of hydrogel layer, measured at multiple locations around cells, for 9 encapsulated D1 cells.
Figure 17E:
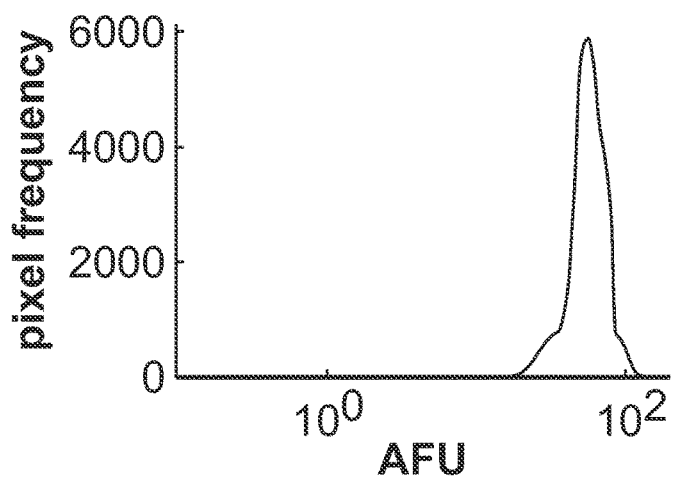
FIG. 17E is a histogram of alginate intensity per pixel taken from confocal images of 16 different cell-encapsulating alginate capsules, fabricated using the pre-coating method. The single peak indicates homogeneity within the capsules.
Figure 17F:
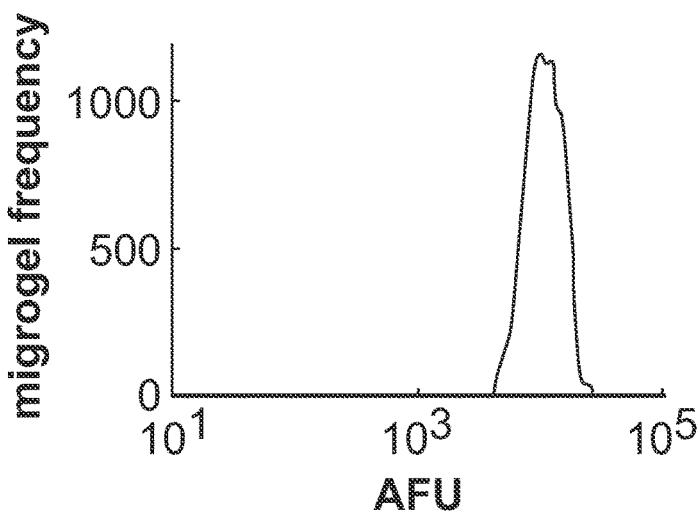
FIG. 17F is a histogram of alginate intensity from 40,475 events, consisting of the encapsulation output after pre-coating cells with nanoparticles.
Figure 21D:
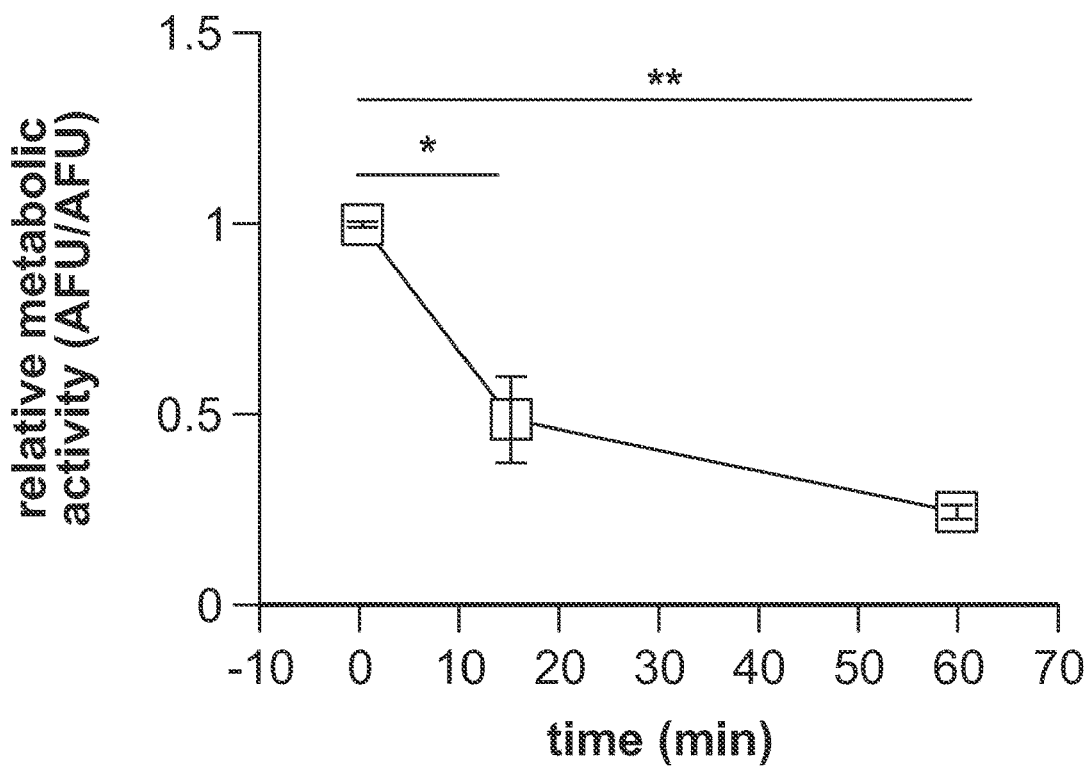
FIG. 21D is a graph showing cell viability as a function of duration of exposure to hydrofluoroether 7500 with 1% fluorosurfactant, as assessed by Alamar Blue and normalized to the highest AFU value.

Direct injection of a suspension containing cells, alginate, and nanoparticles (not pre-adsorbed to cells) produced both empty and cell-containing hydrogel capsules (FIG. 17A). When cells were pre-coated with nanoparticles, encapsulation yield was qualitatively higher (FIG. 17B). The alginate hydrogel formed a thin layer around the encapsulated cells, ranging from 0.80 to 12 µm and averaging 4.8 um thick (FIG. 17C-D). Moreover, both the alginate within the hydrogel capsule (FIG. 17E), as assessed by image analysis of confocal slices, and the population of hydrogel capsules (FIG. 17F), as assessed by flow cytometry, followed a unimodal distribution. Using a combination of flow cytometry and image analysis, the coefficient of variation (CV) of the fluorescent intensity of hydrogel capsules was 31%, and the CV of hydrogel capsule size was 6.5%. In comparison, the polymer content of empty hydrogel capsules had a CV of 14% and the hydrogel capsule diameter had a CV of 3.4%. Because prolonged exposure to the oil and surfactant phase decreased cell viability, acetic acid was mixed into the oil and surfactant phase prior to injection to immediately crosslink the alginate hydrogel capsule (FIG. 21D).

Figure 21E:
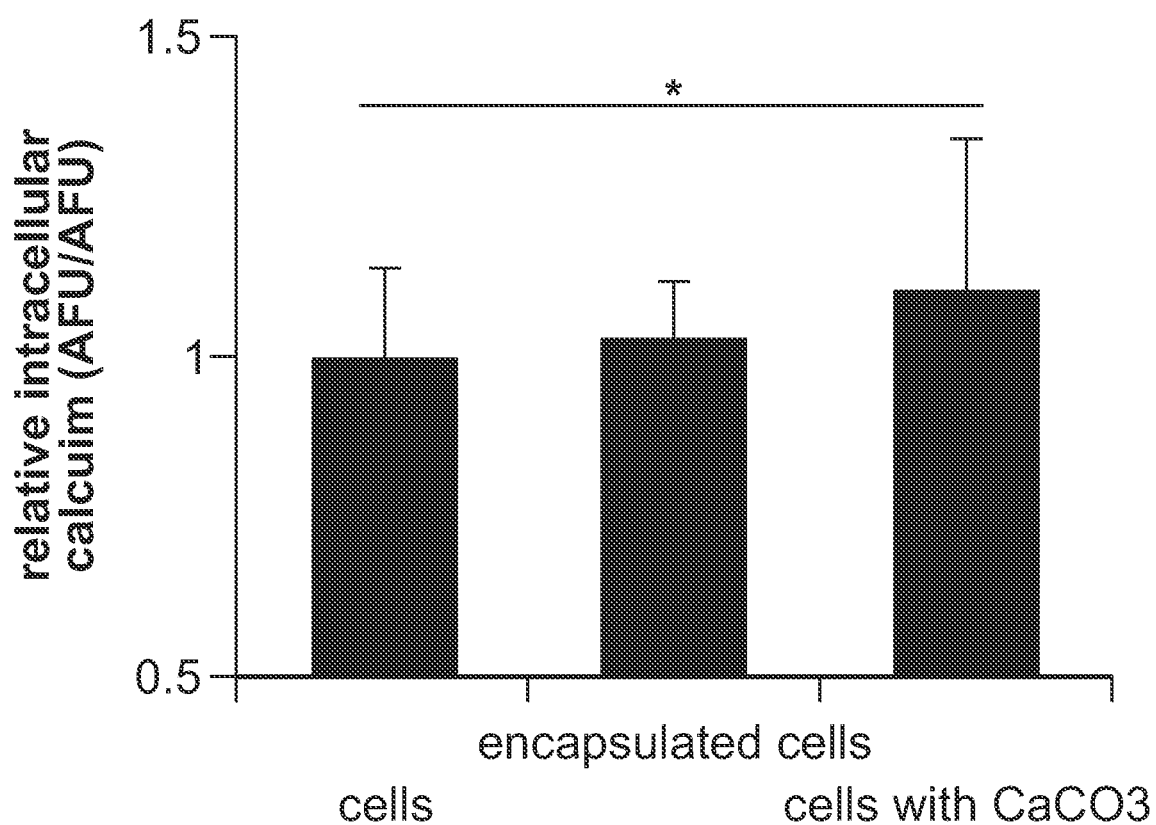
FIG. 21E is a graph showing relative intracellular calcium levels in non-encapsulated cells (cells), encapsulated cells, and cells directly exposed to $CaCO_3$ nanoparticles (cells with $CaCO_3$). For this assay, cells were incubated in their respective conditions for 24 hours. *=p<0.05, **=p<0.01.
Figure 21F:
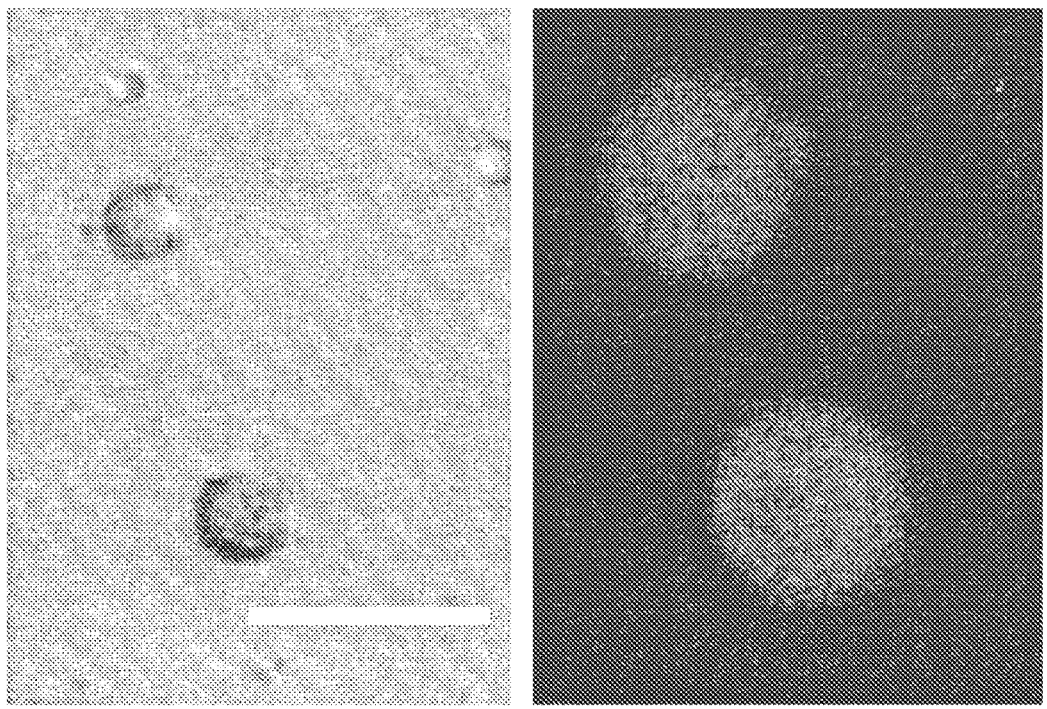
FIG. 21F are representative brightfield and fluorescent images of OECs encapsulated in rhodamine-labeled alginate.
Figure 21G:
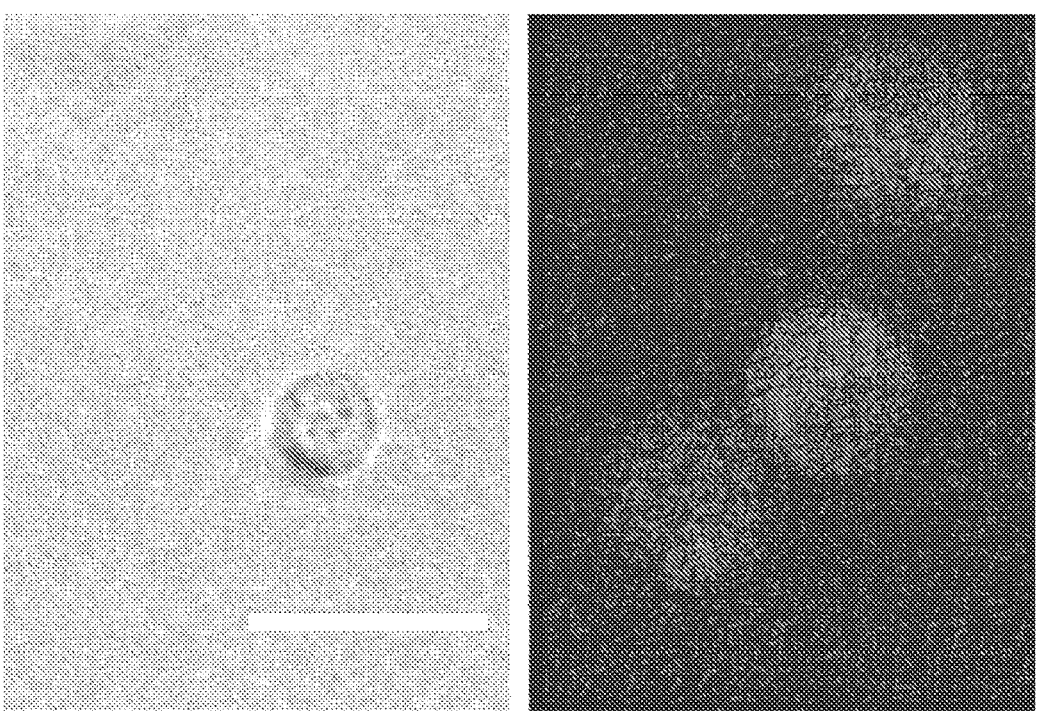
FIG. 21G are representative brightfield and fluorescent images of OP9 cells encapsulated in rhodamine-labeled alginate. Scale bar=50 um.

During the encapsulation process, not all of the nanoparticles dissolved. A comparison between the amount of calcium carbonate nanoparticles adsorbed to cell surfaces and the amount dissolved from alginate and acetic acid (FIGS. 21A, C) showed that the entire mass of nanoparticles did not dissolve during the encapsulation process. To assess the impact of the remaining nanoparticles on cells, the intracellular calcium levels of encapsulated cells, non-encapsulated cells, and cells directly exposed to nanoparticles was compared. No significant differences in intracellular calcium levels were found between encapsulated and non-encapsulated cells, though cells directly exposed to nanoparticles exhibited higher intracellular calcium levels than cells alone (FIG. 21E). The non-dissolved nanoparticles had no impact on intracellular calcium levels in encapsulated cells (FIG. 21D).

Figure 17G:
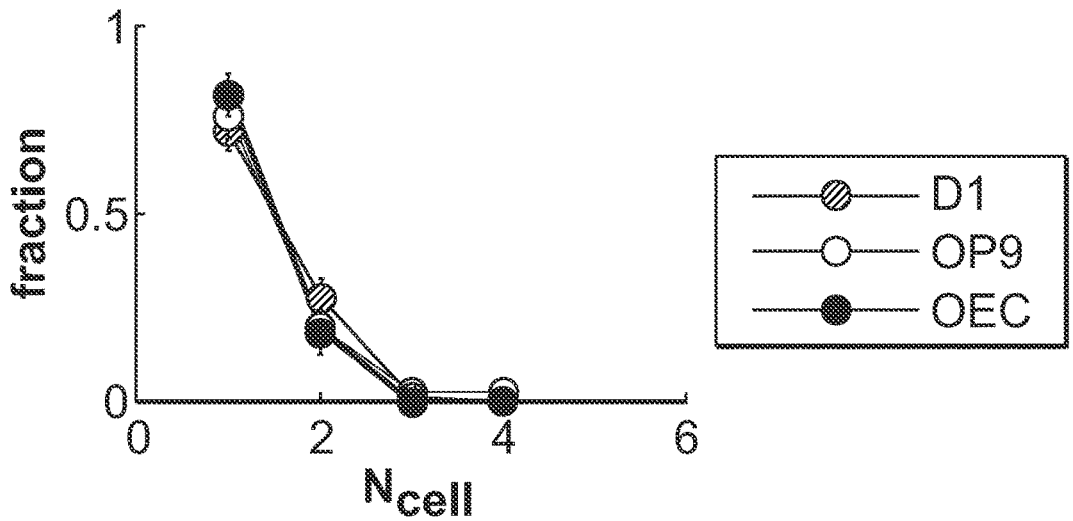
FIG. 17G is a histogram of initial number of cell(s) per alginate microgel for three different cell types encapsulated after pre-coating with nanoparticles.
Figure 17H:
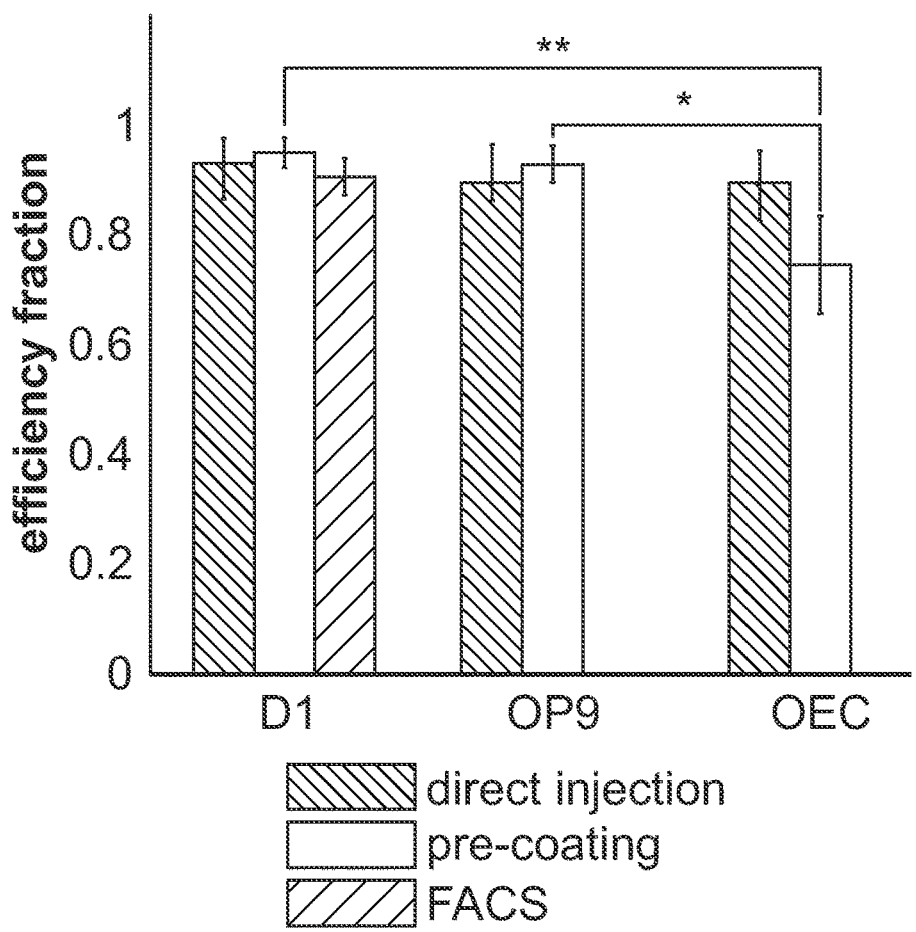
FIG. 17H is a graph showing the fraction of D1 cells, OP9 cells, and OECs encapsulated in microgels (efficiency) by direct encapsulation, direct encapsulation followed by FACS to generate a pure population, and pre-coating with $CaCO_3$ nanoparticles before encapsulation.
Figure 17I:
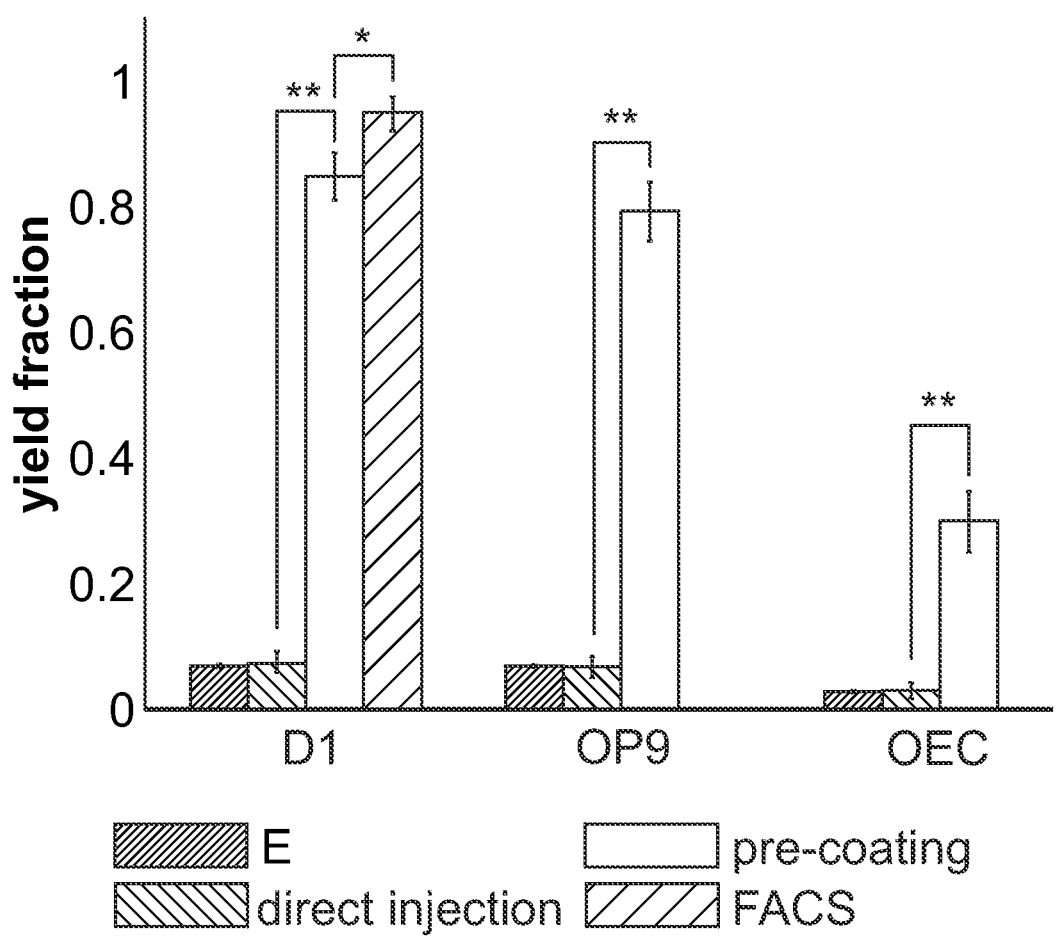
FIG. 17I is a graph showing the fraction of alginate beads containing encapsulated D1 and OP9 cells and OECs (yield) by direct encapsulation, direct encapsulation followed by FACS, and pre-coating with $CaCO_3$ nanoparticles.
Figure 17J:
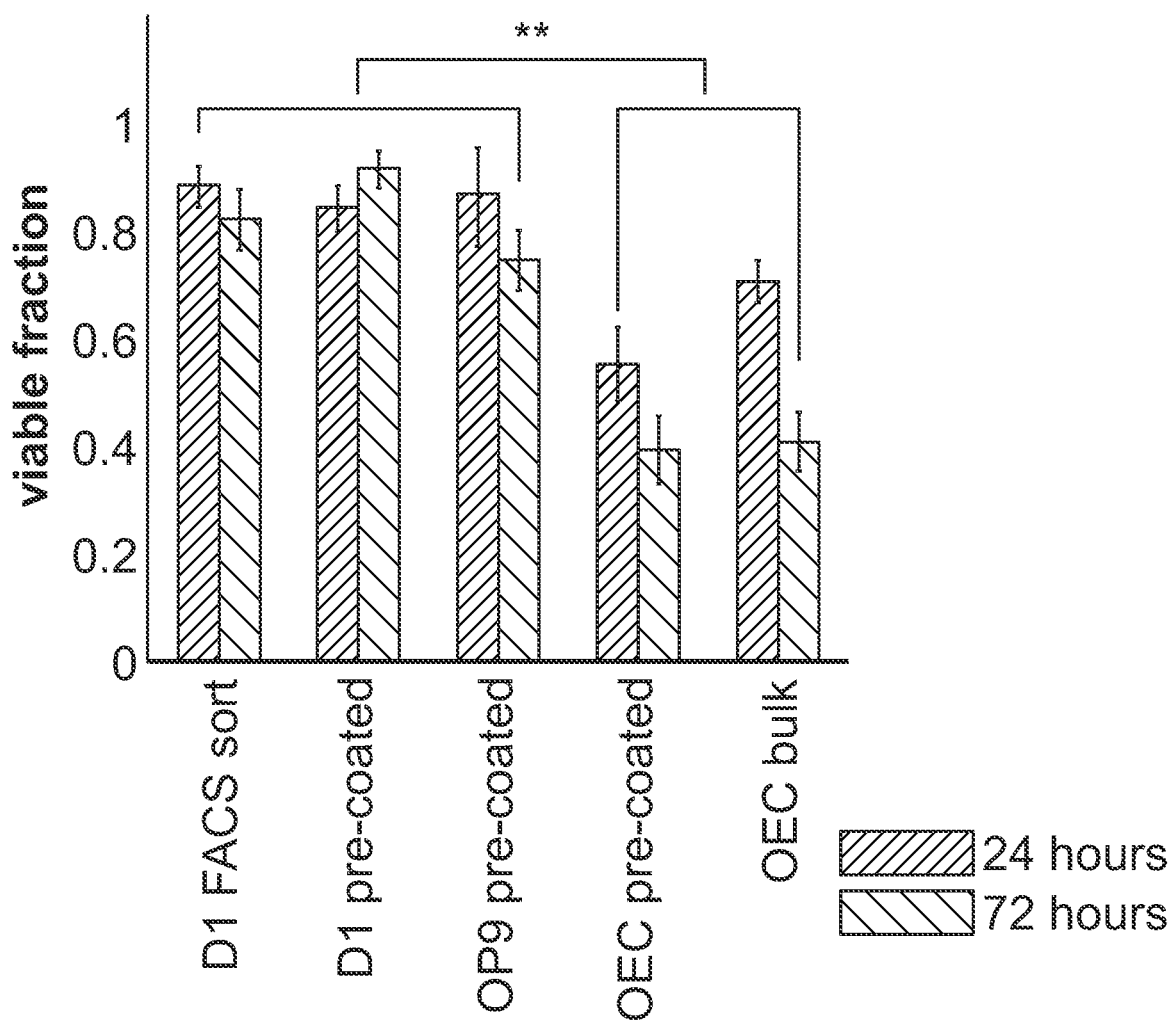
FIG. 17J is a graph showing viability of encapsulated cells 1 day and 3 days after encapsulation using precoating with nanoparticles (for D1s, OP9s, and OECs), with direct injection without pre-coating followed by a FACS sort (for D1s), and in bulk hydrogels (for OECs).

OP9 cells, OEC cells, and D1 murine MSCs cells were encapsulated (FIGS. 21-F-G). The number of cells per hydrogel capsule for the three cell types was consistent, with 71%-81% of the hydrogel capsules containing only one cell (FIG. 17G). Encapsulation efficiency with pre-coated cells ranged from 74% for OEC cells to 95% for OP9 cells and D1 murine MSCs (FIG. 17H). For all cell types, the encapsulated yield of pre-coated cells was an order of magnitude higher than of cells directly encapsulated without pre-coating with nanoparticles (FIG. 17I). The expected yields for direct injection into a microfluidic device (without pre-coating cells with nanoparticles) were calculated from hydrogel capsule size and starting cell density, with the assumption that all alginate droplets would cross-link and that only one cell would be contained in each cell-containing droplet. These expected values were similar to experimental results for direct injection into the microfluidic device (without pre-coating cells with nanoparticles) (FIG. 17I). Yields for pre-coated D1s and OP9 were comparable to the yield following flow cytometry sorting of D1 cells encapsulated directly without nanoparticle pre-coating (FIG. 17I). The encapsulation yield of OECs was poorer than that of D1 and OP9 cells, but still an order of magnitude higher with pre-coating of nanoparticles than with direct encapsulation (FIG. 17I).

To assess the ability of small hydrogel capsules to support cell viability in culture, encapsulated cells were stained with calcein and ethidium homodimer one day and three days after encapsulation (FIG. 17G). D1 and OP9 cells exhibited high viability both one and three days after encapsulation. The viability of OECs 1 hour after encapsulation was high (0.77+/−0.22); at later time points, their viability was lower. The encapsulation process was unlikely to be responsible for this lower viability observed at later time points. To further assess the ability of alginate gels to support OECs, OECs were encapsulated in 8-mm×1-mm alginate bulk hydrogels with calcium sulfate crosslinking and cultured; this is a standard method for encapsulation of cells in alginate gels. There were no significant differences in viability between OECs in hydrogel capsules and bulk hydrogels, showing that it was likely not the encapsulation step that led to the lower long-term viability of OECs in the alginate gels.

Example 9: Alteration of Alginate Molecular Weight and Mechanics

The egress of encapsulated cells as a function of polymer molecular weight was analyzed. In the experiments described in Example 8, D1s were encapsulated using polymer with a weight average molecular weight of 139 kDa. In this example, higher (232 kDa) and lower (54 kDa) molecular weight alginates were also used for cell encapsulation.

Figure 18A:
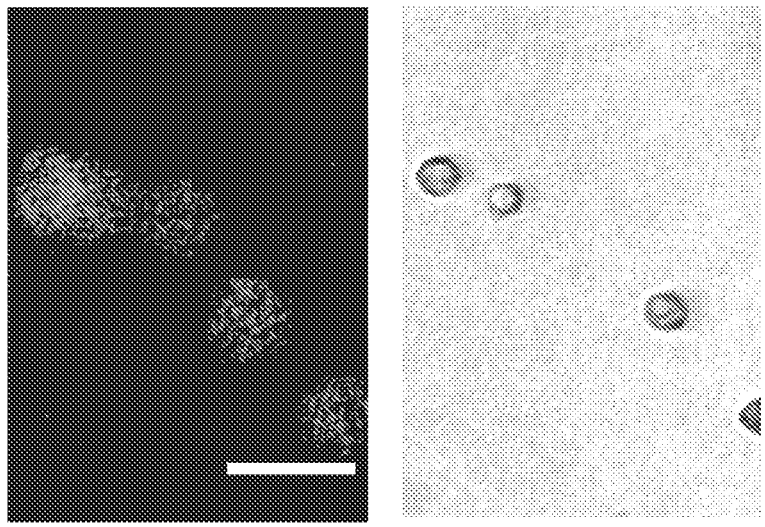
FIG. 18A is set of fluorescent and matching bright field images of D1s encapsulated in 54 kDa alginate.
Figure 18B:
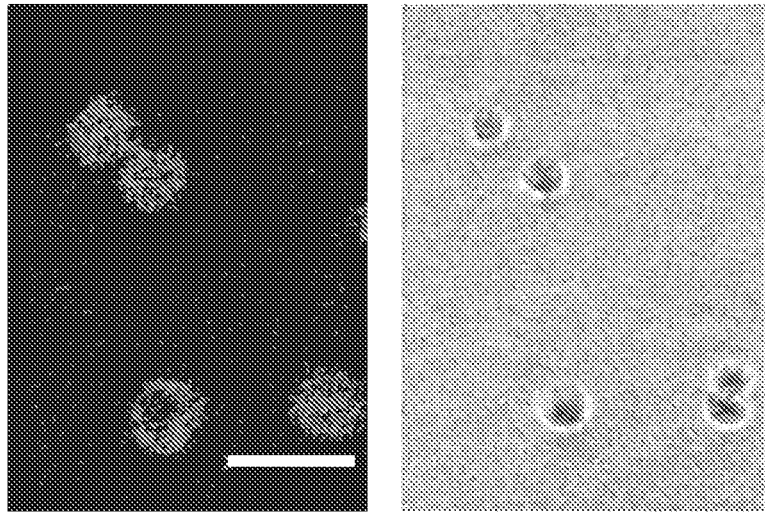
FIG. 18B is a set of fluorescent and matching bright field images of D1s encapsulated in 139 kDa alginate.
Figure 18C:
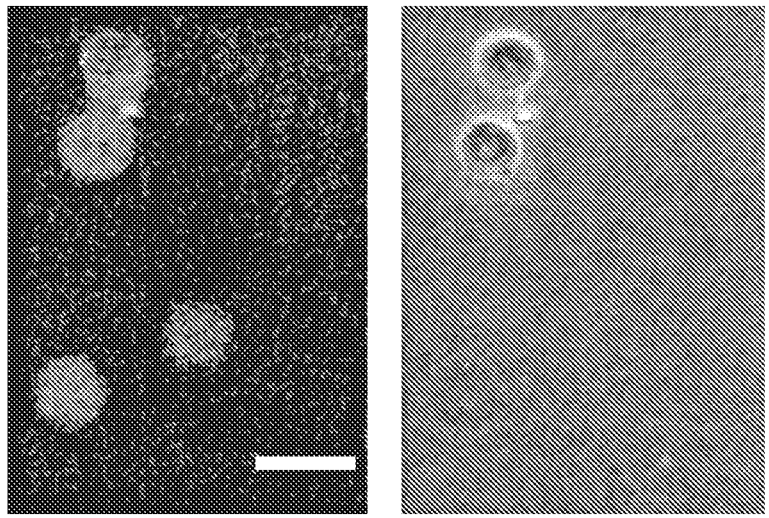
FIG. 18C is a set of fluorescent and matching bright field images of D1s encapsulated in 232 kDa alginate. The alginate is labeled with a red fluorophore in FIGS. 18A and B, and a green fluorophore in FIG. 18C.
Figure 18D:
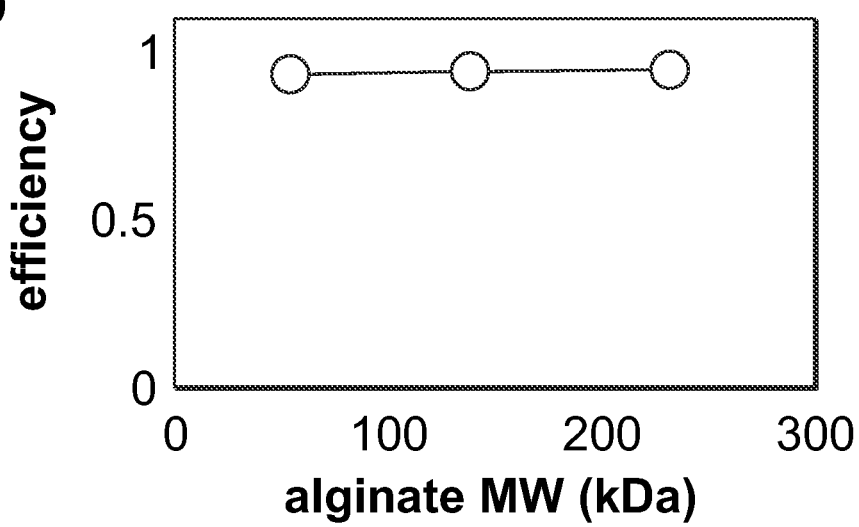
FIG. 18D is a graph showing the comparison of the fraction of cells encapsulated (efficiency) as a function of polymer molecular weight.
Figure 18E:
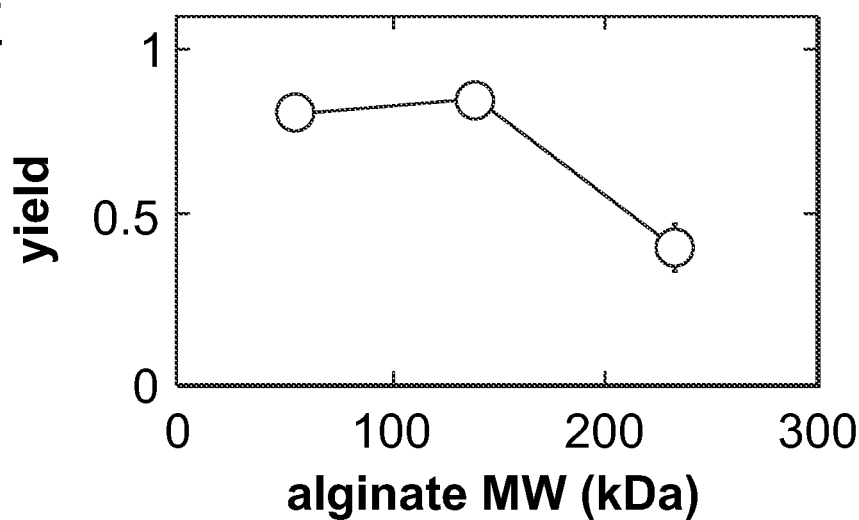
FIG. 18E is a graph showing the fraction of microgels containing cells (yield) as a function of polymer molecular weight.
Figure 18F:
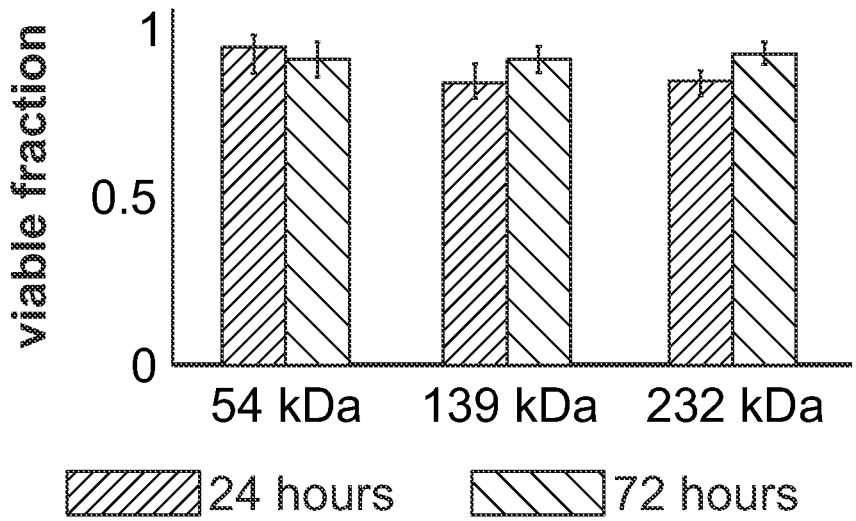
FIG. 18F is a graph showing the fraction of viable cells over time as a function of polymer molecular weight.
Figure 18G:
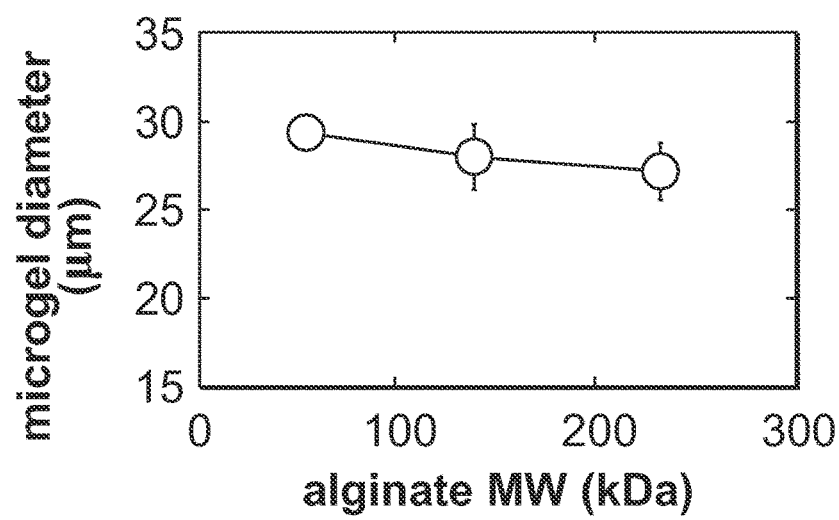
FIG. 18G is a graph showing the hydrogel capsule size as a function of polymer molecular weight. Differences in the fraction of cells encapsulated and the fraction of viable cells depending on molecular weight were not significantly different (chi square test). Initial hydrogel capsule size difference was significant (1-way ANOVA, $p<0.05$). Yield in 232 kDa alginate was significantly lower than other conditions, as analyzed by chi square test, $p<0.01$.
Figure 18H:
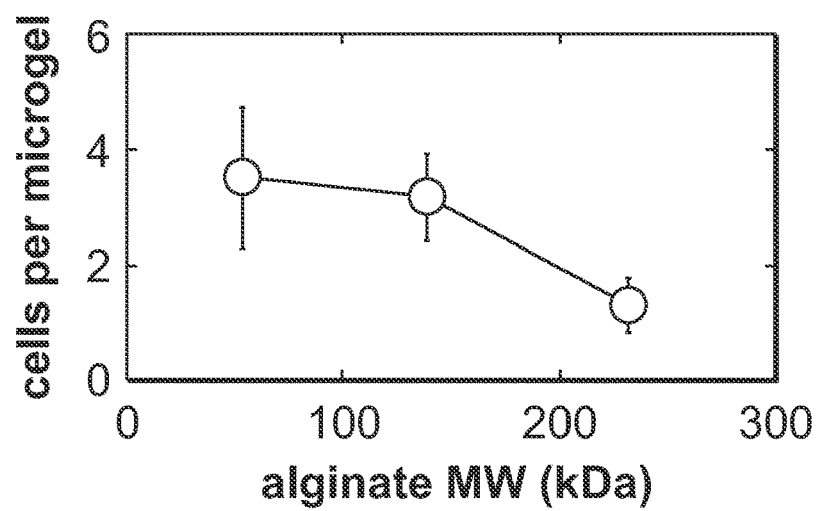
FIG. 18H is a graph showing the average number of cells per microgel.

Cells encapsulated in different molecular weight alginates were imaged (FIGS. 18A-C; 22A-C). The efficiencies of encapsulation (fraction of cells encapsulated) did not vary significantly among different molecular weights of alginate (FIG. 18D). The encapsulation yield (fraction of hydrogel capsule beads containing cells) of the 232 kDa alginate was significantly lower than that of lower MW polymers (FIG. 18E). This difference is likely due to increased shear from the higher viscosity of high MW alginate. For all MWs, the encapsulation yield was much higher than that obtained by direct injection into a microfluidic device without pre-coating of nanoparticles. The long term viabilities of encapsulated D1 cells showed no significant differences among the three MW polymers (FIG. 18F). The initial hydrogel capsule sizes were found to exhibit slight, but significant differences, depending on polymer MW (FIG. 18G).

Figure 18I:
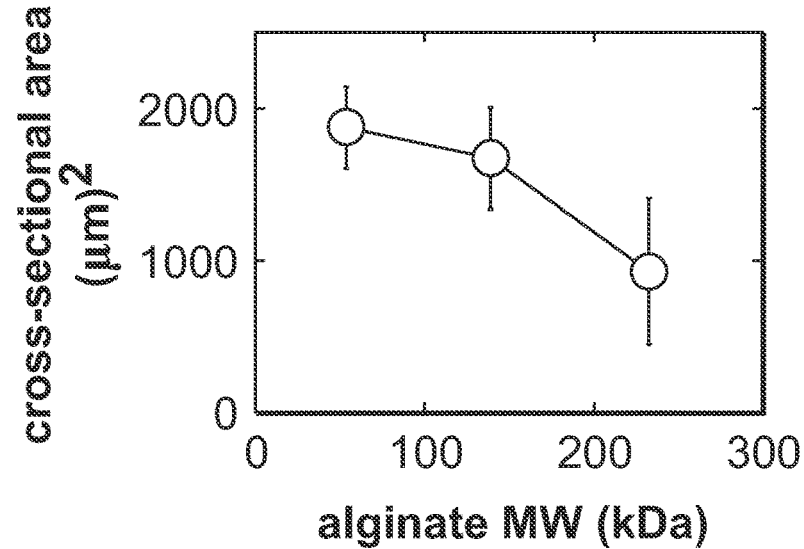
FIG. 18I is a graph showing the microgel size after 3 days of culture (1-way ANOVA, p<0.01) are shown.
Figure 18J:
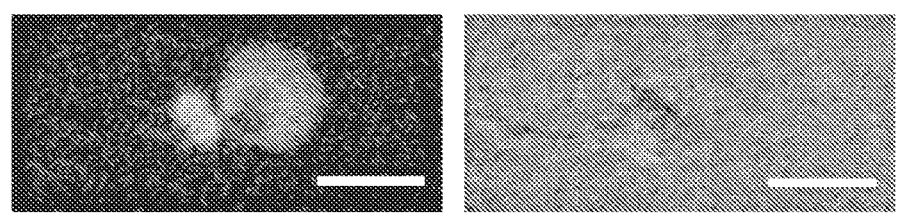
FIG. 18J is a fluorescent image (left) and a brightfield image (right) of a cell leaving its microgel. Red, alginate; blue, nucleus; green, actin; scale bar: 50 microns.
Figure 18K:
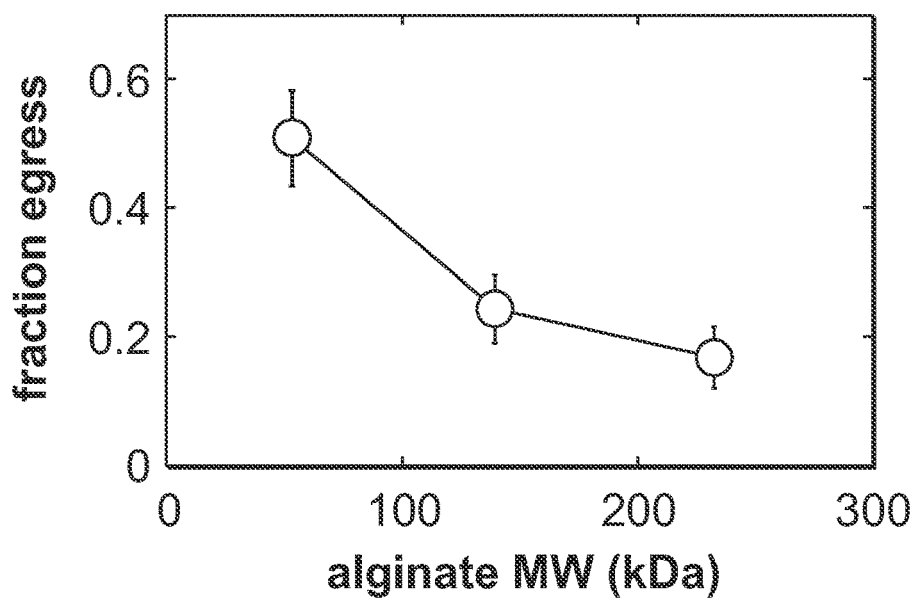
FIG. 18K is a graph showing the fraction of cells that regressed from microgels formed from alginate of different molecular weights into surrounding collagen gel. Differences between conditions were statistically significant (chi-square test, df=2, p<0.01).

Cells in hydrogel capsules formed from varying polymer molecular weight were then encapsulated in a 11 mm×1.1 mm collagen gel and cultured for one or three days. The diameter and the number of cells per cell-containing hydrogel capsule were quantified after three days of culture. Significantly fewer cells per hydrogel capsule were found after three days of culture in 232 kDa alginate as compared to the lower MW polymers (FIGS. 18H and 22A-C). This difference in cell number was reflected in hydrogel capsule size, as hydrogel capsules formed from 54 kDa and 139 kDa alginate appeared to have increased in size over this time more than hydrogel capsules formed from the 232 kDa polymer (FIG. 18I). Additionally, after one day of culture, the number of empty alginate hydrogel capsules and the number of hydrogel capsules that still contained cells were counted to determine the fraction of cells that had exited hydrogel capsules (FIG. 18J). The fraction of cells that regressed was significantly higher in 139 kDa and 54 kDa alginate beads than in 232 kDa alginate, showing that alginate MW can be used to control cell trafficking out of hydrogel capsules (FIG. 18K).

Figure 18L:
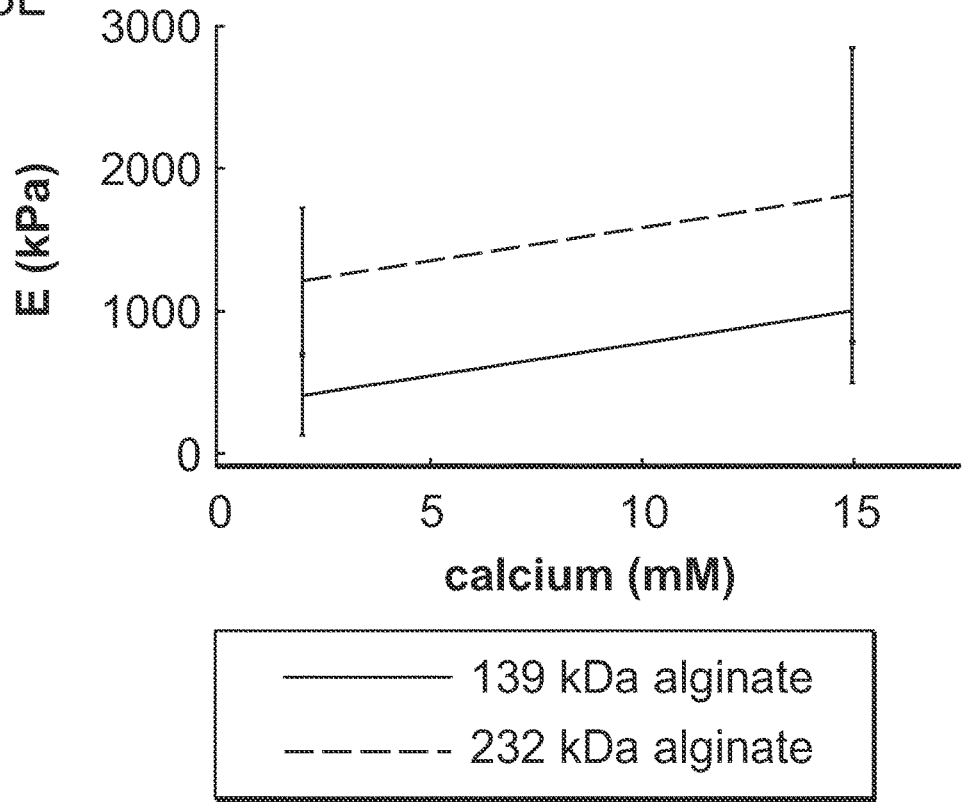
FIG. 18L is a graph showing the elastic moduli of microgels that were treated post-encapsulation with solutions containing different concentrations of calcium chloride.

As extracellular matrix mechanics have been shown to potently influence cell behavior, the ability of hydrogel capsules to be further crosslinked post-fabrication was also analyzed. D1s were encapsulated in 139 kDa and 232 kDa alginate hydrogel capsules and subsequently exposed to 2 mM or 15 mM calcium chloride. The elastic moduli of the hydrogel capsules were then measured using atomic force microscopy (AFM). In hydrogel capsules of both molecular weights, addition of calcium post-fabrication led to increased elastic moduli (FIG. 18L).

Figure 22A:
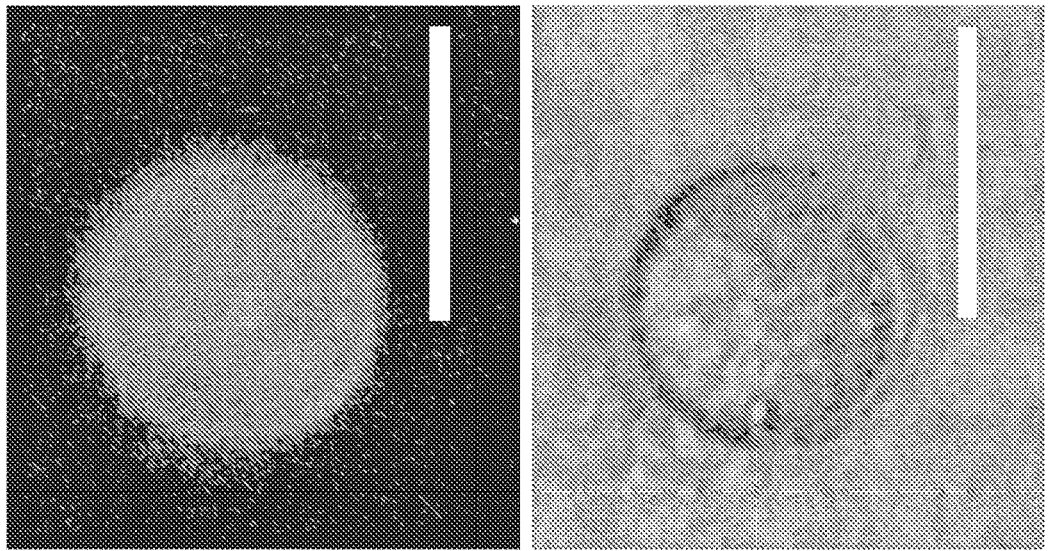
FIG. 22A is a set of images of D1 cells encapsulated in 54 kDa alginate after 3 days of culture.
Figure 22B:
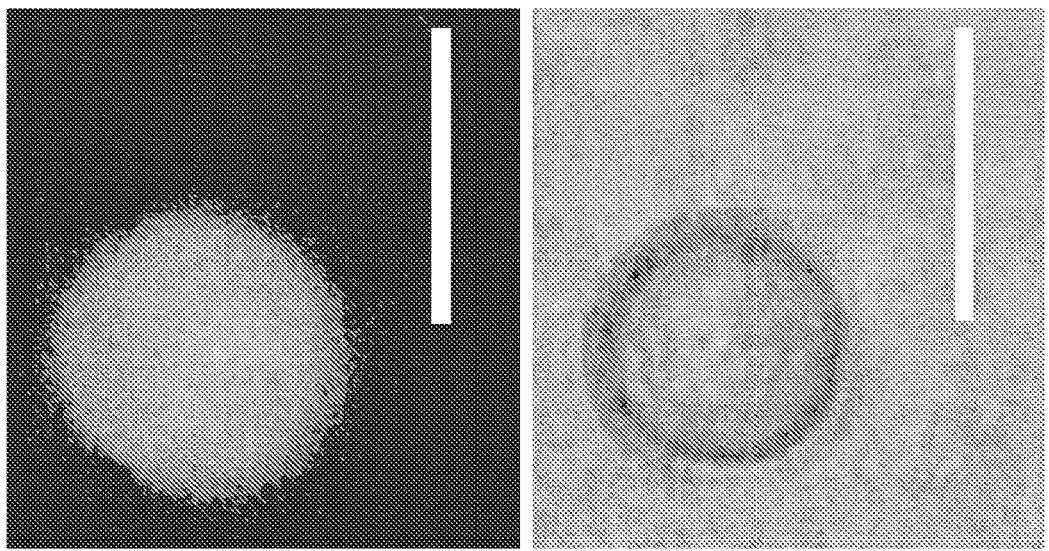
FIG. 22B is a set of images of D1 cells encapsulated in 139 kDa alginate after 3 days of culture.
Figure 22C:
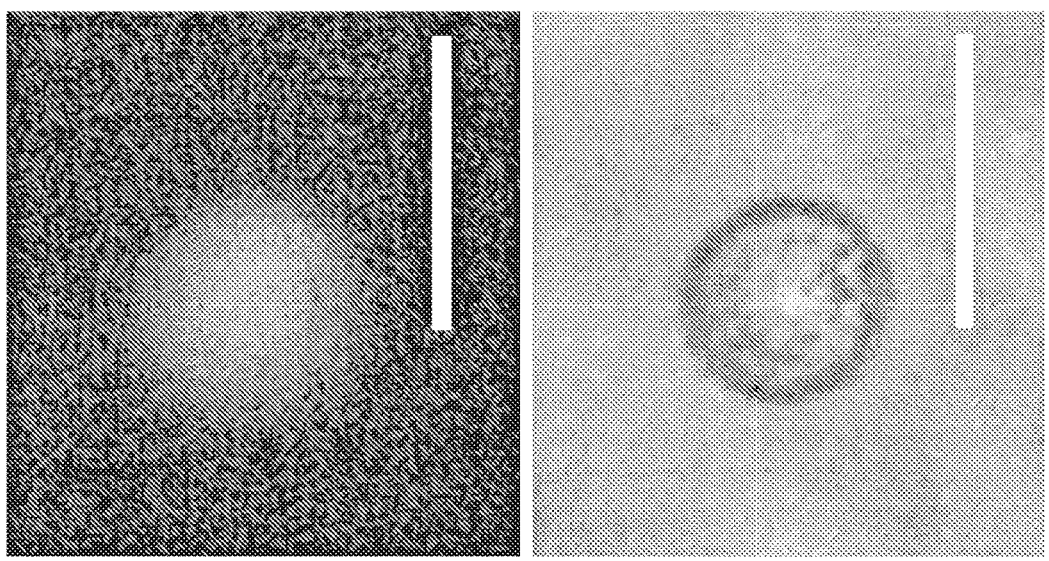
FIG. 22C is a set of images of D1 cells encapsulated in 232 kDa alginate after 3 days of culture. Scale bar, 30 microns. Top: fluorescence; bottom: brightfield.
Figure 22D:
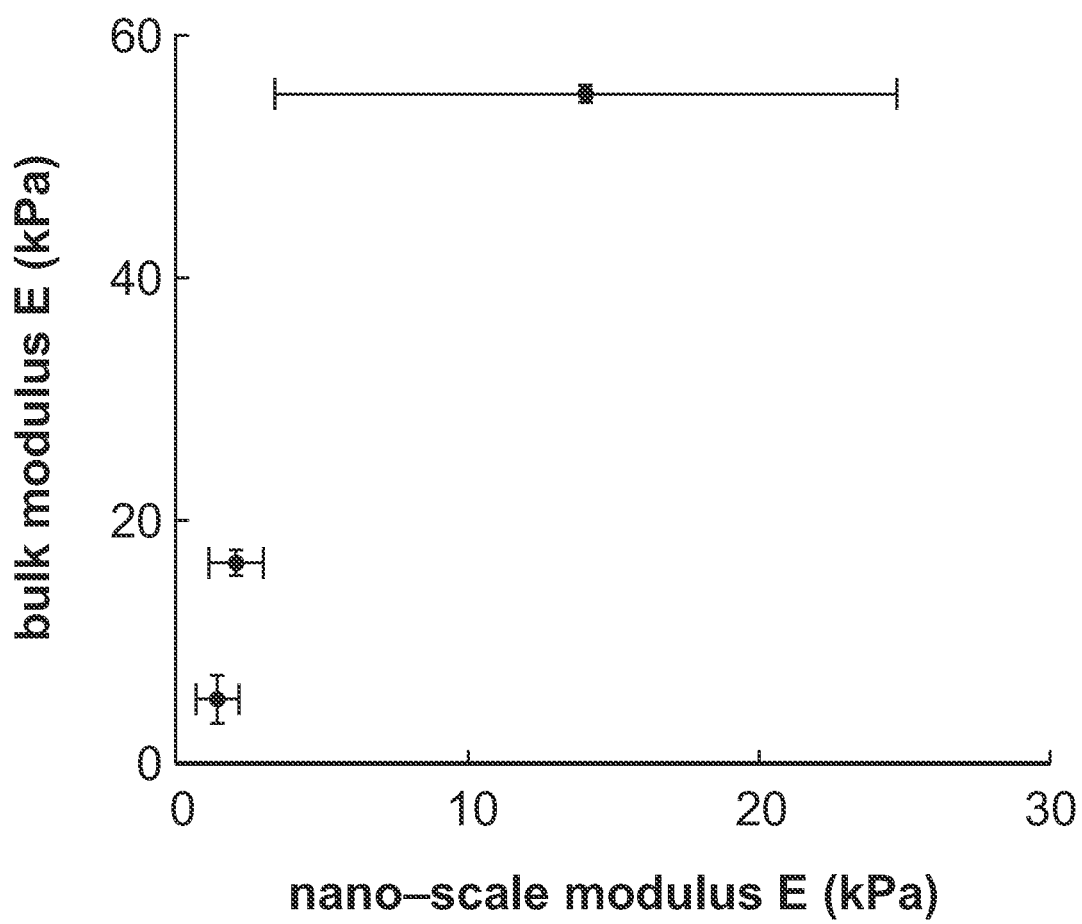
FIG. 22D is a graph showing measurements of bulk modulus, as assessed by an Instron mechanical apparatus, as a function of nano-scale modulus of the same hydrogel, as assessed by AFM.

To compare nanoscale measurements of elastic modulus with those obtained at a macroscopic scale, 10 mm×2 mm alginate hydrogels were fabricated, and their elastic moduli were measured both with AFM and with an Instron mechanical apparatus (FIG. 22D).

Example 10: Encapsulating Cells in Other Polymers

Figure 23A:
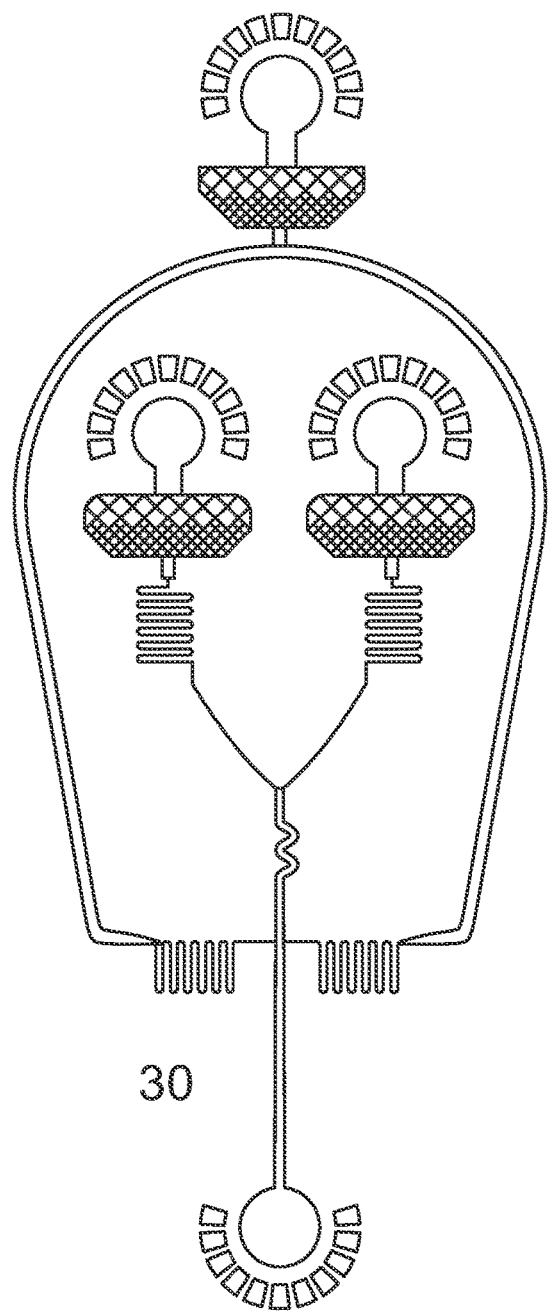
FIG. 23A is a schematic of microfluidic device used for fabrication of fibrin and fibrin-alginate hydrogel capsules.

As hybrid hydrogels have been shown to potentially combine beneficial properties of each of their components, the ability to form collagen-alginate and fibrin-alginate hybrid hydrogel capsules with the methods described herein was tested. As cross-linking of the secondary hydrogel (either collagen or fibrin) was not dependent on the presence of calcium, cells were directly encapsulated in hybrid hydrogel capsules without the nanoparticle pre-coating step. Cell-encapsulating collagen-alginate hybrid hydrogel capsules were fabricated by mixing calcium carbonate nanoparticles, D1 cells, alginate, and neutral-pH liquid collagen before injection into the microfluidic device at 4° C. As fibrin cross-linking relies on the catalytic action of thrombin, fibrin-alginate components were separated into two streams and combined above the T-junction (see, e.g., FIG. 23A). The acid was added after the emulsion formed in the fabrication of fibrin-alginate hydrogel capsules, as cross-linking of alginate prior to fibrin cross-linking resulted in phase separation of the two polymers. The hybrid emulsions were incubated at 37° C. to allow for the protein component to cross-link before the emulsion was broken.

Figure 19K:
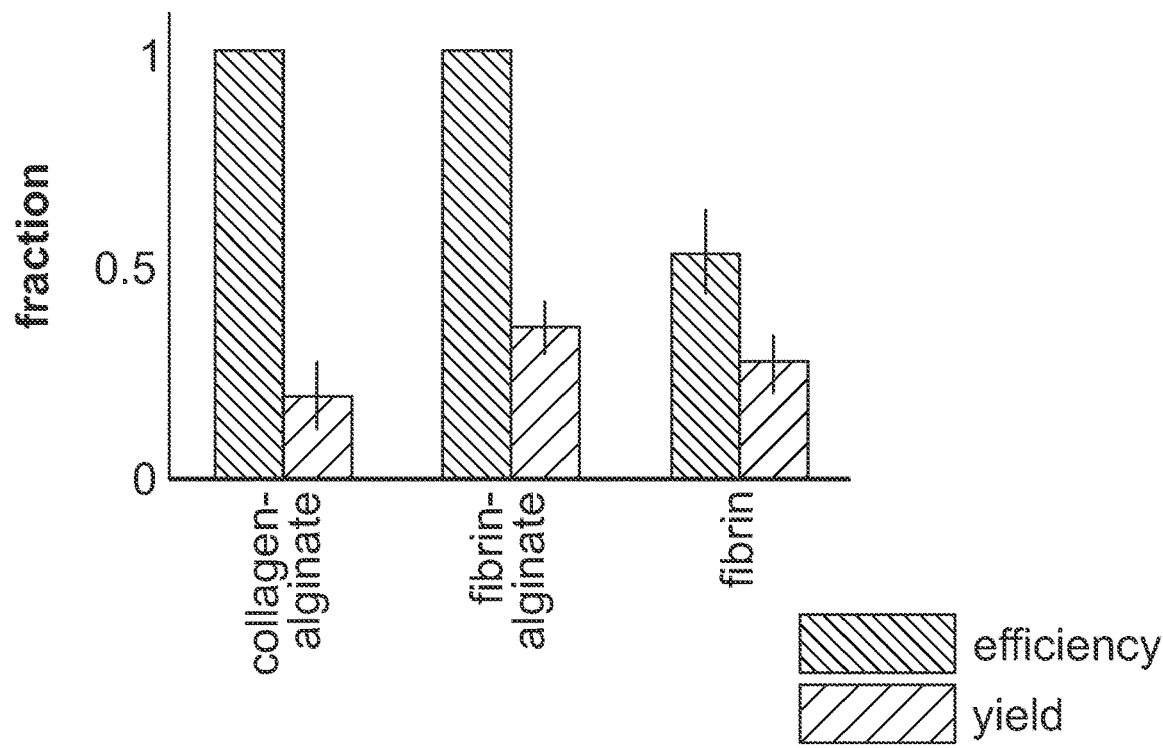
FIG. 19K is a graph showing encapsulation efficiency and yield in collagen-alginate, fibrin-alginate, and fibrin microgels.
Figure 19I:
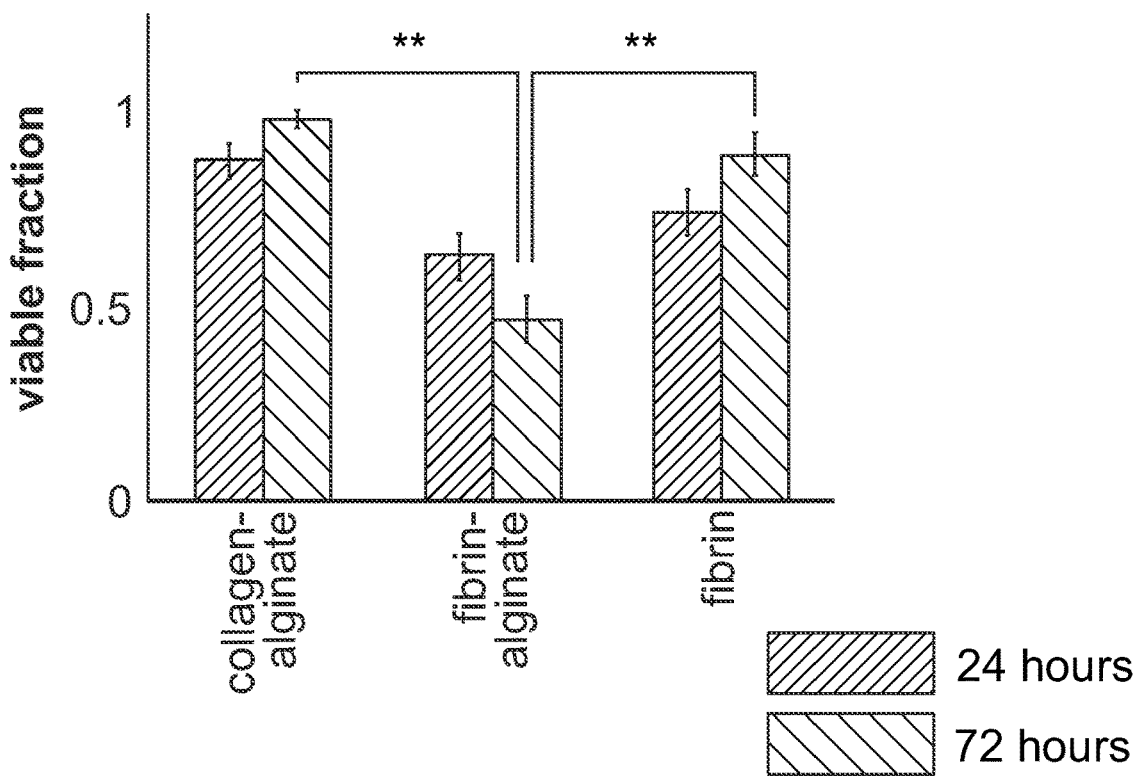
FIG. 19I is a transmitted light image of the cell in FIG. 19H. Scale bar 50 microns.

Confocal images were taken of cell-encapsulating hybrid hydrogel capsules to assess the structure and distribution of components within each hydrogel capsule. Microscopy revealed collagen and fibrin fibrils within their respective hydrogel capsules (FIG. 19A-B). The pixel intensities of the alginate component of collagen-alginate hydrogel capsules followed a unimodal distribution (FIG. 19C), indicating that there was no phase separation of the two components. The collagen and alginate components per hydrogel capsule were quantified (FIG. 19D). The two components followed unimodal distributions, with a CV of 8.6% for alginate and 24% for collagen.

Figure 23B:
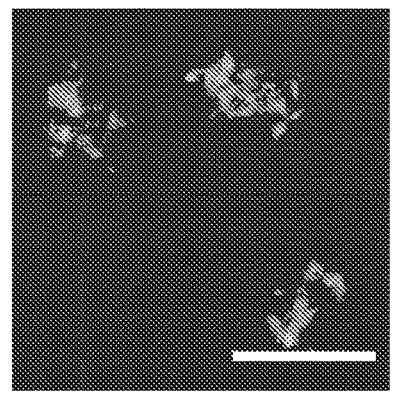
FIG. 23B is a representative image of a collagen-alginate hydrogel capsule following EDTA treatment.
Figure 23C:
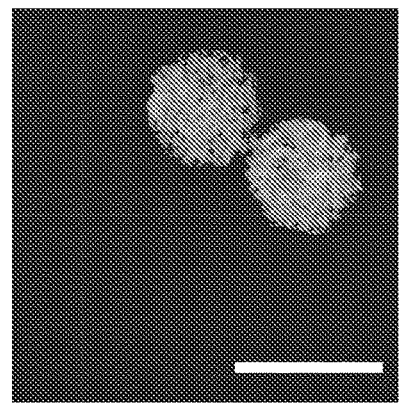
FIG. 23C is a representative image of a fibrin-alginate hydrogel capsule following EDTA treatment.

The histogram of pixel intensities of the alginate component of fibrin-alginate hydrogel capsules (FIG. 19E) exhibited greater spread than that of collagen-alginate hydrogel capsules, with a tail towards lower intensity values. This was reflected in the confocal image of fibrin-alginate hydrogel capsules, in which the alginate component was visibly heterogeneous (FIG. 19B). When averaged per 10 pixels, corresponding to 4 microns, the distribution of alginate intensities exhibited a tighter peak, indicating that the variation in polymer concentration occurred on a length scale of 4 microns (FIG. 19F). Quantification of the fibrin and alginate components per hydrogel capsule revealed greater variance than in collagen-alginate hydrogel capsules, with 11% of the hydrogel capsules lacking a fibrin component (FIG. 19G). The cross-linking integrity of the protein component of both hybrid hydrogel capsules was tested by exposure to ethylenediaminetetraacetic acid (EDTA), a calcium chelator (FIG. 19G-H). Collagen-alginate hydrogel capsules exposed to EDTA underwent a 10% decrease in intensity in the remaining collagen portion and a 46% reduction in the number of distinct hydrogel capsules, either through disintegration or combination with other hydrogel capsules. Remaining hydrogel capsules retained their fibrillar structure but lost their circular morphology (FIG. 23B). Fibrin-alginate hydrogel capsules experienced only a 16% reduction in number, and retained their circular morphology (FIG. 23C).

Figure 20A:
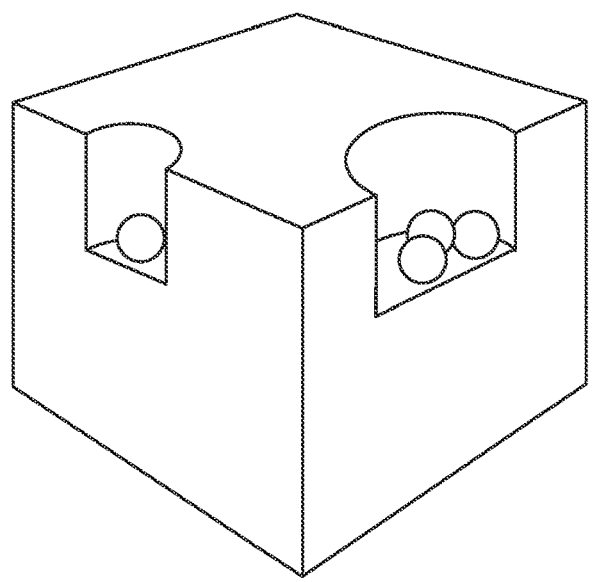
FIG. 20A is a schematic of a culture apparatus, showing alginate-encapsulated cells settled in PDMS microwells of different diameters.
Figure 20B:
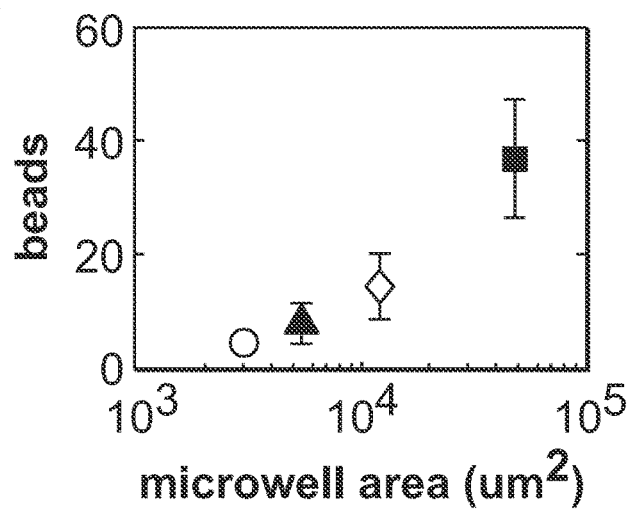
FIG. 20B is a graph showing the number of hydrogel capsules per 100-um deep microwells as a function of microwell area.
Figure 20C:
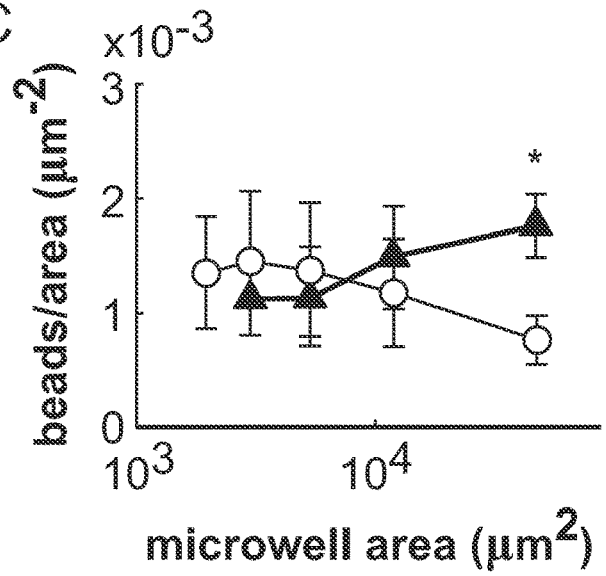
FIG. 20C is a graph of hydrogel capsule area density as a function of microwell area, in 100-µm deep (circles) and 200-µm deep (triangles) microwells. *=p<0.05.

Example 11: Constructing Defined Mesoscale Tissues to Study MSC Osteogenic Differentiation To assess the behavior of multiple encapsulated cells when assembled together, microwells of PDMS were used to template and culture hydrogel capsules (FIG. 20A). PDMS microwell diameters were specified to range from 50-221 µm and arranged such that, per 750×750 µm area, the surface area of microwells remained equal, so as to equalize the macroscopic density of seeded cells. Encapsulated D1 cells were seeded into microwells by gravitational sedimentation. The number of cells that settled in each microwell depended on the microwell diameter, and ranged, on average, from 2.6 to 37 cells (FIG. 20B). Compared to larger microwells, significantly fewer hydrogel capsules per well area settled in the smallest 200 µm-deep microwells, possibly due to more inefficient packing of hydrogel capsules as the well diameter approached the hydrogel capsule size. Cell retention in smaller microwells was not significantly different between well depths. However, as PDMS is non-adherent, microwells needed to be sufficiently deep to prevent sample loss during washing and media changes. 200 µm-deep microwells retained significantly more hydrogel capsules in the largest-diameter microwells than 100 µm-deep microwells (FIG. 20C).

To assess osteogenesis and the relationship between assemblage size and D1 osteogenic differentiation, encapsulated D1 cells were fixed and stained for alkaline phosphatase (ALP) after 6 days of culture in differentiation medium. Confocal imaging revealed a combination of cells that had remained inside hydrogel capsules, and cells that had egressed from the hydrogel capsules and colonized the outside surfaces of the hydrogel capsules (FIG. 20D). ALP expression was observed in microwells of all sizes but correlated with the number of hydrogel capsules per well (r=0.76) (FIG. 20E).

Example 12: Intravenous Delivery of Hydrogel Encapsulated Cells

Figure 24A:
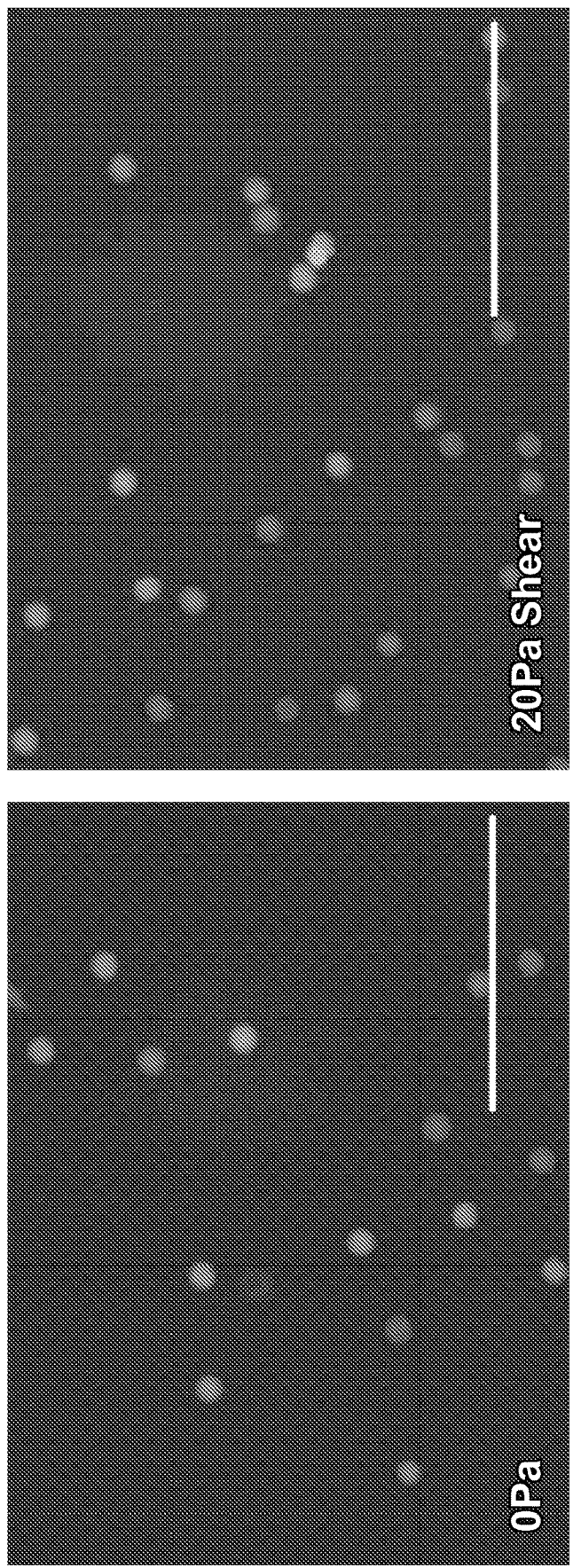
FIG. 24A is a set of images showing the effects of in vitro shear force on the microscale integrity of soft hydrogel capsules (E~300 Pa).
Figure 24C:
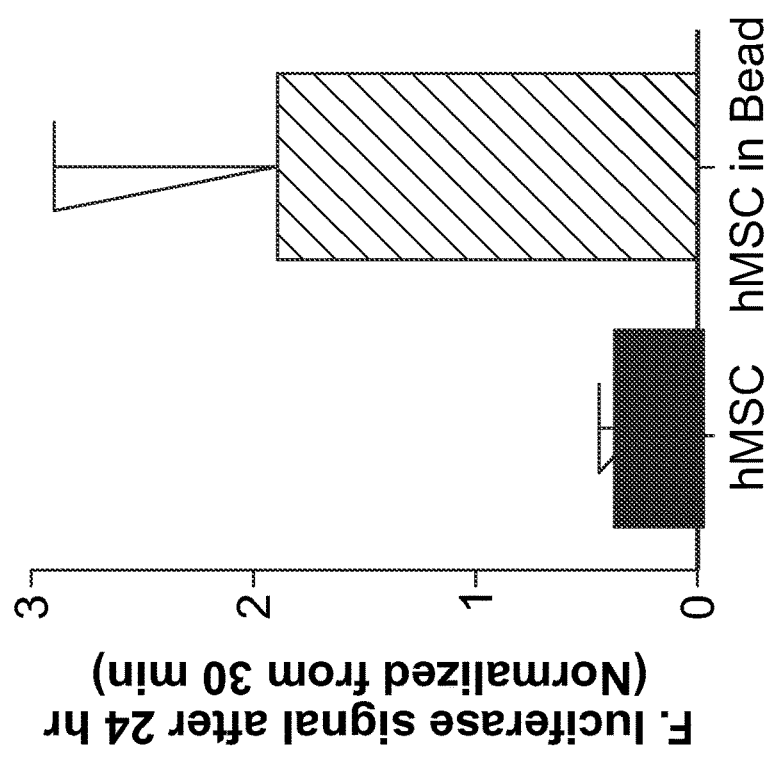
FIG. 24C is a bar graph showing the biodistribution of human MSCs overexpressing Firefly luciferase with or without hydrogel encapsulation after 24 hours of intravenous injection. The bioluminescence signals from lungs were measured using IVIS at 24 hours post-injection and normalized against those at 30 min.
Figure 24B:
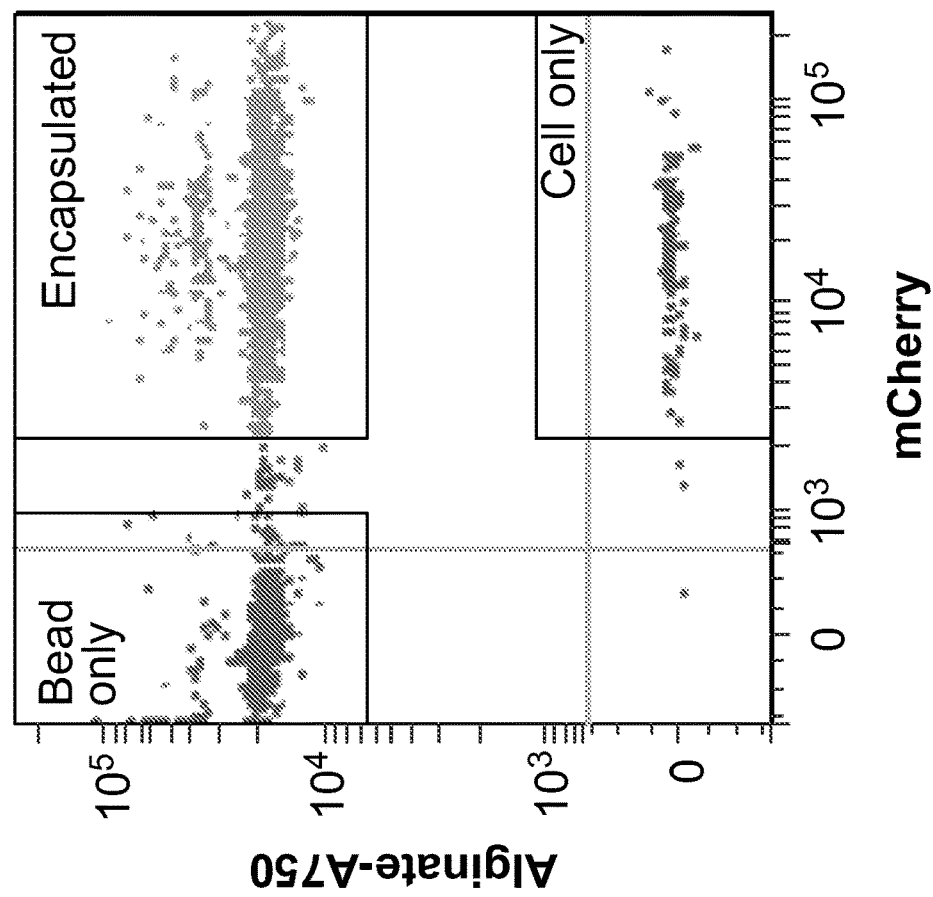
FIG. 24B is a diagram showing the results of flow cytometry analysis of human MSCs encapsulated in 139-kDa alginate hydrogel capsule revealed ~70% efficiency and ~75% yield.
Figure 25A:
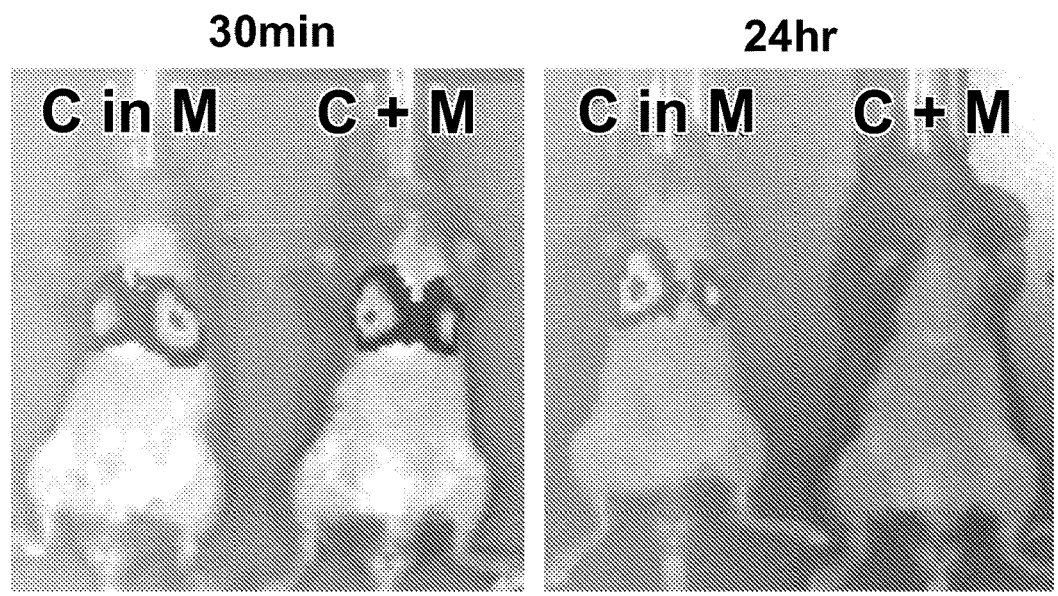
FIG. 25A is a set of representative bioluminescence images showing the biodistribution of mMSCs overexpressing Firefly Luciferase with or without hydrogel encapsulation after intravenous injection. "C in M": Encapsulated cells ("Cell in Microgel"), "C+M": Cells mixed with empty hydrogel capsules ("Cell+Microgel").
Figure 25B:
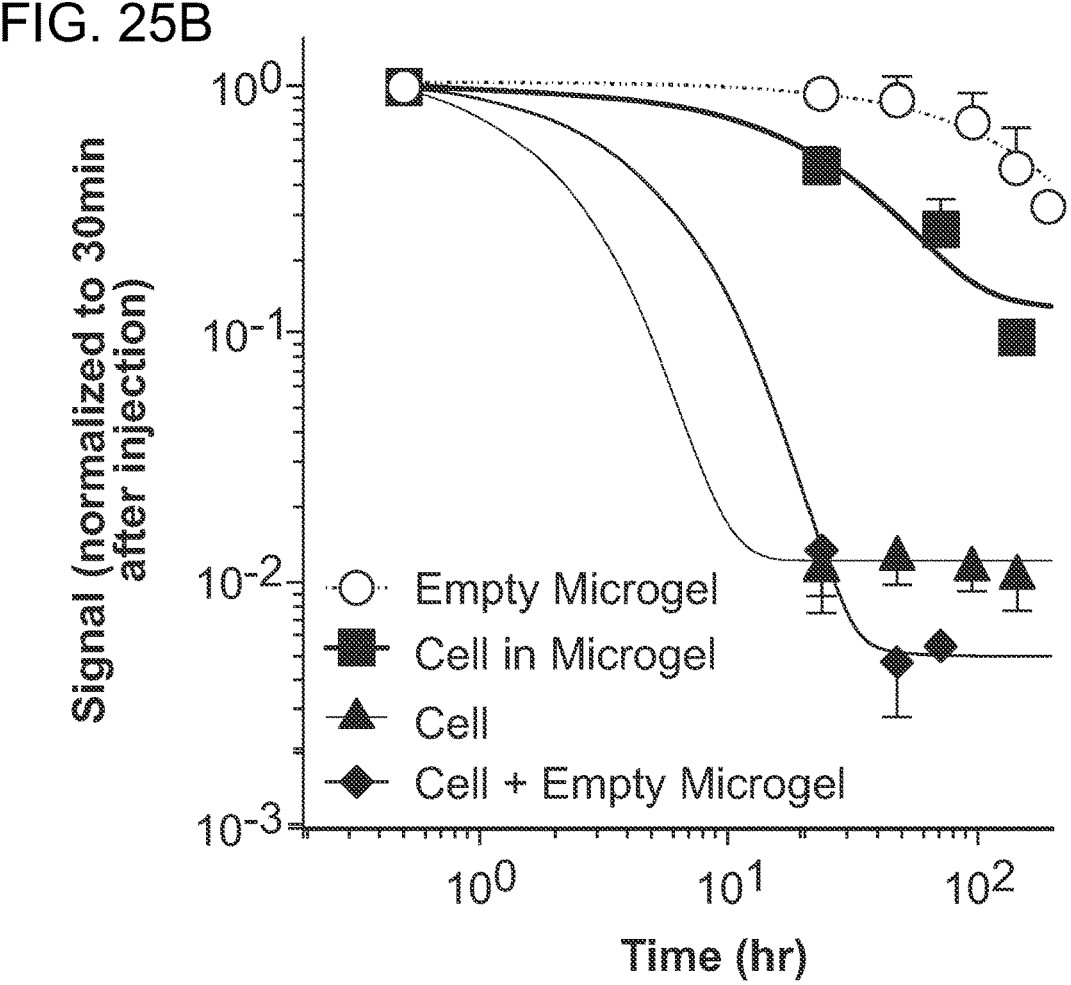
FIG. 25B is a graph showing the clearance kinetics of singly encapsulated mMSCs after intravenous injection compared to cells alone, cells mixed with hydrogel capsules, and empty hydrogel capsules. For each group, all the values were normalized by the value at 30 min. The signals from lungs were measured. The fluorescence signals were measured for empty hydrogel capsules, while the luminescence signals were measured for hydrogel capsules that contained cells. The data were fit to Y=(1.00−Plateau)*exp(−k*t)+Plateau. For each group, $t_{1/2}$ (ln(2)/k, hr) is: Empty Microgel=142.6; Cell in MIcrogel=30.74; Cell=2.59; Cell+Empty Microgel=2.85, n≥5 recipients.

The small size of hydrogel capsules fabricated with this technique permits, for the first time, the intravenous delivery of hydrogel encapsulated cells. The large majority of clinical trials currently administering MSCs to patients utilize i.v. infusion of bare cells (Bailey et al., 2014., *Nat. Biotechol.* 32, 721-723). While polymeric encapsulation by droplet extrusion was previously explored for prolonging the delivery of multicellular clusters for in vivo transplantation, a number of issues were reported (Orive et al. 2003, *Nat. Med.* 9, 104-107; Ma et al., 2013, *Adv. Healthc. Mater.* 2, 667-672; Pareta et al., 2014, Microencapsulation Technology. In: Regenerative Medicine Applications in Organ Transplantation. Edited by Orlando G., Lerut J., Soker S. & Stratta, R.J. 1st Ed. Academic Press, Boston, pages 627-635) including that the large microparticles >100 μm generated with previous methods (Karoubi, 2009, *Biomaterials* 30, 5445-5455) precluded i.v. infusion. To first determine if the hydrogel capsules could retain structural integrity in circulation, they were subjected to shear forces 10 times higher than arterial pressure (~2 Pa). Even soft (E=300 Pa) hydrogel capsules were found to withstand this level of shear (FIG. 24A). To explore the utility of this approach in improving delivery of allogeneic donor cells, mMSCs derived from Balb/c mice were injected into C57/BL6 mice. Consistent with previous observations (Fischer et al. 2009, Stem Cells Dev. 18, 683-691), mMSCs were localized in lungs shortly after the i.v. injection, likely due to their entrapment into small capillaries (~3 μm) (FIG. 25A). Strikingly, the half-life of donor cell clearance was increased by ~10 fold when cells were encapsulated, but not when cells were mixed with empty hydrogel capsules (FIG. 25A, 25B). This finding indicates that encapsulation of allogeneic donor cells dramatically improves their maintenance in vivo after i.v. infusion. Cell-free hydrogel capsules demonstrated similar maintenance, suggesting that the durability of the encapsulating hydrogel may set the upper limit to the survival of the encapsulated cells. While MSCs are considered immuno-privileged, some studies have shown that allogeneic transplantation leads to immune rejection of donor MSCs (Eliopoulos et al., 2005, *Blood* 106, 4057-4065; Nauta et al., 2006, *Blood* 108, 2114-2120); encapsulation in these thin gels can enable cells to bypass rejection. Human MSCs (hMSC) encapsulated and injected in the immunocompromised NOD/SCID/IL2γ$^{-/-}$ (NSG) mice yielded similar results, with hydrogel encapsulation even enhancing the bioluminescence signal after a day of injection in this model (FIG. 24B-C).

Figure 24D:
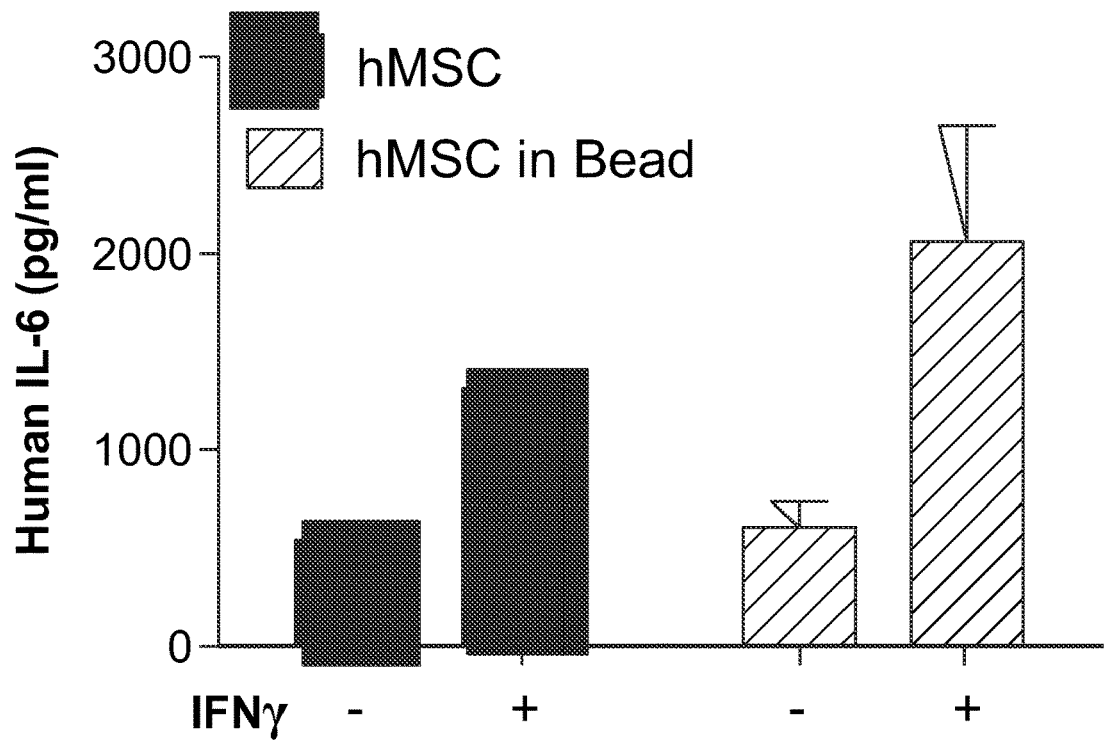
FIG. 24D is a bar graph showing IL-6 secretion of singly encapsulated human MSCs in vitro after 1 day of culture.
Figure 24E:
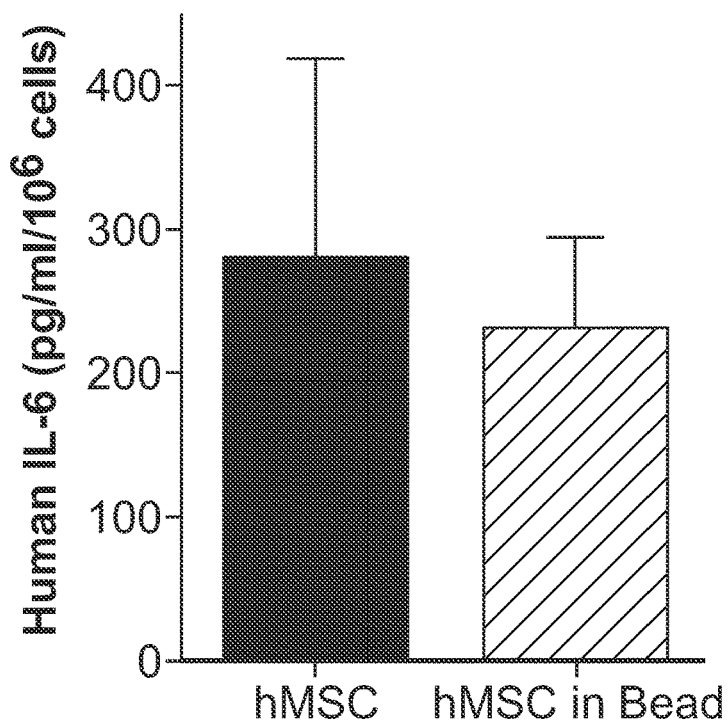
FIG. 24E is a bar graph showing levels of IL-6 secreted into blood plasma by human MSCs encapsulated into 139-kDa alginate 4 hours after injection.

Studies were next performed to test whether prolonged cell delivery was accompanied by sustained systemic presence of soluble factors from allogeneic donor cells. mMSCs were genetically modified to express *Gaussia* luciferase (Gluc, ~20 kD), which is constitutively secreted (Wurdinger, 2008, *Nat. Methods* 5, 171-173). Intravenous injection of encapsulated cells led to a progressive increase in blood Gluc levels, with a peak at week 2 (FIG. 25C). In contrast, injection of unencapsulated cells led to much lower blood levels of Gluc; the total amount of Gluc in blood over 2 weeks was increased by ~10 fold with encapsulation. To evaluate whether this approach also results in sustained systemic secretion of native soluble factors from donor cells, singly encapsulated hMSCs were i.v. injected into NSG mice. The encapsulation procedure did not compromise IL-6 secretion by human MSCs either constitutively or under stimulation by IFNγ (FIG. 24D). Injection of cells encapsulated in the higher, 232-kDa MW polymer increased the total concentration of human IL-6 in blood plasma at 24 hours by ~2 fold, as compared to unencapsulated cells (FIG. 25D). Interestingly, encapsulation of cells in the lower, 139-kDa MW polymer led to no differences in plasma levels of human IL-6 (FIG. 24E); as cells in hydrogel capsules fabricated from lower MW polymers showed greater egress in vitro following encapsulation, this result demonstrates that hMSCs encapsulated in this polymer may have regressed and experienced immune clearance by the host.

Example 13: Matrix Stiffness as a Modulator of Soluble Factor Secretion from Encapsulated Cells Secretion of soluble factors from the cells encapsulated in the hydrogel capsules of the invention may be modulated by changing the stiffness of the hydrogel capsules. Human primary bone marrow MSCs were encapsulated in alginate hydrogels containing RGD cross-links for cell attachment and characterized by different stiffness (soft=0.3~1 kPa; stiff=>30 kPa). The MSCs were cultured in media containing DMEM, 1% GlutaMax and 1% Penn/Strep in the presence or absence of exogenous inflammatory factors (INF-γ, TNF-α and LPS). The media were collected at 24, 48 and 72 hours and subjected to ELISA assays in order to evaluate the total quantity of secreted factors, and the results are shown in FIGS. 26A, 26B and 26C. Specifically, the results shown in FIG. 26A demonstrate that MSCs encapsulated in soft hydrogels secrete a greater amount of IL-6 than MSCs encapsulated in stiff hydrogels, and that stimulation with INF-γ further increases the amount of the secreted IL-6 in a dose-dependent manner. The results shown in FIG. 26B demonstrate that MSCs encapsulated in soft hydrogels secrete a greater amount of MCP-1 (CCL2) chemokine than MSCs encapsulated in stiff hydrogels and that stimulation with TNF-α further increases the amount of the secreted MCP-1 over time. The results shown in FIG. 26C, left panel, demonstrate that MSCs encapsulated in stiff hydrogels secrete a greater amount of SCF over time, and that stimulation with LPS further increases the amount of the secreted SCF over time. Finally, the results shown in FIG. 26C, right panel show that MSCs encapsulated in soft hydrogels secrete a greater amount of TGF-β than MSCs encapsulated in stiff hydrogels, in the absence of further stimulation by exogenous factors.

Figure 27A:
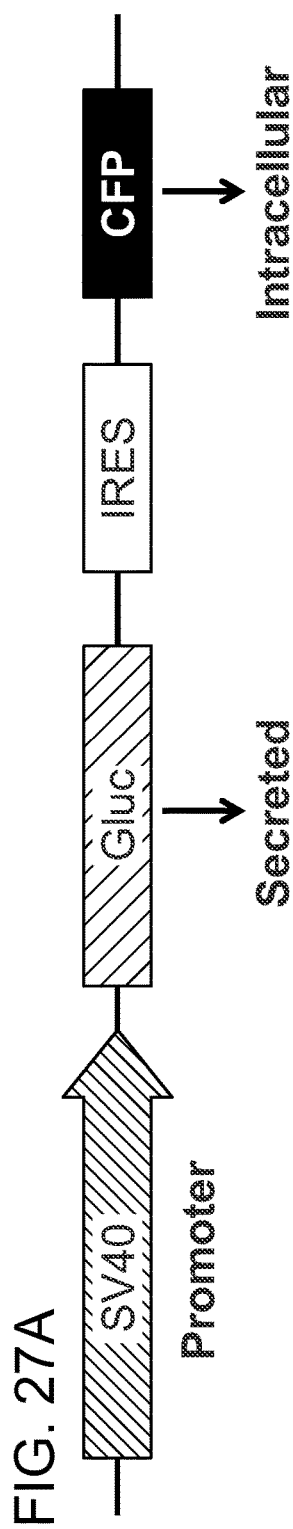
FIG. 27A is a schematic showing the structure of a DNA plasmid used to transduce mouse D1 MSCs. The DNA plasmid contains a secreted form of *Gaussia* Luciferase and CFP. Both genes are separated by IRES and their expression is driven by the constitutive promoter SV40.
Figure 27C:
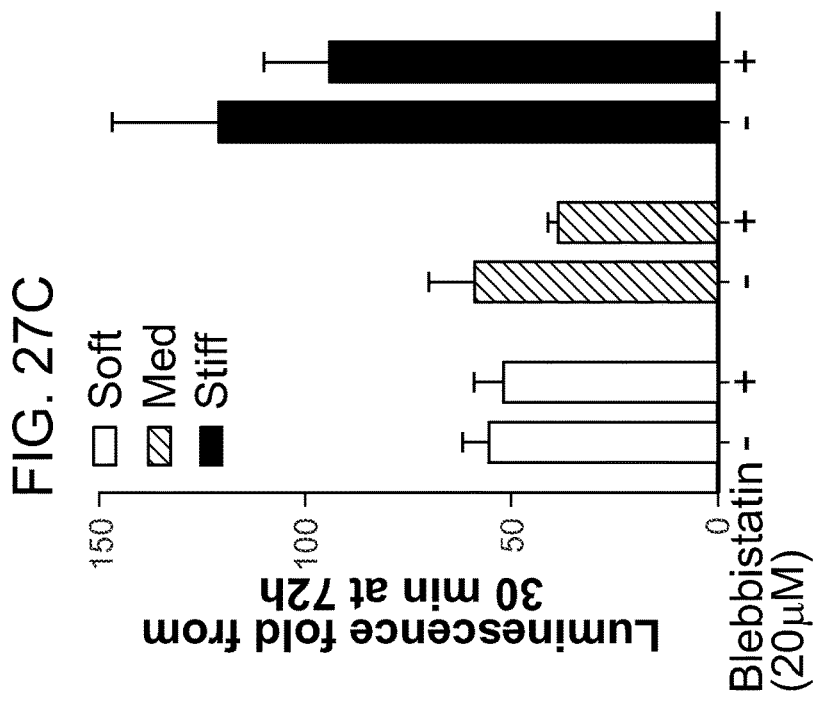
FIG. 27C is a bar graph showing that secretion of *Gaussia* Luciferase from the transduced mouse D1 MSCs is partially suppressed by treatment with myosin-II inhibitor blebbistatin.
Figure 27B:
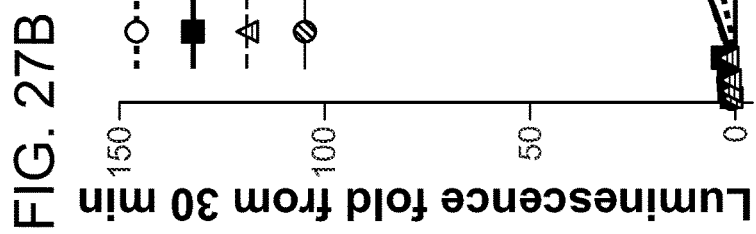
FIG. 27B is a graph showing the total amount of *Gaussia* Luciferase secreted from the mouse D1 MSCs transduced by the DNA plasmid shown in FIG. 27A and encapsulated in alginate hydrogels of different stiffness.

For luciferase experiments, mouse D1 MSCs were transduced with a DNA plasmid containing the DNA encoding the secreted form of luciferase (*Gaussia* Luciferase, ~20 kDa) and CFP gene sequences (as intracellular control). In the plasmid, both genes were separated by IRES, and their expression was driven by the constitutive promoter SV40, as shown in the schematic in FIG. 27A. The transduced cells were encapsulated in soft (0.3~1 kPa), medium (10~20 kPa), and stiff (>30 kPa) alginate hydrogels that contain an RGD sequence for cell adhesion. The total amount of the secreted *Gaussia* Luciferase was evaluated at 24, 48 and 72 hours by adding coelenterazine to each well that contains samples and integrating flash kinetics for 10 s. The results shown in FIG. 27B demonstrate that D1 cells encapsulated in stiff hydrogels secrete greater amounts of luciferase over time than D1 cells encapsulated in soft or medium hydrogels. The results shown in FIG. 27C demonstrate that the total luciferase secretion is partially inhibited by the addition of myosin-II inhibitor blebbistatin to the cells, and that the inhibitory effect of blebbistatin is more pronounced in stiff hydrogels as compared to soft and medium hydrogels.

EQUIVALENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. A composition comprising a plurality of hydrogel capsules, wherein at least 90% of the hydrogel capsules in the composition comprise a cell and a layer consisting of hydrogel encapsulating the cell;
   wherein at least 70% of the hydrogel capsules encapsulate a single cell;
   wherein the layer consisting of hydrogel encapsulating the cell has a thickness of less than 20 microns;
   wherein the hydrogel comprises an alginate polymer comprising a plurality of polymer chains cross-linked to each other using $Ca^{2+}$; and
   wherein the diameter of the hydrogel capsules is 50 microns or less.

2. The composition of claim 1, wherein the cell is a mesenchymal stem cell (MSC) or a progenitor thereof, a hematopoietic stem cell (HSC) or a progenitor thereof, or an endothelial progenitor cell.

3. The composition of claim 1, wherein the layer consisting of hydrogel encapsulating the cell is characterized by a stiffness of about 0.1 to about 500 kPa.

4. The composition of claim 1, wherein the composition is an injectable composition.

5. The composition of claim 4, wherein the composition is an injectable composition for intravenous injection.

6. A composition comprising a plurality of hydrogel capsules, wherein
   at least 90% of the hydrogel capsules in the composition comprise a cell and a layer consisting of hydrogel encapsulating the cell;
       wherein at least 70% of the hydrogel capsules comprise a single cell;
   wherein the layer consisting of hydrogel encapsulating said cell has a thickness of less than 10 microns;
   wherein the hydrogel comprises an alginate polymer comprising a plurality of polymer chains cross-linked to each other using $Ca^{2+}$; and
   wherein the diameter of the hydrogel capsules is 50 microns or less.

7. The composition of claim 6, wherein the cell is a mesenchymal stem cell (MSC) or a progenitor thereof, a hematopoietic stem cell (HSC) or a progenitor thereof, or an endothelial progenitor cell.

8. The composition of claim 6, wherein the layer consisting of hydrogel encapsulating the cell is characterized by a stiffness of about 0.1 to about 500 kPa.

9. The composition of claim 6, wherein the composition is an injectable composition.

10. The composition of claim 9, wherein the composition is an injectable composition for intravenous injection.

11. A method of preparing a composition comprising a plurality of hydrogel capsules, the method comprising:
    a) contacting a cell with a moiety capable of adhering to a cell and comprising a cross-linking catalyst, wherein the cross-linking catalyst is $Ca^{2+}$; and
    b) contacting the cell and the moiety with an alginate polymer comprising a plurality of polymer chains;
    wherein the cross-linking catalyst catalyzes a reaction that cross-links the plurality of polymer chains, thereby forming a composition comprising a plurality of hydrogel capsules, wherein at least 90% of the hydrogel capsules in the composition comprise a cell and a layer consisting of hydrogel encapsulating the cell;
    wherein at least 70% of the hydrogel capsules encapsulate a single cell;
    wherein the layer consisting of hydrogel encapsulating the cell has a thickness of less than 20 microns; and
    wherein the diameter of the hydrogel capsules is 50 microns or less.

12. The method of claim 11, wherein the moiety is a nanoparticle.

13. The method of claim 12, wherein the nanoparticle is a $CaCO_3$ nanoparticle.

14. The method of claim 11, wherein the cell is a mesenchymal stem cell (MSC) or a progenitor thereof, a hematopoietic stem cell (HSC) or a progenitor thereof, or an endothelial progenitor cell.

* * * * *

UNITED STATES PATENT AND TRADEMARK OFFICE
CERTIFICATE OF CORRECTION

PATENT NO. : 11,229,607 B2
APPLICATION NO. : 15/321458
DATED : January 25, 2022
INVENTOR(S) : Jae-Won Shin et al.

Page 1 of 1

It is certified that error appears in the above-identified patent and that said Letters Patent is hereby corrected as shown below:

In the Specification

At Column 1, Lines 17-19, please replace "The invention was supported, in whole, or in part, by a National Institutes of Health (NIH) ROI grant EB014703-03. The Government has certain rights in the invention." with --This invention was made with government support under EB014703 awarded by National Institutes of Health (NIH). The government has certain rights in this invention.--

Signed and Sealed this
Fourth Day of October, 2022

Katherine Kelly Vidal
*Director of the United States Patent and Trademark Office*